(12) United States Patent
Schmidt et al.

(10) Patent No.: US 11,571,127 B2
(45) Date of Patent: *Feb. 7, 2023

(54) RECHARGE OF IMPLANTED MEDICAL DEVICES

(71) Applicant: Medtronic, Inc., Minneapolis, MN (US)

(72) Inventors: Craig L. Schmidt, Eagan, MN (US); Gordon O. Munns, Stacy, MN (US)

(73) Assignee: Medtronic, Inc., Minneapolis, MN (US)

( * ) Notice: Subject to any disclaimer, the term of this patent is extended or adjusted under 35 U.S.C. 154(b) by 292 days.

This patent is subject to a terminal disclaimer.

(21) Appl. No.: 16/915,218

(22) Filed: Jun. 29, 2020

(65) Prior Publication Data
US 2020/0328615 A1    Oct. 15, 2020

Related U.S. Application Data

(63) Continuation of application No. 15/416,655, filed on Jan. 26, 2017, now Pat. No. 10,707,692.

(51) Int. Cl.
*A61N 1/372*    (2006.01)
*A61B 5/00*    (2006.01)
(Continued)

(52) U.S. Cl.
CPC .............. *A61B 5/0031* (2013.01); *A61B 5/00* (2013.01); *A61B 5/68* (2013.01); *A61N 1/362* (2013.01); *A61N 1/3787* (2013.01); *A61N 1/37223* (2013.01); *A61N 1/37229* (2013.01); *A61N 1/3962* (2013.01); *H01F 38/14* (2013.01); *H02J 50/10* (2016.02); *H02J 50/12* (2016.02);
(Continued)

(58) Field of Classification Search
CPC ................ A61N 1/372; A61N 1/37211; A61N 1/37217; A61N 1/37223; A61N 1/37229; A61N 1/378; A61N 1/3787
See application file for complete search history.

(56) References Cited

U.S. PATENT DOCUMENTS

| 5,117,824 A | 6/1992 | Keimel et al. |
| 6,047,214 A | 4/2000 | Mueller |

(Continued)

FOREIGN PATENT DOCUMENTS

| EP | 2451526 B2 | 6/2013 |
| WO | 2000066221 A1 | 11/2000 |

(Continued)

OTHER PUBLICATIONS

Carta, et al., "A wireless power supply system for robotic capsular endoscopes," Sensors and Actuators A, Aug. 2010, pp. 177-183.
(Continued)

*Primary Examiner* — Eugene T Wu
(74) *Attorney, Agent, or Firm* — Shumaker & Sieffert, P.A.

(57) ABSTRACT

Systems, devices and methods are disclosed that allow recharging a power source located in an implanted medical device implanted in a patient, the recharging device comprising first and second pairs of electrical coils configured to generate first and second uniform magnetic fields in overlapping first and second cylindrical regions located between the respective pairs of electrical coils.

20 Claims, 19 Drawing Sheets

(51) Int. Cl.

| | | |
|---|---|---|
| *H02J 50/12* | (2016.01) | |
| *H02J 50/80* | (2016.01) | |
| *A61N 1/378* | (2006.01) | |
| *A61N 1/362* | (2006.01) | |
| *A61N 1/39* | (2006.01) | |
| *H01F 38/14* | (2006.01) | |
| *H02J 50/10* | (2016.01) | |
| *A61B 5/024* | (2006.01) | |
| *A61N 1/375* | (2006.01) | |
| *A61B 5/11* | (2006.01) | |
| *A61B 5/08* | (2006.01) | |
| *A61B 5/01* | (2006.01) | |
| *H02J 7/00* | (2006.01) | |
| *H02J 50/40* | (2016.01) | |
| *H02J 7/02* | (2016.01) | |

(52) U.S. Cl.
CPC ............. *H02J 50/80* (2016.02); *A61B 5/01* (2013.01); *A61B 5/024* (2013.01); *A61B 5/02405* (2013.01); *A61B 5/0816* (2013.01); *A61B 5/1118* (2013.01); *A61B 2560/0219* (2013.01); *A61N 1/3756* (2013.01); *A61N 1/3758* (2013.01); *A61N 1/37205* (2013.01); *H02J 7/00034* (2020.01); *H02J 7/0047* (2013.01); *H02J 7/00309* (2020.01); *H02J 7/02* (2013.01); *H02J 50/402* (2020.01)

(56) References Cited

U.S. PATENT DOCUMENTS

| | | | |
|---|---|---|---|
| 7,211,986 | B1 | 5/2007 | Flowerdew et al. |
| 7,225,032 | B2 | 5/2007 | Schmeling et al. |
| 7,286,881 | B2 | 10/2007 | Schommer et al. |
| 8,204,602 | B2 | 6/2012 | Kallmyer |
| 8,244,367 | B2 | 9/2012 | Wahlstrand et al. |
| 8,278,871 | B2 | 10/2012 | Kallmyer |
| 8,473,066 | B2 | 6/2013 | Aghassian et al. |
| 8,554,322 | B2 | 10/2013 | Olson et al. |
| 8,676,318 | B2 | 3/2014 | Carbunaru et al. |
| 8,676,337 | B2 | 3/2014 | Kallmyer |
| 8,751,001 | B2 | 6/2014 | Grevious et al. |
| 8,864,676 | B2 | 10/2014 | Beasley et al. |
| 8,901,775 | B2 | 12/2014 | Armstrong et al. |
| 9,216,297 | B2 | 12/2015 | Kast et al. |
| 9,339,659 | B2 | 5/2016 | Carbunaru et al. |
| 9,700,730 | B2 | 7/2017 | Carbunaru et al. |
| 10,695,572 | B2 | 6/2020 | Maile et al. |
| 10,707,692 | B2 | 7/2020 | Schmidt et al. |
| 2006/0061325 | A1* | 3/2006 | Tang ............... H01F 38/14 320/108 |
| 2008/0027513 | A1 | 1/2008 | Carbunaru |
| 2009/0069869 | A1 | 3/2009 | Stouffer et al. |
| 2009/0112291 | A1 | 4/2009 | Wahlstrand |
| 2009/0270951 | A1 | 10/2009 | Kallmyer |
| 2010/0225174 | A1 | 9/2010 | Jiang |
| 2011/0004278 | A1 | 1/2011 | Aghassian et al. |
| 2011/0210621 | A1 | 9/2011 | Iwaisako |
| 2011/0248673 | A1 | 10/2011 | Aerts et al. |
| 2012/0119699 | A1 | 5/2012 | Carbunaru |
| 2013/0009594 | A1 | 1/2013 | Osswald |
| 2013/0293025 | A1 | 11/2013 | Xu et al. |
| 2014/0276928 | A1 | 9/2014 | Vanderpool et al. |
| 2015/0180267 | A1 | 6/2015 | Romanelli |
| 2015/0204928 | A1 | 7/2015 | Hoover |
| 2015/0244178 | A1* | 8/2015 | Tang ............... H02J 50/12 307/104 |
| 2016/0175600 | A1 | 6/2016 | Amir et al. |
| 2016/0336813 | A1 | 11/2016 | Yeh et al. |
| 2016/0339256 | A1 | 11/2016 | Poon et al. |
| 2017/0040826 | A1 | 2/2017 | Arendarik |
| 2017/0043077 | A1 | 2/2017 | Tuseth |
| 2017/0170688 | A1 | 6/2017 | Maniktala |
| 2017/0201118 | A1* | 7/2017 | Nejatali ............ H02J 50/40 |
| 2017/0281955 | A1 | 10/2017 | Maile et al. |
| 2018/0212451 | A1 | 7/2018 | Schmidt et al. |
| 2019/0247669 | A1 | 8/2019 | Nielsen et al. |

FOREIGN PATENT DOCUMENTS

| | | |
|---|---|---|
| WO | 2007/064609 A1 | 6/2007 |
| WO | 2009131723 A1 | 10/2009 |
| WO | 2013/190471 A1 | 12/2013 |
| WO | 2017218353 A1 | 12/2017 |

OTHER PUBLICATIONS

Miao, et al., "An Efficient Wireless Power Transmission System for the Capsule Endoscoy Application," Nov. 2011, IEEE, pp. 221-224.

Zhiwei, et al., "Efficiency optimization of wireless power transmission systems for active capsule endoscopes," Physiological Measurement, 32, Aug. 2011, pp. 1561-1573.

Basar, et al., "Performance Evaluation of Power Transmission Coils for Powering Endoscopic Wireless Capsules," Aug. 2015, IEEE, pp. 2263-2266.

Bingquan, et al., "Portable wireless power transmission system of a video capsule endoscopy: design and realization," International Conference on Biomedical Engineering and Biotechnology, May 2012, pp. 409-412.

Jia, et al., "The optimization of wireless power transmission: design and realization," The International Journal of Medical Robotics and Computer Assisted Surgery, Int. J. Med Robotics Comput Assist Surg, Apr. 2012; 8: pp. 337-347.

Padron, et al., "Simulation and Construction of a Maxwell Coil," Florida Atlantic University, 2015, accessed on Jan. 26, 2017, 1 pp. Applicant points out in accordance with MPEP 609.04(a) that the 2015 year of publication is sufficiently earlier than the effective U.S filing date of the present application, and any foreign priority date that the particular month of publication is not in issue.

Lenaerts, et al., "Inductive powering of a freely moving system," Sensors and Actuators, Sep. 2005, available online Mar. 2, 2005, pp. 522-530.

Ho, et al., "Wireless Power Transfer to Deep-Tissue Microimplants," PNAS, Jun. 3, 2014, vol. 111, No. 20, pp. 7974-7979.

Maile, PhD, et al., "Wireless Power Transfer for Deeply Implanted Medical Devices (IMD)," Boston Scientific, presented Dec. 5-7, 2016 at Biological & Chemical Sensors Summit, San Diego, CA, 20 slides.

Yates, "Wireless power delivery for ventricular assist devices," Imperial College, London, Dec. 7, 2017, presented Dec. 5-7, 2017 at Biological & Chemical Sensors Summit, San Diego, CA, 40 slides.

Von Novak, "Power Systems for Medical Implants," Qualcomm Technologies, Inc., presented Dec. 5-7, 2016 at Biological & Chemical Sensors Summit, San Diego, CA, 24 slides.

Wilken-Resman, et al., "Power Transfer Prediction Tool for Medical Implants," Qualcomm Technologies, presented Dec. 5-7, 2016 at Biological & Chemical Sensors Summit, San Diego, CA, 15 slides.

(PCT/US2018/014665) PCT Notification of Transmittal of the International Search Report and the Written Opinion of the International Searching Authority, dated Apr. 17, 2018, 12 pages.

Prosecution History from U.S. Appl. No. 15/416,655, dated May 9, 2019 through Dec. 10, 2019, 46 pp.

International Preliminary Report on Patentability from International Application No. PCT/US2018/014665, dated Jul. 30, 2019, 6 pp.

Prosecution History from U.S. Appl. No. 15/893,044, dated Dec. 10, 2020 through Jun. 11, 2021, 22 pp.

U.S. Appl. No. 15/893,044, filed by Nielsen et al., filed Feb. 9, 2018.

* cited by examiner

RECHARGE OF IMPLANTED MEDICAL DEVICES

This application is a continuation of U.S. patent application Ser. No. 15/416,655, filed Jan. 26, 2017, the entire content of which is incorporated herein by reference.

TECHNICAL FIELD

The disclosure relates to methods and systems to recharge a power source located within a medical device that has been implanted in a patient.

BACKGROUND

Various implantable medical devices have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, implantable loop recorders, and pressure sensors, among others. Such devices may be associated with leads that position electrodes or sensors at a desired location, or may be leadless with electrodes integrated into the device can. These devices may have the ability to wirelessly transmit data either to another device implanted in the patient or to another instrument located externally of the patient, or both.

Although implantation of some devices requires a surgical procedure (e.g., pacemakers, defibrillators, etc.), other devices may be small enough to be delivered and placed at an intended implant location in a relatively noninvasive manner, such as by a percutaneous delivery catheter or transvenously. By way of illustrative example, implantable miniature sensors have been proposed and used in blood vessels to measure directly the diastolic, systolic and mean blood pressures, as well as body temperature and cardiac output of a patient. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. In addition, miniaturized pacemakers that may be implanted directly within a patient's heart with or without the need for external leads, have been proposed, built, and adapted to provide both pacing and other electrical therapy to the patient.

SUMMARY

The disclosure describes implantable medical devices, systems, and associated techniques, structures, and assemblies configured to provide recharging of power sources within medical devices that have been implanted within a patient. The implanted medical devices including these power sources to be recharged are often small devices that have been implanted relatively deeply within the patient, for example implanted internally with the heart of a patient. An example of such a device is the Medtronic® Micra® self-contained pacemaker that is designed to be implanted internally within the heart of a patient, and in various examples requires no external leads coupled to the device in order to provide pacing and electrical stimulation to the heart.

Due to the need to miniaturize these devices so that they may be implanted in the desired locations, such as within the heart, while maintaining a small size in or to minimize any obstruction, e.g., to blood flow, created by the device once implanted, such devices are often provided with a unidirectional or planar receiving antenna to conserve space within the device and to reduce battery usage. These antennae are routinely used for telemetry and communications to and from the device. The application of the antenna for inductive recharging of the devices faces the same constraints, e.g., size and directionality constraints, as faced when using the device for telemetry and communication functions. In addition, the exact orientation of the device following the implantation of the device may not be known, and/or may not be easily re-positioned to allow for optimization of operations (e.g., communication efficiency in the case of telemetry and recharging power transfer efficiency in the case of inductively coupled recharging), thus adding to the challenge of determining the proper or at least the most efficient orientation of the devices used to recharge the power source or sources included within the implanted device. These factors, e.g., the combination of deeply implanted devices having limited receiving antenna orientations that provide good coupling for inductively coupled recharge are addressed by the systems, devices and methods described in this disclosure. Additionally, and importantly, the devices, systems, and methods may include pairs of coils, such as Helmholtz coils, configured to generate a rather uniform field such that the inductively coupled power does not depend on the detailed position of the implanted device, (e.g., X, Y, Z spatial coordinates). This ability to provide a high level of inductive coupling between the coils of a recharging system with a single antenna of an implanted device continues to be important advantage in the performance aspects of the devices, systems, and methods disclosed herein.

Examples include a recharging system for recharging a power source located in an implanted medical device implanted in a patient, the recharging system comprising: a first pair of electrical coils having a first central axis, the first pair of coils configured to generate a first uniform magnetic field in a first cylindrical region located between the first pair of coils when the first pair of coils is electrically energized; and a second pair of electrical coils having a second central axis perpendicular to the first central axis, the second pair of electrical coils configured to generate a second uniform magnetic field in a second cylindrical region located between the second pair of coils when the second pair of coils is electrically energized; wherein the first uniform magnetic field and the second uniform magnetic field form a resultant magnetic field within an area common to both the first cylindrical region and the second cylindrical region, the resultant magnetic field operable to provide a charging energy to at least one receiving antenna of the implanted medical device located within the resultant magnetic field when the first pair of coils and the second pair of coils are electrically energized.

Examples also include a system for recharging an implanted medical device, the system comprising: a first pair of electrical coils having a first central axis, the first pair of coils configured to provide a first uniform magnetic field in a first cylindrical region located between the first pair of coils when the first pair of coils is electrically energized; a second pair of electrical coils and having a second central axis, the second pair of coils configured to provide a second uniform magnetic field in a second cylindrical region located between the second pair of coils when the second pair of coils is electrically energized; and a source of electrical energy coupled to the first pair of coils and to the second pair of coils, the source configured to provide electrical energy to energize the first pair of electrical coils and to energize the second pair of electrical coils; wherein the first uniform magnetic field and the second uniform magnetic field form a resultant magnetic field within an area common to both the first cylindrical region and the second cylindrical region, the resultant magnetic field operable to provide a charging energy to at least one receiving antenna of the implanted medical device located within the resultant magnetic field when the first pair of coils and the second pair of coils are electrically energized.

Examples also include a method for recharging a power source located in an implanted medical device implanted in a patient, the method comprising: generating, by a signal generator, an electrical signal having a varying voltage waveform; applying, by a first driver circuit, the electrical signal to a first pair of electrical coils, the first pair of electrical coils having a first central axis, the first pair of coils configured to generate a first uniform magnetic field in a first cylindrical region located between the first pair of coils when the first pair of coils is electrically energized; and applying, by a second driver circuit, the electrical signal to a second pair of electrical coils, the second pair of electrical coils having a second central axis, the second pair of coils configured to generate a second uniform magnetic field in a second cylindrical region located between the second pair of coils when the second pair of coils is electrically energized; wherein the first uniform magnetic field and the second uniform magnetic field form a resultant magnetic field within an area common to both the first cylindrical region and the second cylindrical region within an area common to both the first cylindrical region and the second cylindrical region, the resultant magnetic field operable to provide a charging energy to at least one receiving antenna of the implanted medical device located within the resultant magnetic field when the first pair of coils and the second pair of coils are electrically energized.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF THE FIGURES

The details of one or more examples of this disclosure are set forth in the accompanying drawings and the description below. Other features, objects, and advantages of this disclosure will be apparent from the description and drawings, and from the claims.

Figure 1:
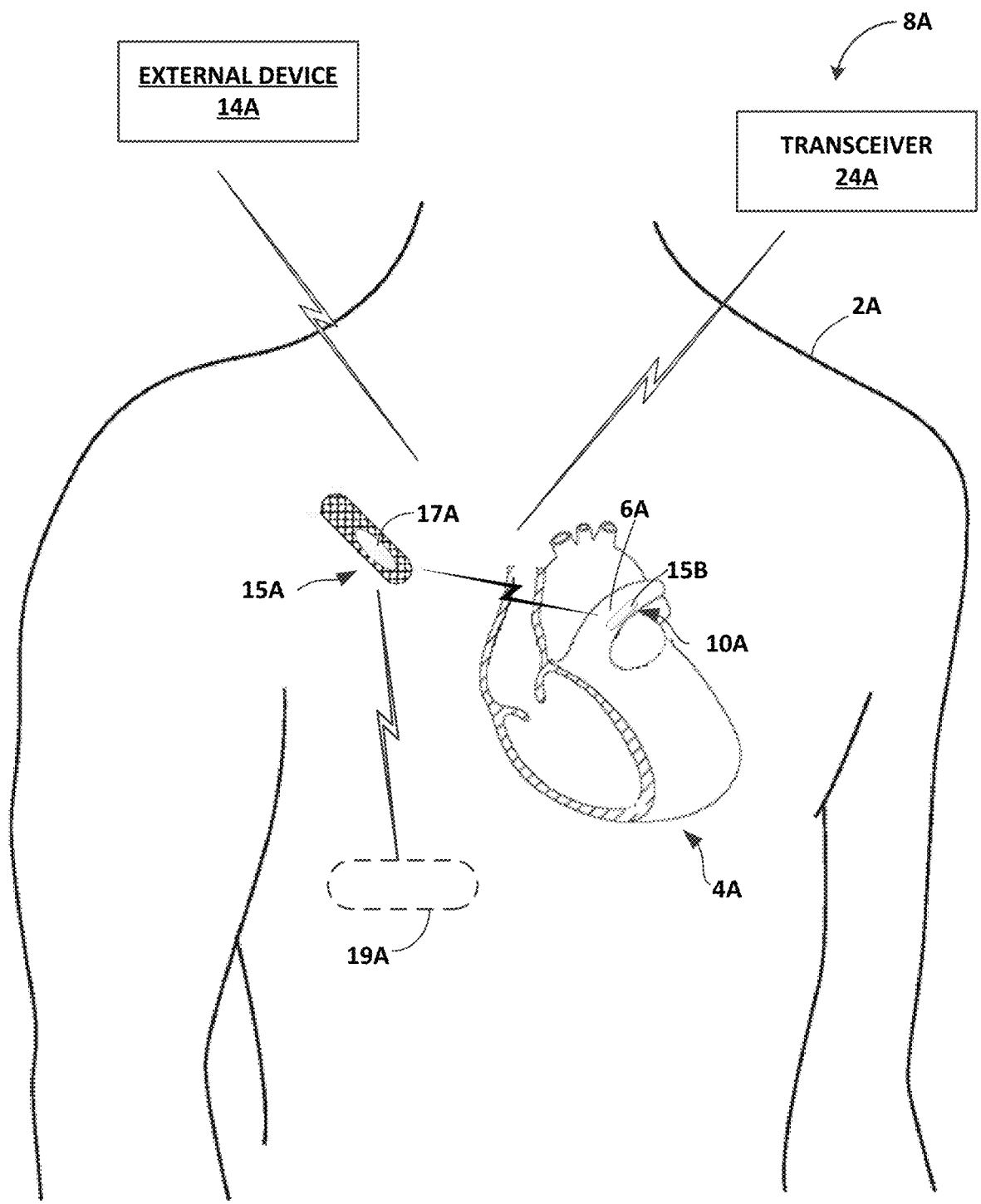
FIG. 1 is a conceptual drawing illustrating an example medical device system in conjunction with a patient according to various examples described in this disclosure.

In the figures, use of a same reference number or a same reference number with a letter extension may be used to indicate a same or corresponding device or element when used in a same drawing or in different drawings. In addition, unless otherwise indicated, devices and/or other objects such as a patient, an implantable medical device, or an electrical device such as an electrical coil, are not necessarily illustrated to scale relative to each other and/or relative to an actual example of the item being illustrated. In particular, various drawings provided with this disclosure illustrate a "patient" represented by a human-shaped outline, and are not to be considered drawn to scale relative to an actual human patient or with respect to other objects illustrated in the same figure unless otherwise specifically indicated in the figure for example by dimensional indicators, or for example as otherwise described in the text of the disclosure.

DETAILED DESCRIPTION

Fast recharge of small, deeply implanted devices such as the Medtronic® Micra® Pacemaker via transdermal, magnetic induction presents many challenges. These include providing an adequate magnetic field intensity and frequency at the implant location such that rapid recharge can be accomplished without exceeding electric field and magnetic field exposure safety limits, while accounting for an uncontrolled orientation of the implanted device, and while accounting for the true spatial location of the device in addition to the device/antenna orientation. In various examples of implanted medical devices, a primary (non-rechargeable) battery has a finite energy reservoir which limits its mission life based on its size and energy density (for a given energy usage rate). This limits the useful duration of the implanted device. A rechargeable battery conceptually offers a semi-infinite reservoir of energy in which the size of the battery and charged energy density determines the recharge frequency rather than the mission life (under the assumption of negligible battery capacity fade). A result of a semi-infinite energy source is the opportunity to provide additional features and functions that would be limited or unavailable given a finite energy source constraint. Another result of this semi-infinite energy source is the potential reduction or elimination of a need to perform a surgically invasive device replacement procedure required due to exhausting the capacity of the primary (i.e., non-rechargeable) battery. The devices, systems, and techniques described in this disclosure address many of the challenges associated with recharging these power sources within the implanted medical devices.

The systems, devices and method described in this disclosure provide for fast recharge of a battery in a small, deeply implanted device, such as the Micra® leadless pacemaker, in some examples using a unique configuration of Helmholtz coils. A Helmholtz coil is actually a pair of identically sized, circular coils located apart by a distance equal to one radius of the coils. This configuration has the unique property in that the magnetic field in the cylindrical region between the two coils is substantially uniform both axially and radially throughout the cylindrical region. In some examples, the magnetic field intensity varies no more than approximately 7% throughout the areas of the cylindrical region. As used through this description, the uniformity of the magnetic field intensities may be within this 7% range of variation within the areas and/or regions described as having a uniform magnetic field. Thus, it is possible to establish a magnetic field at the implanted device that is independent of both implant depth and implant location, solving two of the three challenges listed earlier. In some examples, the coils used in the recharging process may include at least one set of coils configured as a Maxwell coil, including a three-coil set of coils arranged along a common central axis, as further described in this disclosure. Use of other coil configurations that do not necessarily constitute a Helmholtz coil and/or a Maxwell coil are contemplated for use by the recharging systems described in this disclosure.

The systems, devices and methods described in some examples in this disclosure provide a solution to the orientation challenge by using two or three sets of Helmholtz coils in specific orientations. Additionally, short solenoidal pairs of coils or a solenoidal coil in one-dimension along with Helmholtz or solenoid pairs of coils in other dimensions could be used. In the three sets of Helmholtz coils implementation, the coils are arranged such that their fields are mutually orthogonal. The three-axis field orientation assures that there are no nulls (and minima are reduced or eliminated) for any given orientation of the receiving coil of an implanted device being recharged by the systems described herein, wherein nulls are defined as areas within a generated magnetic field where the vector representing the resultant magnetic field in an area has a value of zero. This provides a solution similar to the use of a three-axis receiving coil in the implanted device, but it allows a much simpler and more space-efficient design of the implanted device since a single receiving coil can now be used in the implanted device. In some examples of the recharging systems described in this disclosure, two sets of Helmholtz coils are arranged to provide orthogonal fields, but in which a first set of coils can be rotated around an axis aligned with the axis of a second set of coils. This arrangement again assures that no nulls (or minima) are possible with any given orientation of the receiving coils within the implanted device or devices being recharged. The systems, devices and methods described in this disclosure not only assure no nulls, but providing the ability to match the direction of the magnetic field intensity provided by the recharging coils to any single receiving coil/antenna direction of an implanted medical device, for example by steering the transmit magnetic field intensity to provide maximum coupling between the magnetic field intensity and the receiving coil/antenna of the implanted medical device.

FIG. 1 is a conceptual drawing illustrating an example of some components of a medical device system 8A in conjunction with a patient 2A according to various examples described in this disclosure. The systems, devices, and techniques described in this disclosure provide for charging of power sources of the internal, and in some instances deeply implanted devices, such as IMD 15A and IMD 15B of medical device system 8A, as further described below. For purposes of this description, knowledge of cardiovascular anatomy is presumed and details are omitted except to the extent necessary or desirable to explain the context of the techniques of this disclosure. In the illustrated example, medical device system 8A includes an implantable medical device (IMD) 15A, also referred to as implantable monitoring device 15A or an implantable hub device, or implantable loop recorder. Medical device system 8A also includes implantable pressure sensing device 15B, also referred to as IMD 15B. IMD 15B may be implanted within pulmonary artery 6A of heart 4A. In some examples, pulmonary artery 6A of heart 4A may comprise a left pulmonary artery, whereas in other examples, pulmonary artery 6A may comprise a right pulmonary artery. For the sake of clarity, a fixation assembly for IMD 15B is not depicted in FIG. 1. Medical device system 8A is an example of several components of a medical device system configured to implement the techniques described herein for monitoring physiological parameters of patient 2A, such as activity counts, heart rates, respiration rates, systemic blood pressures, body temperature(s), and body postures, and to allow for recharging of a power source, such as a battery, located within any of the one or more implanted medical devices 15A,15B included in system 8A. The medical device system 8A typically includes provisions for interrogating these devices through a wireless or other communication protocol using an external "instrument" that includes an external-to-the-patient antenna and software/firmware interface to collect data.

In the illustrated example, IMD 15A is an insertable cardiac monitor (ICM) capable of sensing and recording cardiac electrogram (EGM) (also referred to as an ECG or EKG electrocardiogram when external electrodes are placed on the skin) signals from a position outside of heart 4A via electrodes. In some examples, IMD 15A includes or is coupled to one or more additional sensors, such as accelerometers, that generate one or more signals that vary based on patient motion and/or posture, blood flow, or respiration. IMD 15A may monitor a physiological parameter indicative of patient state, such as posture, heart rate, activity level, and/or respiration rate. IMD 15A may be implanted outside of the thorax of patient 2A, e.g., subcutaneously or submuscularly, such as the pectoral location illustrated in FIG. 1. In some examples, IMD 15A may take the form of a Reveal LINQ® ICM, available from Medtronic plc, of Dublin, Ireland.

In various examples, to keep the size dimensions, in particular a thickness dimension, for IMD 15A as small as possible, a planar antenna 17A (receiving/transmitting antenna), for example an antenna comprising a conductive trace printed on a planar surface such as a substrate, may be provided within IMD 15A. The advantage of a planar design, as compared to for example a three-dimensional antenna, is that the uni-directional or planar format of the antenna may take up less space within the device, and may be more easily packaged into the device when size and space are of concern, for example with respect to IMD 15A. One disadvantage associated with the planar antenna may be that coupling efficiencies with respect to receiving power transmitted from outside patient 2A to the antenna 17A may be orientation specific. For example, the orientation of the electromagnetic and magnetic fields being imposed on IMD 15A relative to the antenna 17A have an effect on the efficiency of transferring power from the electromagnetic and magnetic fields imposed on IMD 15A and power transfer efficiency in inducing corresponding electromagnetic energy in antenna 17A. Because the orientation of IMD 15A may not be precisely known, or may shift at some point in time after implantation into patient 2A, a change in orientation of IMD 15A may cause issues, including variations in the power transfer efficiencies, with recharging a power source and/or a battery located within IMD 15A.

As illustrated in FIG. 1, IMD 15B may be implanted, as one example, within a pulmonary artery 6A of patient 2A, and may include pressure sensing circuitry configured to measure the cardiovascular pressure within the pulmonary artery 6A of patient 2A. In some examples, IMD 15B may be a part of sensor assembly 10A. In some examples, IMD 15B may include wireless communication circuitry, including tissue conduction communication (TCC) configured to receive a trigger signal from IMD 15A at an antenna provided in IMD 15B. The pressure sensing circuitry of IMD 15B may be configured to measure the cardiovascular pressure of patient 2A in response to receiving the trigger signal. In either case, IMD 15B may be configured to transmit the measured pressure values to IMD 15A by wireless communication. For example, IMD 15B may transmit measurements and data acquired by IMD 15B related to pulmonary artery pressure and other information generated by IMD 15B to IMD 15A. In some examples, IMD 15B may transmit data and other information to an external device, such as external device 14A. External device 14A may also be referred to as an "instrument," which may include any of the devices described throughout the disclosure as devices located externally to the patient, and in some examples may be included as part of a recharging system configured to recharge the battery or other power source provided within IMD 15A and/or IMD 15B.

In addition, because IMD 15B may be implanted within the pulmonary artery 6A of patient 2A, there is an interest in miniaturizing IMD 15B to the extent possible while maintaining the required functionality of the device. As such, in a similar manner as described above with respect to IMD 15A, there may be a need to limit the arrangement and space allocated for the antenna provided within IMD 15B to perform the communication functions, for example as described above, for IMD 15B. This same antenna may, in some examples, be used by IMD 15B to receive the energy inductively used to recharge the power source provided within IMD 15B based on electromagnetic and magnetic fields imposed on IMD 15B. The limitation of size and space for IMD 15B may require use of an antenna, such as a planar antenna, that is subject to coupling inefficiencies based on the distance from the source, for example a coil external to patient 2A (not shown in FIG. 1), which is configured to provide the inductive charge, and also with respect to the orientation of the antenna in IMD 15B relative to the orientation of the fields being provided by the external coil(s).

The systems, devices, and methods described in this disclosure provide for charging of these internal and in some instances deeply implanted devices, such as IMD 15A and IMD 15B, even when these devices include planar antennas or other configurations of antennas that are orientation specific with respect to coupling efficiencies between the antenna of the device being inductively recharged and the orientation of one or more coils being used to provide the electromagnetic and magnetic fields being imposed on the device for the purpose of inductively recharging a power source, such as a battery, located within the device being inductively charged.

In various examples, IMD 15A and/or 15B are configured to wirelessly communicate with external device 14A. External device 14A may be a computing device, e.g., used in a home, ambulatory, clinic, or hospital setting, to wirelessly communicate with IMD 15A and/or IMD 15B. External device 14A may be coupled to a remote patient monitoring system, such as Carelink®, available from Medtronic plc, of Dublin, Ireland. External device 14A may be, as examples, a programmer, external monitor, or consumer device, e.g., smart phone. External device 14A may be used to program commands or operating parameters into IMD 15A and/or IMD 15B for controlling the functioning of these devices. External device 14A may be used to interrogate IMD 15A and/or IMD 15B to retrieve data, including device operational data as well as physiological or neurological data accumulated in memory in either of these devices. The interrogation may be automatic, e.g., according to a schedule, or in response to a remote or local user command. One or more of these external devices may also be referred to as an "instrument" or as a group of instruments.

In various examples, communications provided from IMD 15A and/or IMD 15B may include data and/or other information related to the inductive charging of these devices. For example, when an electromagnetic or magnetic field is imposed on IMD 15A and 15B for the purpose of inductively charging these devices, information related to the coupling efficiency of inductive coupling to the device, and/or for example the state of charge (e.g., percent of charge relative to a full charge) may be transmitted from one or both of IMD 15A and/or IMD 15B to external device 14A as part of the recharging process. Other information, such as time to full charge, rate of recharge, and temperature of the device may also be provided as transmitted information from the device(s) being recharged. In some examples, this information by be used to adjust parameters, such as the field strength of the fields used to induce the energy in the antenna for recharging of IMD 15A and/or IMD 15B, or for example to provide information used to re-orient the coils that are providing the fields used for the induced recharging energy provided to these devices. In addition, information may be provided by IMD 15A and/or IMD 15B that is indicative of the level of the recharging of one or both of IMD 15A and/or IMD 15B that has been achieved or completed, which may then be used to determine when to further regulate, stop, or otherwise terminate the recharging process. For example, during the recharging process IMD 15A and/or IMD 15B may transmit data or other information indicating that the device, respectively, is fully recharged. The indication may then be used by the external devices providing the fields (not show in FIG. 1) to stop the charging process, which may include removing the fields used to recharge IMD 15A and/or IMD 15B from being imposed on these devices. In addition, monitoring the temperature of the device may be important, as overheating of an implanted device as a result of the recharging process may damage the device, or present a safety issue for the patient. Adjustments to the intensities of the fields being imposed on the device, and/or termination of the recharging process altogether may be made based on the monitored temperature of the device being recharged as a part of the recharging process. Examples of communication techniques used by IMD 15A and/or 15B and external device 14A are not limited to any particular communication technique or communication protocol, and in some examples include tissue conductance communication (TCC) or RF telemetry, which may be an RF link established via Bluetooth®, WiFi, or medical implant communication service (MICS).

In various examples, one or more additional sensor circuits may be located outside of or separately located relative to the IMD 15A. These one or more additional sensor circuits are illustratively represented by sensor circuits 19A. Sensor circuits 19A may include a single sensor circuit configured to sense a particular physiological or neurological parameter associated with patient 2A, or may comprise a plurality of sensor circuits, which may be located at various and/or different positions relative to patient 2A and/or relative to each other, and are configured to sense one or more physiological parameters associated with patient 2A.

For example, sensor circuits 19A may include a sensor operable to sense a body temperature of patient 2A in a location of the sensor circuits 19A, or at the location of the patient where a temperature sensor coupled by a lead to sensor circuits 19A is located. In another example, sensor circuits 19A may include a sensor configured to sense motion, such as steps taken by patient 2A and/or a position or a change of posture of patient 2A. In various examples, sensor circuits 19A may include a sensor that is configured to detect breaths taken by patient 2A. In various examples, sensor circuits 19A may include a sensor configured to detect heartbeats of patient 2A. In various examples, sensor circuits 19A may include a sensor that is configured to measure systemic blood pressure of patient 2A.

In some examples, one or more of the sensors comprising sensor circuits 19A may be implanted within patient 2A, that is, implanted below at least the skin level of the patient. In some examples, one or more of the sensors of sensor circuits 19A may be located externally to patient 2A, for example as part of a cuff or as a wearable device, such as a device imbedded in clothing that is worn by patient 2A. In various examples, sensor circuits 19A may be configured to sense one or more physiological parameters associated with patient 2A, and to transmit data corresponding to the sensed physiological parameter or parameters to IMD 15A, as represented by the lightning bolt coupling sensor circuits 19A to IMD 15A. Transmission of data from sensor circuits 19A to IMD 15A in various examples may be performed via wireless transmission, as would be understood by those of skill in the art. In various examples, transmission of data from one or more of the sensors comprising sensor circuits 19A to IMD 15A may be performed by a wired connection between the sensor circuits 19A and IMD 15A. When one or more of sensors 19A are implanted devices that are implanted within patient 2A, the systems, devices, and recharging techniques as described throughout this disclosure may be used to also recharge a power source, such as a battery, located within the implanted sensor(s) and configured to provide power to the sensor where the power source is located.

In various examples, IMD 15A and or IMD 15B may communicate wirelessly to an external device (e.g., an instrument or instruments) other than or in addition to external device 14A, such as transceiver 24A shown in FIG. 1. In various examples, external device 14A is a programming device, such as a handheld programmer, or for example a computer-type used to program and/or interrogate IMD 15A and/or IMD 15B. In various examples, external transceiver 24A as shown in FIG. 1 is an access point, such as access point 220 illustrated and described with respect to FIG. 7A, that provides a wireless communication link between IMD 15A and/or IMD 15B, such as network 222 also illustrated and described with respect to FIG. 7A. In various examples, transceiver 24A is communication circuitry 444 of recharging circuitry 440 shown in FIGS. 12A-12B, wherein communication circuitry 444 is configured to communicate with IMD 15A, and/or IMD 15B during the recharging process of these devices, as further described below. Examples of communication techniques used by any of the devices described above with respect to FIG. 1 and transceiver 24A may include radiofrequency (RF) telemetry, which may be an RF link established via Bluetooth®, WiFi, or medical implant communication service (MICS).

Figure 2:
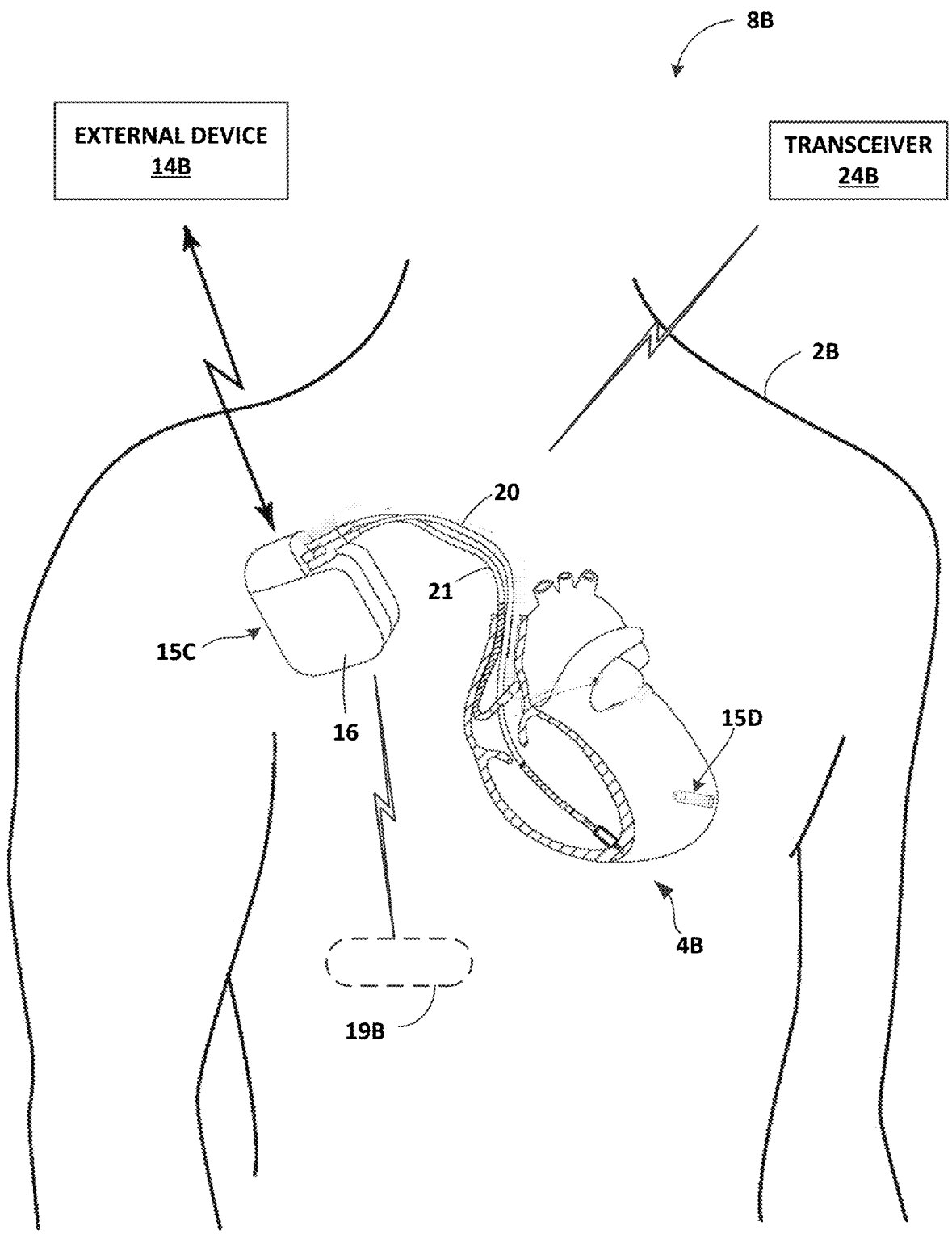
FIG. 2 is a conceptual drawing illustrating another example medical device system in conjunction with a patient according to various examples described in this disclosure.

FIG. 2 is a conceptual drawing illustrating another example medical device system 8B in conjunction with a patient 2B according to various examples described in this disclosure. The systems, devices, and techniques described in this disclosure provide for charging of these internal and in some instance deeply implanted devices, such as IMD 15C, IMD 15D, and sensors 19B, as illustrated and described with respect to FIG. 2, even when these devices include planar antennas or other configurations of antennas that are orientation specific with respect to coupling efficiencies between the antenna of the device being inductively recharged and the orientation of one or more coils being used to provide the electromagnetic and magnetic fields being imposed on the device for the purpose of inductively recharging a power source, such as a battery, located within the device being inductively charged. In various examples, IMD 15C and/or IMD 15D may represent a defibrillator, a cardiac resynchronization pacer/defibrillator, or a pacemaker.

In the illustrated example, medical device system 8B includes an IMD 15C coupled to a ventricular lead 20 and an atrial lead 21. In various examples, IMD 15C is an implantable cardioverter-defibrillator (ICD) capable of delivering pacing, cardioversion and defibrillation therapy to the heart 4B of a patient 2B. Ventricular lead 20 and atrial lead 21 are electrically coupled to IMD 15C and extend into the patient's heart 4B. Ventricular lead 20 includes electrodes (not labeled in FIG. 2) positioned on the lead in the patient's right ventricle (RV) for sensing ventricular EGM signals and pacing in the RV. Atrial lead 21 includes electrodes (not labeled in FIG. 2) positioned on the lead in the right atrium (RA) of patient 2B for sensing atrial EGM signals and pacing in the RA. Ventricular lead 20 and/or atrial lead 21 may also include coil electrodes used to deliver cardioversion and defibrillation shocks. The term "antitachyarrhythmia shock" may be used herein to refer to both cardioversion shocks and defibrillation shocks. IMD 15C may use both ventricular lead 20 and atrial lead 21 to acquire cardiac electrogram (EGM) signals from patient 2B and to deliver therapy in response to the acquired data. Medical device system 8B is shown as having a dual chamber IMD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein with respect to IMD 15C are housed within a sealed housing 16. Housing 16 (or a portion thereof) may be conductive so as to serve as an electrode for pacing or sensing, or as an active electrode during defibrillation. As such, housing 16 is also referred to herein as "housing electrode" 16. Housing 16 may include one or more electrodes with a high-capacitance portion and a low-capacitance portion. The high-capacitance portion and the low-capacitance portion may be formed using two different materials.

IMD 15C may transmit EGM signal data and cardiac rhythm episode data, as well as data regarding delivery of therapy by IMD 15C, to an external device 14B. In various examples, external device 14B is substantially similar to external device 14A as illustrated and described with respect to FIG. 1, and may provide any or all of the features and perform any or all of the functions illustrated and described with respect to external device 14A, and any equivalents thereof. For example, external device 14B as illustrated in FIG. 2 may be a computing device, e.g., used in a home, ambulatory, clinic, or hospital setting, to communicate with IMD 15C via wireless telemetry. External device 14B may be coupled to a remote patient monitoring system, such as Carelink®, available from Medtronic plc, of Dublin, Ireland. External device 14B may be, as examples, a programmer, external monitor, or consumer device, e.g., smart phone.

External device 14B may be used to program commands or operating parameters into IMD 15C for controlling its functioning, e.g., when configured as a programmer for IMD 15C. External device 14B may be used to interrogate IMD 15C to retrieve data, including device operational data as well as physiological data accumulated in IMD 15C memory. The interrogation may be automatic, e.g., per a schedule, or in response to a remote or local user command. Examples of communication techniques used by IMD 15C and external device 14B may include TCC and RF telemetry, which may be an RF link established via Bluetooth®, WiFi, or medical implant communication service (MICS).

In addition, system 8B may include transceiver 24B wirelessly coupled to communicate with IMD 15C. In some examples, transceiver 24B is transceiver 24A as illustrated and described above with respect to FIG. 1, and may provide some or all of the features and perform any or all of the functions illustrated and described with respect to transceiver 24A and/or external device 14A, and any equivalents thereof, with respect to system 8B.

In various examples, one or more additional sensor circuits may be located outside of or separately located relative to the IMD 15C. These one or more additional sensor circuits are illustratively represented by sensor circuits 19B. Sensor circuits 19B may include a single sensor circuit configured to sense a particular physiological parameter associated with patient 2A, or may comprise a plurality of sensor circuits, which may be located at various and/or different positions relative to patient 2A and/or relative to each other, and are configured to sense one or more physiological parameters associated with patient 2A. In various examples, sensor circuits 19B may include one or more of the sensors 19A as illustrated and described above with respect to FIG. 1, and may provide any of the features and perform any of the functions described above with respect to sensors 19B, but with respect to IMD 15C and system 8B.

In some examples, as illustrated in FIG. 2, medical device system 8B may also include an intracardiac pacing device IMD 15D. In the illustrated example, IMD 15D is implanted in the left-ventricle of patient 2B. e.g., internal to the heart 4B of patient 2B. In some examples, one or more IMDs like IMD 15D (not shown in FIG. 2) may additionally or alternatively be implanted within other chambers of heart 4B, or attached to the heart epicardially. IMD 15D may be configured to sense electrical activity of heart 4B and deliver pacing therapy, e.g., bradycardia pacing therapy, cardiac resynchronization therapy (CRT), anti-tachycardia pacing (ATP) therapy, and/or post-shock pacing, to heart 4B. IMD 15D may be attached to an interior wall of heart 4B via one or more fixation elements that penetrate the tissue. These fixation elements may secure IMD 15D to the cardiac tissue and retain an electrode (e.g., a cathode or an anode) on the housing of IMD 15D in contact with the cardiac tissue. In addition to delivering pacing pulses, IMD 15D may be capable of sensing electrical signals using the electrodes carried on the housing of IMD 15D. These electrical signals may be electrical signals generated by cardiac muscle and indicative of depolarizations and repolarizations of heart 4B at various times during the cardiac cycle.

In some examples, IMD 15C and IMD 15D may both be configured to deliver pacing therapy. In such examples, IMD 15C and IMD 15D may delivery pacing therapy to the right and left ventricles of heart 4B, respectively, to provide CRT pacing. Additionally, IMD 15C and IMD 15D may both be configured to detect tachyarrhythmias, and deliver antitachyarrhythmia therapy. IMD 15C and IMD 15D may be configured to coordinate their cardiac rhythm detection and treatment activities. In some examples, IMD 15C and IMD 15D may engage in wireless communication between IMD 15 and IMD 15D to facilitate such coordinated activity. The wireless communication may by via TCC, and may be one-way communication in which one device is configured to transmit communication messages and the other device is configured to receive those messages, or two-way communication in which each device is configured to transmit and receive communication messages.

For the remainder of the disclosure, a general reference to a medical device system 8 may refer collectively to include any examples of medical device systems 8A and 8B, a general reference to IMD 15 may refer collectively to include any examples of IMD 15A, IMD 15B, IMD 15C and IMD 15D, a general reference to sensor circuits 19 may refer collectively to include any examples of sensor circuits 19A and 19B, a general reference to external device 14 may refer collectively to include any examples of externals devices 14A and 14B, and a general reference to transceiver 24 may refer collectively to any examples of transceiver 24A and transceiver 24B.

Figure 3:
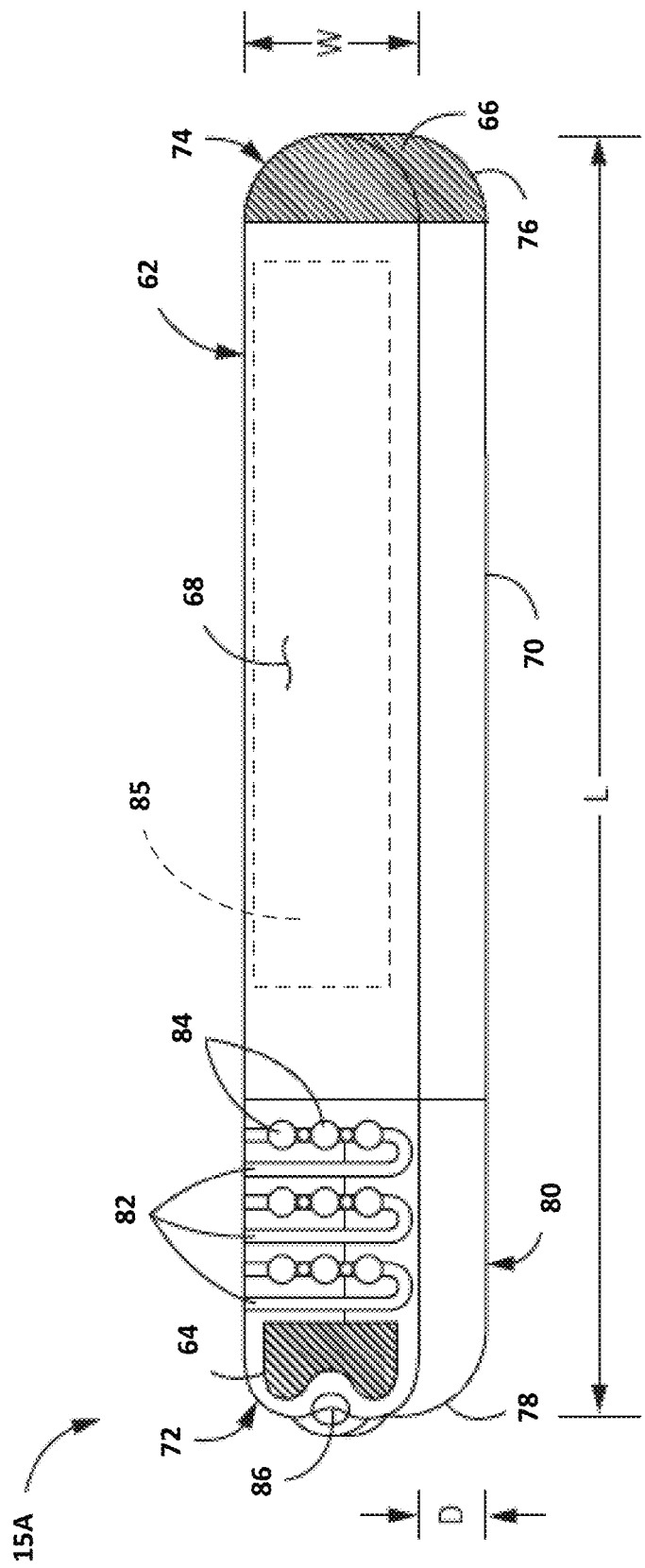
FIG. 3 is a conceptual drawing illustrating an example configuration of the implantable medical device IMD 15A of FIG. 1.

FIG. 3 is a conceptual drawing illustrating an example configuration of IMD 15A of FIG. 1. IMD 15A is an example of an implantable medical device that may be inductively recharged using the systems, devices, and methods described in this disclosure. In the example shown in FIG. 3, IMD 15A may be an implantable loop recorder diagnostic device, such as the Medtronic Reveal LINQ® Insertabel Cardiac Monitor developed by Medtronic, plc, of Dublin, Ireland. IMD 15A may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the IMD 15A, and protects the circuitry contained therein from body fluids when IMD 15A is implanted in a patient. Electrical feedthroughs may provide electrical connection of electrodes 64 and 66 or, in some examples, electrode 66 may comprise an uninsulated portion of an electrically conductive housing 62. A power source 85, such as battery is provided within IMD 15A, which provides power to the electronic circuitry of IMD 15A, and may at some point need to be recharged after IMD 15A has been implanted in a patient without the need to remove and re-implant IMD 15A. The inductive recharging devices, systems, and methods described in this disclosure are configurable to provide inductive recharging of the power source 85 while IMD 15A remains implanted in a patient.

In the example shown in FIG. 3, IMD 15A may be defined by a length L, a width W, and thickness or depth D and in some examples in the form of an elongated rectangular prism wherein the length L is much larger than the width W, which in turn is larger than the depth D. In one example, the geometry of the IMD 15A—in particular a width W greater than the depth D—is selected to allow IMD 15A to be inserted under the skin of the patient using a minimally invasive procedure and to remain in the desired orientation during insertion. For example, the device shown in FIG. 3 includes radial asymmetries (notably, the rectangular/prismatic shape) along the longitudinal axis that maintains the device in the proper orientation following insertion. In one example, the spacing between proximal electrode 64 and distal electrode 66 may range from thirty millimeters (mm) to fifty-five mm, thirty-five mm to fifty-five mm, and from forty mm to fifty-five mm, and may be any range or individual spacing from twenty-five mm to sixty mm. In addition, IMD 15A may have a length L that ranges from thirty mm to about seventy mm. In other examples, the length L may range from forty mm to sixty mm, forty-five mm to sixty mm, and may be any length or range of lengths between about thirty mm and about seventy mm. In addition, the width W of major surface 68 may range from three mm to ten mm, and may be any single or range of widths between three mm and ten mm. The thickness of depth D of 1 MB 15A may range from two mm to nine mm. In other examples, the depth D of 1 MB 15A may range from two mm to five mm and may be any single or range of depths from two mm to nine mm.

In addition, IMD 15A according to an example of the present disclosure has a geometry and size designed for ease of implant and patient comfort. Examples of IMD 15A described in this disclosure may have a volume of three cubic centimeters (cm) or less, one-and-a-half cubic cm or less, or any volume between three and one-and-a-half cubic centimeters. In addition, in the example shown in FIG. 3, proximal end 72 and distal end 74 are rounded to reduce discomfort and irritation to surrounding tissue once inserted under the skin of the patient. IMD 15A, including instrument, introducer, and method for inserting IMD 15A are described, for example, in U.S. Patent Application Publication No. 2014/0276928, incorporated herein by reference in its entirety.

In the example shown in FIG. 3, once inserted within the patient, the first major surface 68 faces outward, toward the skin of the patient while the second major surface 70 is located opposite the first major surface 68. Consequently, the first and second major surfaces may face in directions along a sagittal axis of patient 2A (see FIG. 1), and this orientation may be consistently achieved upon implantation due to the dimensions of IMD 15A. Additionally, an accelerometer, or axis of an accelerometer, may be oriented along the sagittal axis.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the IMD 15A, and ECG data may be transmitted via integrated antenna 82 (receiving antenna) to another medical device, which may be another implantable device or an external device, such as external device 14A illustrated in FIG. 1. Referring again to FIG. 3, in some examples electrodes 64 and 66 may additionally or alternatively be used for sensing any bio-potential signal of interest, which may be, for example, an EGM, EEG, EMG, or a nerve signal, from any implanted location. In some examples, IMD 15A may be implanted cranially in a location within the head areas of a patient, and proximal electrode 64 and distal electrode 66 are used to sense neurological signals.

In the example shown in FIG. 3, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 3, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64. The various electrode configurations allow for configurations in which proximal electrode 64 and distal electrode 66 are located on both first major surface 68 and second major surface 70. In other configurations, such as that shown in FIG. 3, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, IMD 15A may include electrodes on both major surface 68 and 70 at or near the proximal and distal ends of the device, such that a total of four electrodes are included on IMD 15A. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 3, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows IMD 15A to transmit and/or receive data. In other examples, integrated antenna 82 may be formed on the opposite major surface as proximal electrode 64, or may be incorporated within the housing 62 of IMD 15A. Antenna 82 may be coupled to recharging circuitry (not shown in FIG. 3), wherein antenna 82 is configured to enable inductive power transfer of energy inductively generated in the antenna 82 by electromagnetic fields imposed on the antenna for the purpose of recharging, by the recharging circuitry, the power source 85 provided within IMD 15A. In the example shown in FIG. 3, anti-migration projections 84 are located adjacent to integrated antenna 82 and protrude away from first major surface 68 to prevent longitudinal movement of the device. In the example shown in FIG. 3 anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 3 header assembly 80 includes suture hole 86, which provides another means of securing IMD 15A to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of IMD 15A.

Figure 4A:
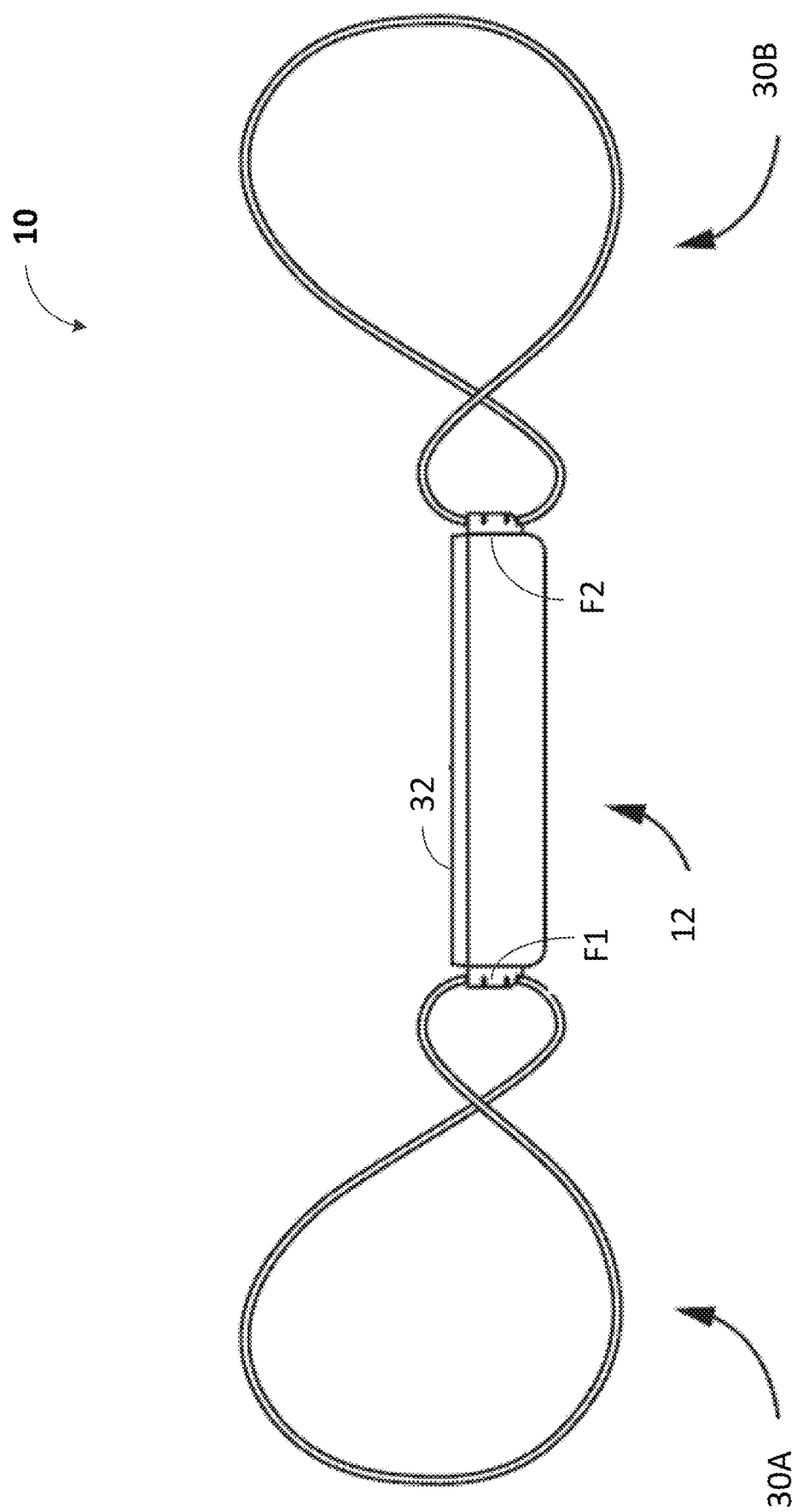
FIGS. 4A and 4B illustrate various views of a pressure sensing device in accordance with examples as described in this disclosure.
Figure 4B:
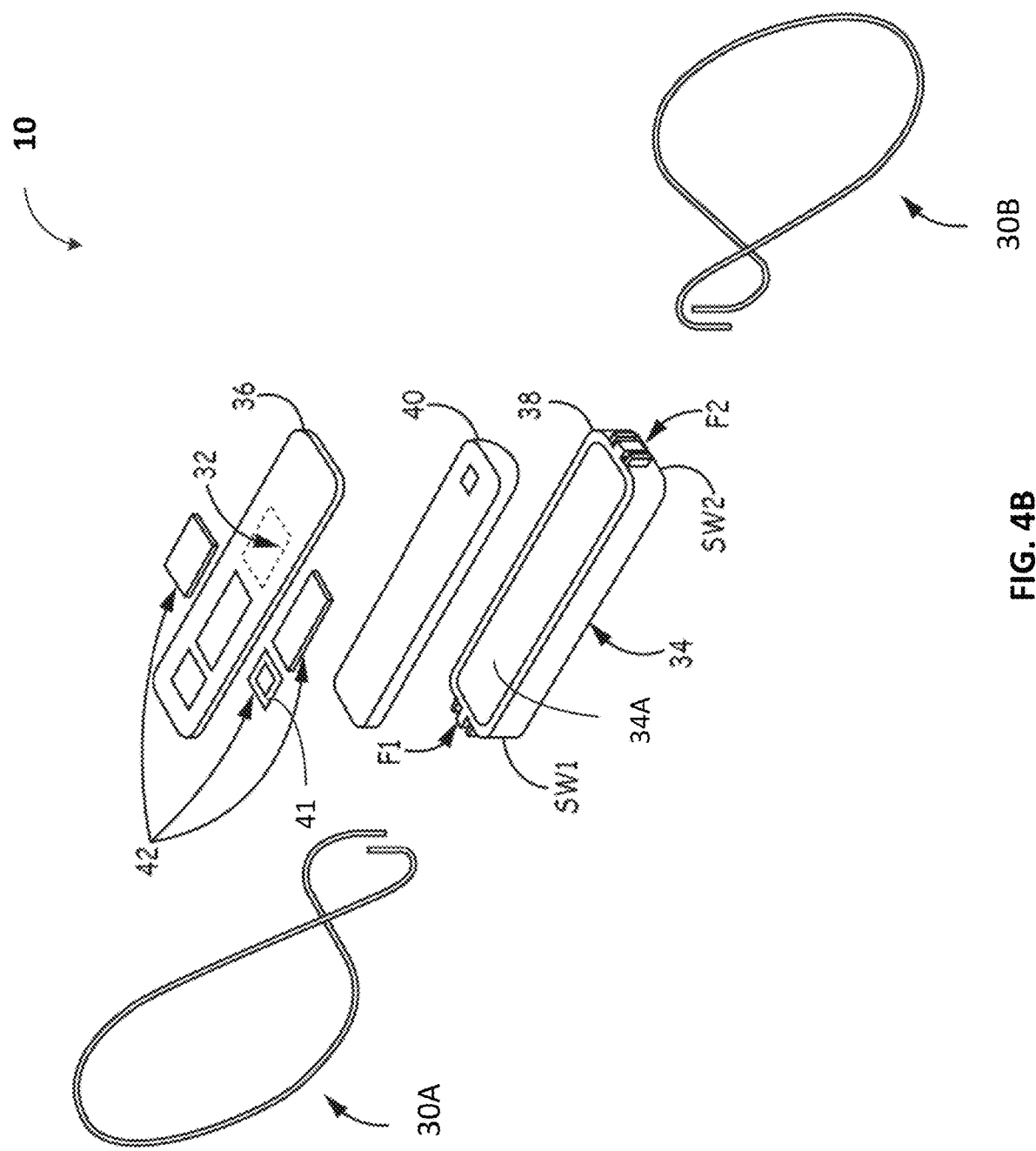

FIGS. 4A and 4B illustrate various views of the pressure sensing device 10 in accordance with examples as described in this disclosure. Pressure sensing device 10 is an example of IMD 15B illustrated in FIG. 1, and is an example of an implantable medical device that may be inductively recharged using the systems, devices, and methods described in this disclosure. As illustrated in FIGS. 4A and 4B, capsule 34 may include an elongate body that defines an interior cavity 34A. The interior cavity 34A of the capsule 34 is sized and shaped to contain the battery 40, and electronics and sensor components 42 of the sensor circuit 12, and an antenna 41 coupled to a communication circuit of the electronic components. In some examples, antenna 41 is a planar antenna designed to save space within IMD 15B, but may also be orientation specific with respect to coupling to electromagnetic and magnetic fields imposed on pressure sensing device 10 for the purpose of inductively recharging battery 40. The capsule 34 is preferably designed with shapes that are easily accepted by the patient's body while minimizing patient discomfort. For example, the body of capsule 34 may be formed in a cylindrical shape with cylindrical sidewalls. In various example, this cylindrical shape of the sidewalls is used to enable a cylindrical recharge/receive coil for inductive power transfer to recharge the power source provided within pressure sensing device 10. Other non-cylindrical configurations may be employed, however, in which case the corners and edges may be designed with generous radii to present a capsule having smoothly contoured surfaces. In the depicted example, the body of capsule 34 is formed as a generally rectangular structure, which means that the outline of the shape of capsule 34 resembles a rectangle with the edges and corners that are contoured.

In some examples, capsule 34 is formed having two sections 36, 38, one of which (e.g., section 36) can contain the sensor element 32, such as a pressure sensing diaphragm, of sensor circuit 12, while the other section (e.g., section 38) can contain the battery 40, and electronics and sensor components 42 of the sensor circuit 12. In some examples, capsule 34 is formed from one or more biocompatible materials that can be hermetically sealed when the sections 36, 38 are joined. A number of such biocompatible materials may be employed, as will be understood by those familiar with the art, including metals and biocompatible plastics. For example, the sections 36, 38 may be formed from unalloyed titanium with an American Society for Testing and Materials (ASTM) grade 1 to grade 4 or an alloyed titanium (grade 5) that includes aluminum and vanadium. or grade 23 ELI (extra low interstitial) or grade 9.

For examples in which the sections are metal, the metal material of the capsule 34 may optionally be selected to be compatible with the fixation assembly 30 material so as to permit the fixation assembly 30A,30B to be securely-coupled to the capsule 34. In other examples, the capsule 34 along with the fixation assembly 30A,30B may be integrally formed from one or more of the same or distinct materials. In some examples, the capsule 34, as well as some portions of the fixation member 30A,30B, may be encapsulated in a biologically inert dielectric barrier material such as a film of silicone or poly(p-xylylene) polymer sold under the trademark PARYLENE.

As shown in FIG. 4B, capsule 34 may include fasteners F1, F2, located on first side wall SW1 and second side wall SW2, respectively, that define channels for reception of a segment of the fixation assemblies 30A and 30B. respectively. The received segment may include a portion along a length of the fixation assemblies 30A,30B, or a free end of the fixation assemblies 30A,30B. The fasteners F1-F2 are coupled to an exterior of the capsule 34, or in alternative examples, formed integrally with the capsule 34. For example, as shown in the example of FIG. 4B, the fasteners F1, F2 are provided at an exterior of the capsule 34 at the lateral sidewalls SW1, SW2, respectively.

In some examples, the fasteners are formed as pairs of tabs that are arranged to define one or more channel(s) for receiving one or more segment(s) of the fixation assemblies 30A,30B. Each fastener can include a pair of tabs that are aligned longitudinally as described, for example, in U.S. Pat. No. 8,864,676 to Beasley et al. which is incorporated herein by reference in its entirety. The fasteners may be coupled to the capsule 34 through welding, for example. Alternatively, the fasteners may be formed integrally with the capsule 34, preferably on opposing ends of the capsule. However, the description of the fasteners F1-F2 is not intended to be limiting, and rather, it is provided to explain the context of the disclosure. In some examples of FIGS. 4A-4B, the fasteners F1-F2 are formed as tubular structures that define channels that are sized to receive a segment of each of the fixation assemblies 30A,30B. In accordance with some examples, the fasteners F1-F2 may be formed as discrete components, such as tubes, for example, that can be coupled to the capsule 34 through coupling techniques such as welding or bonding agent such as glue or crimping. Alternatively, the fasteners may be formed integrally with the capsule 34. The fixation assemblies 30A,30B are coupled to the fasteners F1-F2 by any suitable coupling technique such as welding, crimping, bonding agent such as glue, frictional fit, etc.

The channels of fasteners F1-F2 may optionally be defined to receive a segment of the fixation assemblies 30A,30B in a snug fit arrangement to prevent relative movement between the capsule 34 and the fixation assembly 30. By way of dimensional example, the thickness of a cross section of fixation assemblies 30A,30B may be on the order of 0.006 inch for a round shape or 0.005 inch by 0.010 inch for a rectangular shape. In comparison, the diameter (or width) of the channel of each of the fasteners may be on the order of 0.010 inch to 0.025 inch. The free ends of each of the fixation assemblies 30A,30B may be oriented in opposing directions. For example, a first of the free ends may be oriented downward in relation to the lateral sidewall SW1, SW2, while the other end may be oriented upward in relation to the lateral sidewalls SW1,SW2. Among other things, such an orientation can provide a degree of load cancellation that minimizes load transfer to the sensor element 32.

Figure 5:
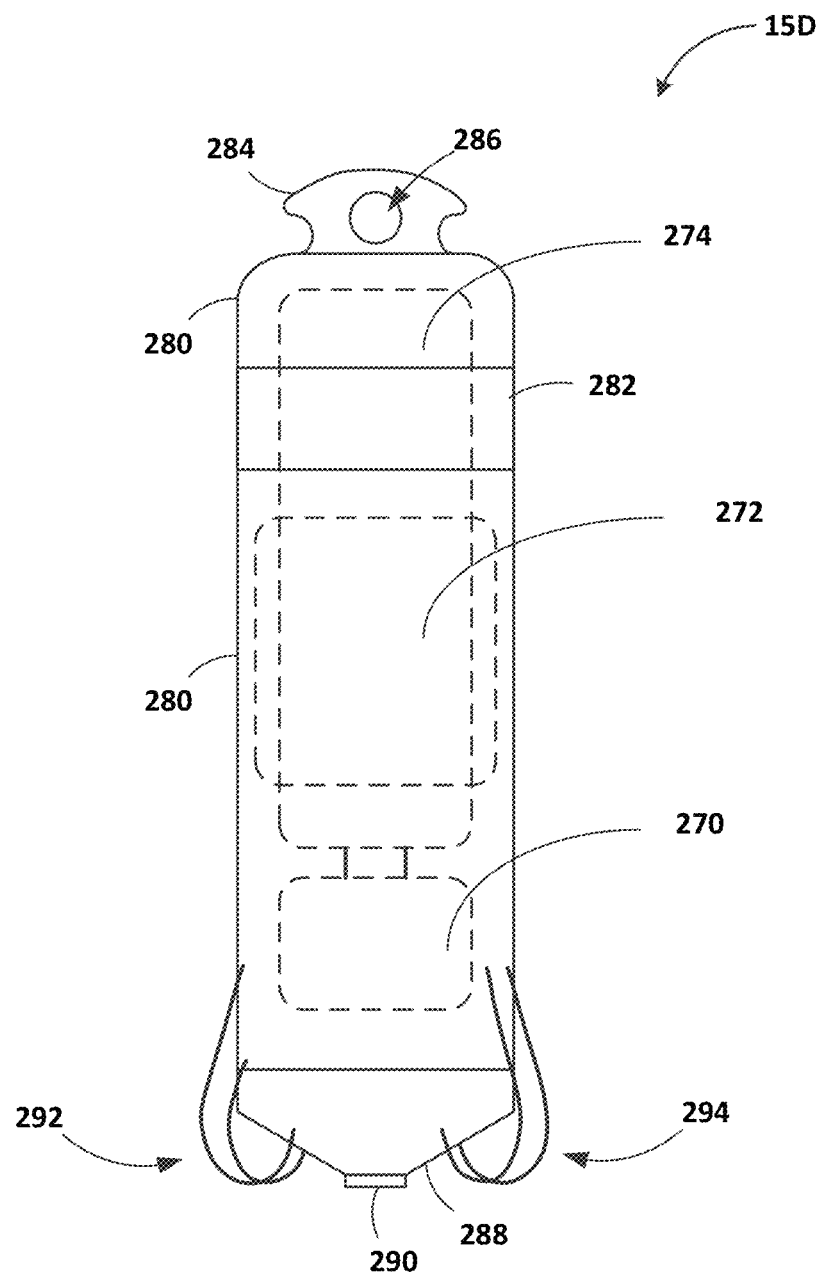
FIG. 5 is an illustrative diagram of an intracardiac pacing device in accordance with examples as described in this disclosure.

FIG. 5 is a diagram of IMD 15D, e.g., an intracardiac pacing device, including a tip electrode 290. In some examples, IMD 15D is a Medtronic® Micra® Transcatheter Pacing System developed by Medtronic, plc, of Dublin, Ireland. IMD 15D may be configured to be implanted in the left ventricle of the heart of a patient, as depicted in FIG. 2. IMD 15D is an example of an implantable medical device that may be inductively recharged using the systems, devices, and methods described in this disclosure. As shown in FIG. 5, IMD 15D includes electronic circuitry 270 including communication circuitry coupled to an antenna 272, and a power source 274, for example a battery, that is coupled to the electronic circuitry and configured to provide power to the electronic circuitry. Communication circuitry of IMD 15D is configured to provide wireless communication between IMD 15 and other devices, such as external device 14. In addition, antenna 272 may be configured to receive electrical energy imposed on IMD 15D as electromagnetic fields, and to recharge battery 274 using energy inductively coupled to antenna 272 from these fields (also known as wireless power transfer). In order to save space and keep IMD 15D as small as possible, antenna 272 may be a planar antenna, such as an antenna formed as a conductive trace on a substrate, or 3-dimensional antenna for example. In various examples, antenna 272 may be orientation sensitive with respect to the orientation of antenna 272 relative to the orientation of the fields imposed on IMD 15D for the purpose of inductive power transfer that can be used for recharging of battery 274, or for directly powering the circuitry within IMD 15D.

IMD 15D includes case 280, cap 288, electrode 290, electrode 282, fixation mechanisms 292 and 294, flange 284, and opening 286. Together, case 280 and cap 288 may be considered the housing of IMD 15D. In this manner, case 280 and cap 288 may enclose and protect the various electrical components, e.g., circuitry, within IMD 15D. Case 280 may enclose substantially all of the electrical components, and cap 288 may seal case 280 and create the hermetically sealed housing of IMD 15D. Although IMD 15D is generally described as including one or more electrodes, IMD 15D may typically include at least two electrodes (e.g., electrodes 282 and 290) to deliver an electrical signal (e.g., therapy such as cardiac pacing) and/or provide at least one sensing vector.

Electrodes 282 and 290 are carried on the housing created by case 280 and cap 288. In this manner, electrodes 282 and 290 may be considered leadless electrodes. In the example of FIG. 5, electrode 290 is disposed on the exterior surface of cap 288. Electrode 290 may be a circular electrode positioned to contact cardiac tissue upon implantation. Electrode 282 may be a ring or cylindrical electrode disposed on the exterior surface of case 280. Both case 280 and cap 288 may be electrically insulating.

Electrode 290 may be used as a cathode and electrode 282 may be used as an anode, or vice versa, for delivering cardiac pacing such as bradycardia pacing, CRT, ATP, or post-shock pacing. However, electrodes 282 and 290 may be used in any stimulation configuration. In addition, electrodes 282 and 290 may be used to detect intrinsic electrical signals from cardiac muscle. Tip electrode 290 may be configured to contact cardiac tissue such as an interior wall of the left ventricle.

Fixation mechanisms 292 and 294 may attach IMD 15D to cardiac tissue. Fixation mechanisms 292 and 294 may be active fixation tines, screws, clamps, adhesive members, or any other mechanisms for attaching a device to tissue. As shown in the example of FIG. 5, fixation mechanisms 292 and 294 may be constructed of a memory material, such as a shape memory alloy (e.g., nickel titanium), that retains a preformed shape. During implantation, fixation mechanisms 292 and 294 may be flexed forward to pierce tissue and allowed to flex back towards case 280. In this manner, fixation mechanisms 292 and 294 may be embedded within the target tissue.

Flange 284 may be provided on one end of case 280 to enable tethering or extraction of IMD 15D. For example, a suture or other device may be inserted around flange 284 and/or through opening 286 and attached to tissue. In this manner, flange 284 may provide a secondary attachment structure to tether or retain IMD 15D within the heart if fixation mechanisms 292 and/or 294 fail. Flange 284 and/or opening 286 may also be used to extract IMD 15D once the IMD needs to be explanted (or removed) from the patient if such action is deemed necessary. IMD 15D is one example of a pacing device configured to include one or more electrodes according to this disclosure. However, other implantable medical devices may be configured to include one or more electrodes similar to those described with respect to IMD 15D.

Figure 6:
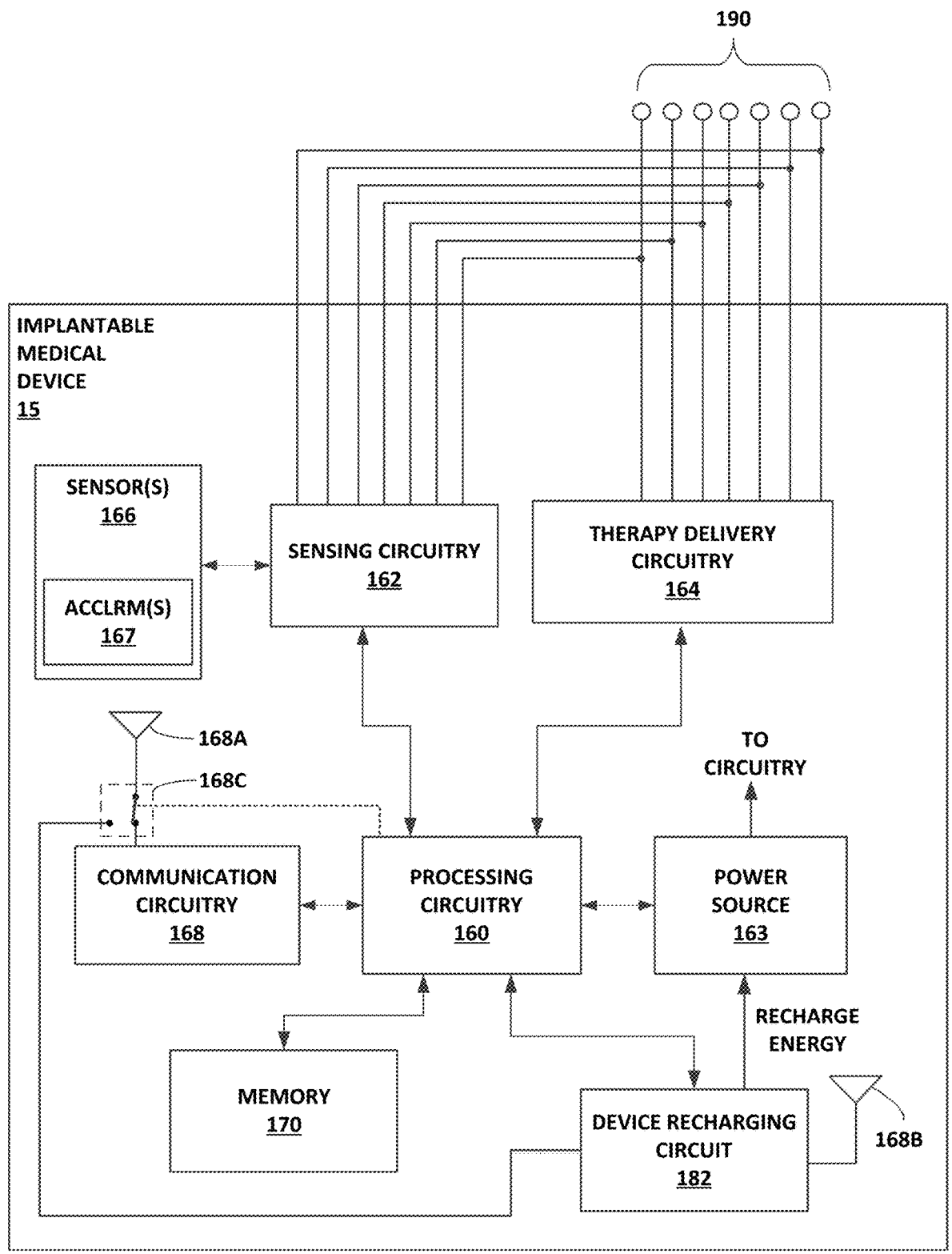
FIG. 6 is a functional block diagram illustrating an example configuration of an implantable medical device according to various examples described in this disclosure.

FIG. 6 is a functional block diagram illustrating an example configuration of an IMD 15 according to various examples described in this disclosure. IMD 15 may correspond to any of IMD 15A and IMD 15B described and illustrated with respect to FIGS. 1, 3, and 4A-4B, IMD 15C and IMD 15D described and illustrated with respect to FIGS. 2 and 5, or another IMD configured to be rechargeable using the devices, systems, and methods as described in this disclosure. IMD 15 includes a power source 163 that may be coupled to the electronic circuitry provided in IMD 15, and is configured to provide electrical power to these circuits. IMD 15 may be inductively rechargeable by providing electromagnetic energy to the IMD 15, wherein energy from these imposed fields may induce an electrical energy into antenna 168A coupled to communication circuitry 168. In addition, antenna 168A is also coupled to device recharging circuit 182. Device recharging circuit 182 is coupled to power source 163, and is configured to receive electrical energy induced in antenna 168A by one or more electromagnetic fields imposed on antenna 168A, and to regulate the energy to provide a level of energy that is provided to power source 163 for the purpose of recharging power source 163.

Device recharging circuit 182 may perform various energy conditioning functions to the energy inductively generated in antenna 168A, for example by providing rectification, voltage level regulation, current level regulation, and/or other signal processing functions in order to generate the "recharging energy" provided to power source 163. However, antenna 168A may be orientation specific with respect to the coupling efficiency of the inductive charging of power source 163 based on the orientation of the antenna 168A relative to the orientation of the coil or coils providing the electromagnetic fields intended to recharge power source 163. Thus, IMD 15 may be configured to couple electromagnetic energy captured by an antenna (including, but not necessarily the telemetry antenna), directed into a suitable rectifying circuit that delivers the electrical energy to an energy storage device such as a rechargeable battery. A switch or transistor 163C may be included in IMD 15B that is controlled to select whether the telemetry or the power recharge system is active, and whether antenna 168A is coupled to the communication circuitry 168 or the device recharging circuit 182.

In the illustrated example, IMD 15 includes processing circuitry 160 and an associated memory 170, sensing circuitry 162, therapy delivery circuitry 164, one or more sensors 166, and the communication circuitry 168 coupled to antenna 168A as describe above. However, IMD 15 need not include all of these components, or may include additional components. For example, IMD 15B may not include therapy delivery circuitry 164 in some examples. Memory 170 includes computer-readable instructions that, when executed by processing circuitry 160, cause IMD 15 and processing circuitry 160 to perform various functions attributed to IMD 15 and processing circuitry 160 herein (e.g., preparing information for transmission from IMD 15 regarding a level of charge present in a power source, such as a battery management system information (BMS), configured to provide information including a state of charge, and/or temperature information related to a battery, e.g., a battery located in IMD 15, determining a level of inductive coupling, e.g., energy level being generated in an antenna located in IMD 15 as a result of an electromagnetic field or fields being imposed on IMD 15 and generating information related to this inductively received energy for transmission by the communication antenna or separate antenna and associated power conditioning circuitry of IMD 15). Memory 170 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media. Memory 170 may store threshold(s) for time of day, posture, heart rate, activity level, respiration rate, and other parameters. Memory 170 may also store data indicating cardiovascular pressure measurements.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162 and therapy delivery circuitry 164 are coupled to electrodes 190. Electrodes 190 illustrated in FIG. 6 may correspond to, for example, electrodes located on leads 20 and 21 of IMD 15C (FIG. 2), proximal electrode 64 and distal electrode 66 of IMD 15A (FIGS. 1 and 3), or electrodes 282 and 290 of IMD 15D (FIG. 5). Sensing circuitry 162 may monitor signals from a selected two or more of electrodes 190 in order to monitor electrical activity of heart, impedance, or some other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190. In some examples, sensing circuitry 162 may sense or detect physiological parameters, such as heart rate, blood pressure, respiration, and other physiological parameters associated with a patient.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

In the example of FIG. 6, IMD 15 includes one or more sensors 166 coupled to sensing circuitry 162. Although illustrated in FIG. 6 as included within IMD 15, one or more of sensors 166 may be external to IMD 15, e.g., coupled to IMD 15 via one or more leads, or configured to wirelessly communicate with IMD 15. In some examples, sensors 166 transduce a signal indicative of a patient parameter, which may be amplified, filtered, or otherwise processed by sensing circuitry 162. In such examples, processing circuitry 160 determines values of patient parameters based on the signals. In some examples, sensors 166 determine the patient parameter values, and communicate them, e.g., via a wired or wireless connection, to processing circuitry 160.

In some examples, sensors 166 include one or more accelerometers 167, e.g., one or more three-axis accelerometers. Signals generated by the one or more accelerometers 167 may be indicative of, as examples, gross body movement (e.g., activity) of the patient, patient posture, heart sounds or other vibrations or movement associated with the beating of the heart, or coughing, rales, or other respiration abnormalities. Accelerometers 167 may produce and transmit signals to processing circuitry 160 for a determination as to in the posture of the patient. In various examples, signals from the accelerometers 167 are processed to determine an activity, such as when the patient is taking a step or steps, or for example when the patient is running, used to provide an activity count associated with patient initiated physical activity of the patient. In some examples, sensors 166 may include sensors configured to transduce signals indicative of blood flow, oxygen saturation of blood, or patient temperature, and processing circuitry 160 may determine patient parameters values based on these signals. In various examples, sensors 166 may include one or a combination of sensors 19 as previously described.

In some examples, processing circuitry 160 determines one or more patient parameter values based on pressure signals. Patient parameter values determined based on pressure may include, as examples, systolic or diastolic pressure values, such as pulmonary artery diastolic pressure values. In some examples, a separate device such as sensor circuits 19 include one or more sensors and sensing circuitry configured to generate a pressure signal, and processing circuitry 160 determines patient parameter values related to blood pressure based on information received from IMD 15.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

Communication circuitry 168 includes any suitable hardware, firmware, software or any combination thereof for communicating with another device, such as an external device 14, transceiver 24, or another IMD or sensors, such as sensor circuits 19, as shown in FIG. 1 and FIG. 2. Under the control of processing circuitry 160, communication circuitry 168 may receive downlink telemetry from and send uplink telemetry to external device 14 or another device with the aid of an antenna, which may be internal and/or external. In some examples, communication circuitry 168 may communicate with a local external device, for example through transceiver 24, and processing circuitry 160 may communicate with a networked computing device via the local external device and a computer network, such as the Medtronic® CareLink® Network developed by Medtronic, plc, of Dublin, Ireland. In some examples (i.e. where a single antenna is used) the antenna signal can be switched from the telemetry communication circuitry to the recharge circuit. In other examples the recharge antenna/coil is separate from the communication/telemetry antenna. For example, antenna 168A may be switched between being coupled to communication circuitry 168 and device recharging circuit 182 by switch 168C, wherein switch 168C may be controlled by processing circuitry 160 to determine when antenna 168A is coupled to the communication circuitry 168 and when antenna 168A is to be coupled to the device recharging circuitry 182. In other examples, a second antenna 168B is coupled to device recharging circuitry 182, and is configured to receive inductively coupled energy provided to antenna 168B, and to provide the inductively coupled energy to device recharging circuit 182 to recharge power source 163.

In various examples, processing circuitry 160 is coupled to device recharging circuit 182, and receives information, such as a level of current, that is being induced in antenna 168A or antenna 168B as a result of electrical energy received by the antenna via electromagnetic energy imposed on IMD 15 for the purpose of recharging power source 163. Processing circuitry 160 may provide this and other information, for example charge rate and temperature information associated with the power source 163, in the form of an output signal to communication circuitry 168 for transmission from IMD 15 to one or more external devices, such as transceiver 24. This transmitted information may be used by the external device(s) to control one or more aspects of the recharging process. For example, positioning and/or orientation of one or more sets of coils located externally to IMD 15 and generating the electromagnetic fields imposed on IMD 15 may be controlled using this information transmitted from IMD 15. In addition, other information such as temperature and field intensity information transmitted from IMD 15 may be used to control the recharging process, for example by regulating the field strength being generated by the external coils, or for example to shut off the external coils to stop the recharging process.

A clinician or other user may retrieve data from IMD 15 using external device 14 or another local or networked computing device configured to communicate with processing circuitry 160 via communication circuitry 168, for example through a transceiver such as transceiver 24. The clinician may also program parameters of IMD 15 using external device 14 or another local or networked computing devices. In some examples, the clinician may select patient parameters used to determine times of day and target activity levels to determine when to trigger taking cardiovascular pressure measurements.

In various examples, processing circuitry 160 is configured to receive signals from sensing circuitry 162, sensors 166, and or sensor signal provided by sensors external to IMD 15, to process these sensor signals to generate one or more input parameters based either directly on or derived from the sensor signals. The input parameters are associated with current value(s) for one or more physiological parameters associated with a patient, such as patient 2A or 2B. The physiological parameters associated with the input parameters may include activity counts, respiration rates, breathing rates, movements, postures, and changes in postures associated with a patient. The current values associated with these input parameters can be values measured directly from the input parameters, or derived for these input parameters. For example, a value of a heartrate, measured for example in heartbeats per minute or cardiac cycle length, may be determined as the current value (e.g., the most recent value) for the input parameter associated with the heart rate of the patient measured over some predefined time period. Similarly, a value of a breathing rate, measured for example in breaths per minute or breathing cycle length, may be determined as the current value (e.g., the most recent value) for the input parameter associated with the breathing rate of the patient as measured over some predefined time period. Similarly, current values can be determined for other input parameters, such as activity count (e.g., based on movement of the patient measured for example in steps taken by the patient per minute), body temperature, and for example a current value for a posture of the patient (e.g., lying down, standing, sitting). A current value of a physiological parameter may be, in some examples, a mean or median of measured values over a period of time.

Figure 7A:
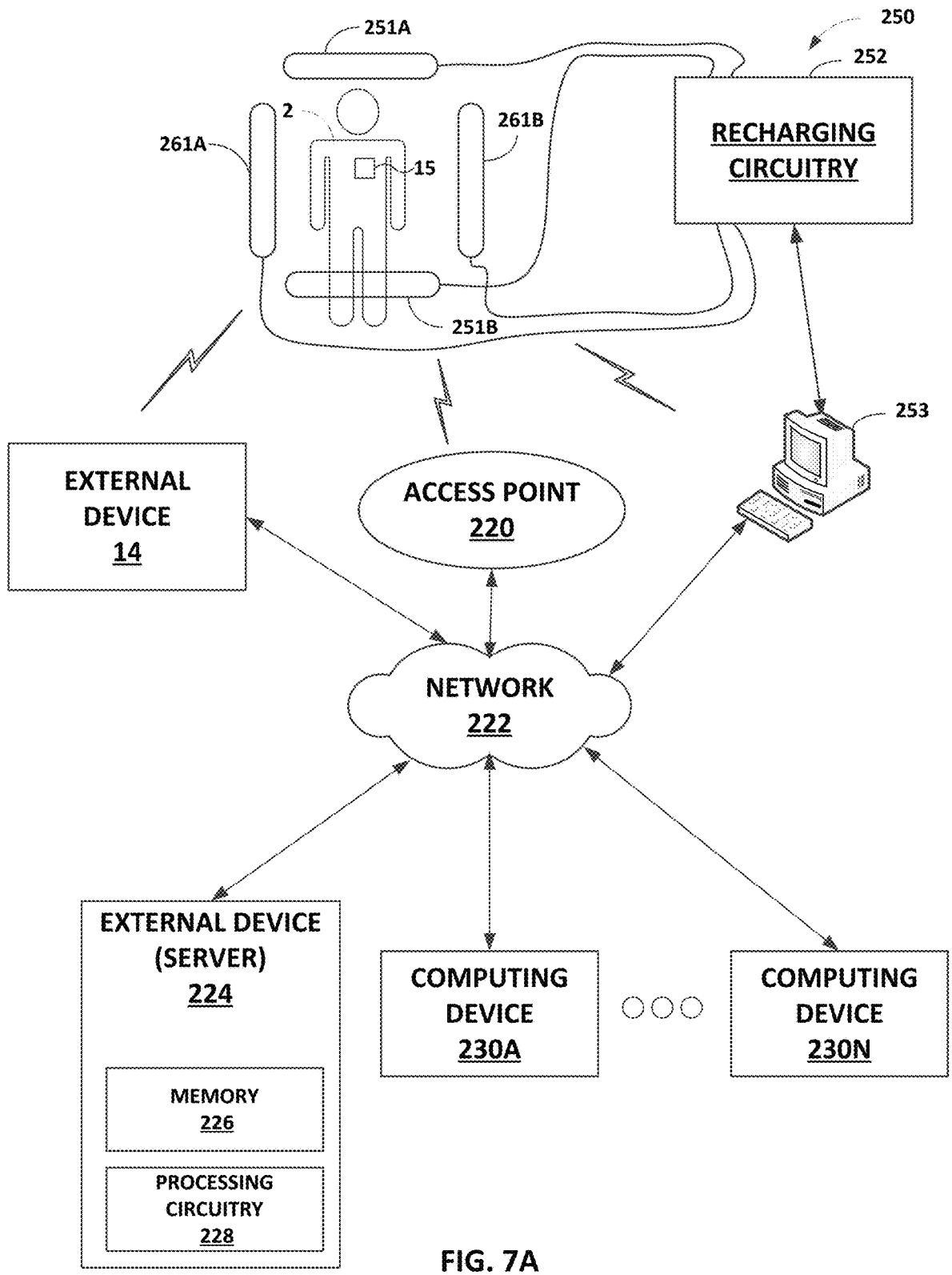
FIG. 7A is a functional block diagram illustrating an example inductive recharging system including recharging circuitry that is electrically coupled to a first pair of coils and a second pair of coils according to various examples described in this disclosure.

FIG. 7A is a functional block diagram illustrating an example inductive recharging system 250 including power transmission recharging circuitry 252 electrically coupled to a first pair of coils 251A/251B, and a second pair of coils 261A/261B, all located externally to a patient 2, according to various examples described in this disclosure. In some examples, coils 251A/251B are configure to operate as a Helmholtz coil, and coils 261A/261B are also configured to operate as a Helmholtz coil. When energized, the coils are configured to provide a time-varying and spatially uniform, electromagnetic field that may be imposed on an implanted medical device, such as IMD 15 illustratively represented as being implanted in patient 2, for the purpose of recharging a power source within IMD 15. Recharging circuitry 252 may be coupled to a computer 253 that includes a display and one or more input devices, such as a keyboard and/or a computer mouse, that allow a user to interact with recharging circuitry 252, and that can apportion the relative intensities of the electromagnetic field in such a way as to steer the direction of the peak magnetic field intensity, thus maximizing the power transfer to a single receive coil (e.g., a recharging antenna) located within IMD 15 that is positioned in the electromagnetic field generated by the coils of the recharging system. Further, feedback received from IMD 15, for example received by computer 253, may be used to control and adjust various aspects of recharging circuitry 252, including physically adjusting the positioning of one or more pairs of the electrical coils 251/261 based on the feedback provided by IMD 15. For example, the set of electrical coils 261A/261B may be configures so that the position of the coils can be moved, for example rotated around the central axis running between coils 251A/251B, in order to steer the direction of the resultant magnetic field imposed on the receive coil of the recharging circuitry located within IMD 15, and thus maximize the inductive coupling and the power transfer provided to the receive coil and the recharging circuitry of IMD 15. Feedback from IMD 15 in some examples comprises a value for the level of current that is being induced in the receive coil of IMD 15 through the inductive coupling of the energy being provided by coils 251A/251B and coils 261A/261B. Other information provided by IMD 15, such as temperature, rate of charge, and percentage of charge information generated by IMD 15 may be transmitted from IMD 15 to computer 253 or other external devices, and use by recharging circuitry 252 to control and/or to determine when to terminate the recharging process being performed on IMD 15.

System 250 further includes external computing devices, such as a server 224 and one or more other computing devices 230A-230N, that are coupled to IMD 15, and external device 14 via a network 222. In this example, IMD 15 may use its communication circuitry 168 to, e.g., at different times and/or in different locations or settings, to communicate with external device 14 via a first wireless connection, and to communicate with an access point 220 via a second wireless connection. In the example of FIG. 7A, computer 253, access point 220, external device 14, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with the patient. Access point 220 may interrogate IMD 15, e.g., periodically or in response to a command from the patient or network 222, to retrieve physiological measurements and/or other operational or patient data from IMD 15. Access point 220 may provide the retrieved data to server 224 via network 222. In various examples, access point 220 may be any example of transceiver 24 described above.

In some cases, server 224 may be configured to provide a secure storage site for data that has been collected from IMD 15, and/or from external device 14. In some cases, server 224 may assemble data in web pages or other documents for viewing by trained professionals, such as clinicians, via computing devices 230A-230N. The illustrated system of FIG. 7A may be implemented, in some aspects, with general network technology and functionality similar to that provided by the Medtronic® CareLink® Network developed by Medtronic plc, of Dublin, Ireland.

In some examples, one or more of access point 220, server 224, or computing devices 230A-N may be configured to perform, e.g., may include processing circuitry configured to perform, some or all of the techniques described herein, e.g., with respect to processing circuitry 160 of IMD 15 and external device 14, relating to the recharging of power source located within IMD 15. In the example of FIG. 7A, server 224 includes a memory 226 to store physiological and other data received from IMD 15 and/or external device 14, and processing circuitry 228, which may be configured to provide some or all of the functionality ascribed to processing circuitry 160 of IMD 15 as described herein. For example, processing circuitry 228 provide programming and/or parameters that are used by recharging circuitry 252 in process of providing inductive recharging to a power source located within IMD 15. Configurations for and operational features of coils 251A/251B, 261A/261B and recharging circuitry 252 are further described with respect to FIGS. 7B-7D, FIGS. 8A-C, FIGS. 9-11 and 12A-B of this disclosure.

Figure 7B:
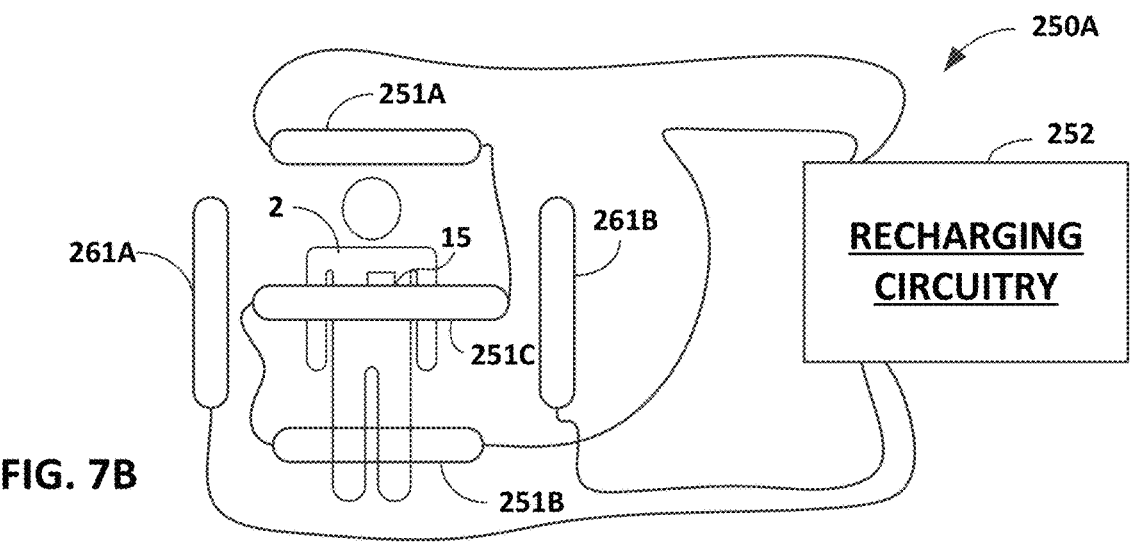
FIGS. 7B-7D are functional block diagrams illustrating variations of the inductive recharging system of FIG. 7A according to various examples described in this disclosure.
Figure 7C:
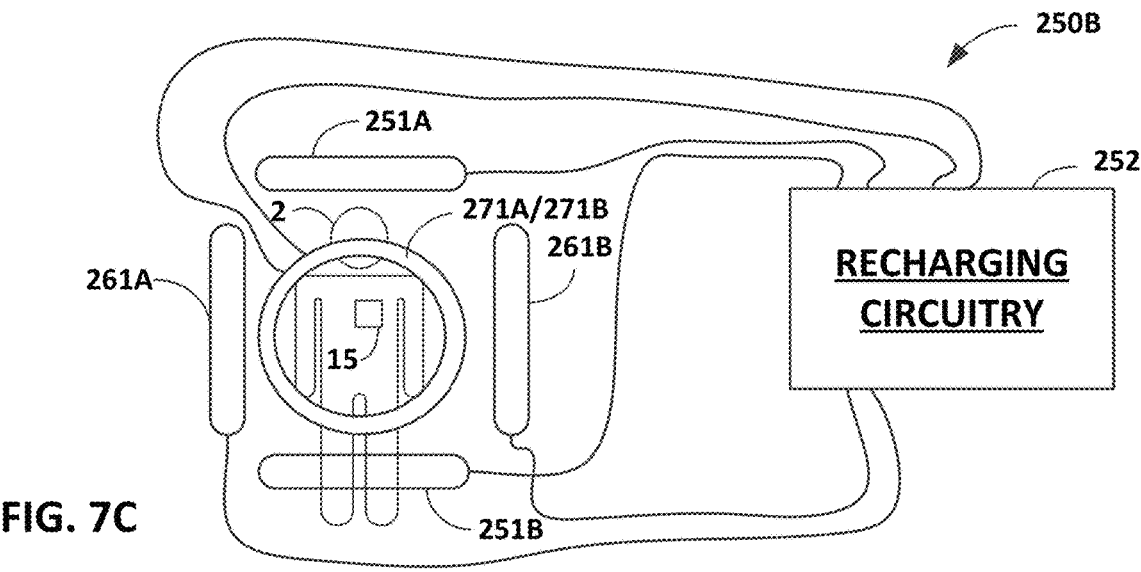
Figure 7D:
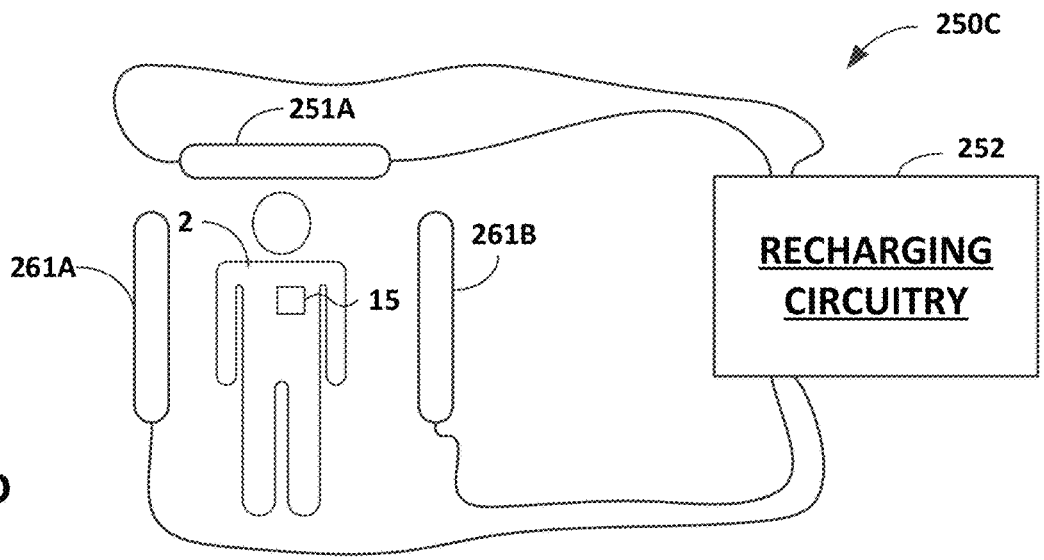

FIGS. 7B-7D are a functional block diagrams illustrating variations of the indicative recharging system of FIG. 7A according to various examples described in this disclosure.

FIG. 7B is a functional block diagram illustrating an example variation of an inductive recharging system 250A including power transmission recharging circuitry 252 electrically coupled to a first set of electrical coils 251A/251B/251C, and a second pair of electrical coils 261A/261B, all located externally to patient 2, according to various examples described in this disclosure. As illustrated in FIG. 7B, the first set of coils 251A/251B/251C comprises a pair of coils 251A/251B, and a third electrical coil 251C arranged in a position between electrical coils 251A and 251B. In some examples, the coils 251A, 251B, and 251C are arranged to form a Maxwell coil, as further illustrated and described below with respect to FIG. 8C. The magnetic field provided by the three-coil arrangement may be even more uniform within the region of the magnetic field provided between coils 251A/251B than would be obtainable using a two-coil only arrangement. The second pair of coils 261A/261B are arranged to the left and right sides, respectively, of patient 2 and having a central axis perpendicular to a central axis of the first pair of coils 251A/251B. In FIG. 7B, the second pair of coils 261A/261B may be arranged as a Helmholtz coil. In various examples, the second pair of coils 261A/261B may be configured to be physically moveable, as described above, to reposition coils 261A/261B to maximize the inductive coupling provided by the resultant magnetic field imposed on the receive coil and the recharging circuitry located within IMD 15 when coils 251A/251B/251C and 261A/261B are electrically energized by recharging circuitry 252. Recharging circuitry 252 may provide any and all of the functions described above with respect to inductive recharging system 250, except using the three-coils arrangement of electrical coils 251A/251B/251C.

FIG. 7C is a functional block diagram illustrating an example variation of an inductive recharging system 250B including power transmission recharging circuitry 252 electrically coupled to a first set of electrical coils 251A/251B, a second pair of electrical coils 261A/261B, and a third pair of electrical coils 271A/271B, all located externally to patient 2, according to various examples described in this disclosure. As illustrated in FIG. 7C, the first pair of coils 251A/251B are arranged above and below patient 2, the second pair of coils 261A/261B are arranged to the left and right sides, respectively, of patient 2 and having a central axis perpendicular to a central axis of the first pair of coils 251A/251B, and a third pair of coils 271A/271B are arranged over and underneath the patient 2, the third pair of coils 271A/271B having a central axis perpendicular to both the central axis of the first pair of coils 251A/251B and perpendicular to the central axis of the second pair of coils 261A/261B. As shown in FIG. 7C, the second coil 271B is not visible in the drawing as it is located underneath patient 2 and directly below coil 271A, wherein coil 271A is over the patient 2 as viewed in FIG. 7C.

In various examples, one or more of the first, second, and/or the third pairs of coils is/are configured as Helmholtz coils. In various examples, the energization of the first, second, and third pairs of coils as illustrated in FIG. 7C may be controlled by recharging circuitry 252 to maximize the inductive coupling efficiency provided by the resultant magnetic field imposed on the receive coil and the recharging circuitry within IMD 15. In various examples, by using three sets of coils as illustrated in FIG. 7C, the need to move or reposition one or more of these pairs of coils may be eliminated while still being able to provide maximum inductive coupling efficiency to the receive antenna and the recharging circuitry of IMD 15. Recharging system 250B may provide any and all of the functions described above with respect to inductive recharging system 250, except using the three coils arrangement of electrical coils 251A/251B, 261A/261B, and 271A/271B.

FIG. 7D is a functional block diagram illustrating an example variation of an inductive recharging system 250C including power transmission recharging circuitry 252 electrically coupled to a first coil 251A, operating as a singular coil, and a pair of electrical coils 261A/261B, all located externally to patient 2 according to various examples described in this disclosure. As illustrated in FIG. 7D, the first coil may be arranged above patient 2, and the pair of coils 261A/261B are arranged to the left and right sides, respectively, of patient 2 having a central axis perpendicular to a central axis of the first coil 251A. As shown in FIG. 7D, the pair of coils 261A/261B may be arranged as a Helmholtz coil. In various examples, coil 251A and/or the pair of coils 261A/261B may be configured to be physically moveable relative to patient 2 and IMD 15 to increase the inductive coupling provided by the resultant magnetic field imposed on the receive coil and the recharging circuitry within IMD 15. However, the level of control, and thus the ability to maximize the inductive coupling to the receive coil and to the recharging circuitry of IMD 15 using the arrangement as illustrated in FIG. 7D may be limited and less effective in achieving and controlling the level of inductive coupling that may be provided by other arrangements and techniques described in this disclosure.

Figure 8A:
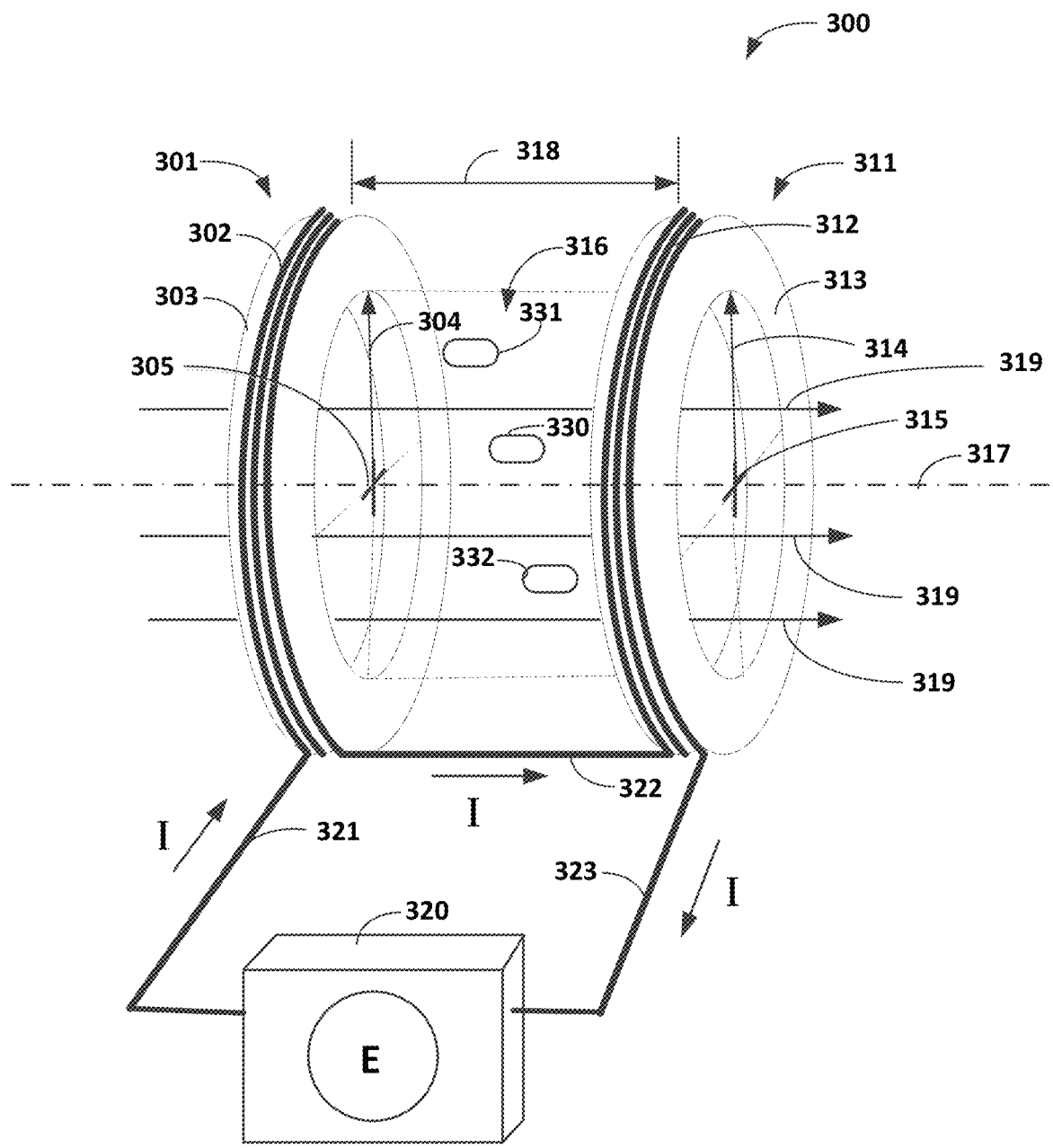
FIG. 8A illustrates a system including an example pair of coils according to various examples described in this disclosure.

FIG. 8A illustrates a system 300 comprising an example pair of coils 301 and 311 in accordance with example implementations and techniques described in this disclosure. In some examples, coils 301 and 311 are configured to form a Helmholtz coil, although examples of coils 301 and 311 are not limited to being configured to specifically form a Helmholtz coil. As illustrated, coil 301 includes a winding 302 comprising a length of an electrical conductor wound onto a winding support structure 303. Support structure 303 supports the winding 302 in a circular configuration located around a center point 305 of the support structure 303, wherein the winding 302 is located at a distance surrounding the center point 305 at a radius 304, or within a first distance and a second distance (e.g., a thickness of the winding 302 relative center point 305) substantially within a small variation of distance around the radius 304. In a substantially same manner, coil 311 includes a winding 312 comprising a same length of an electrical conductor as provided for winding 302. Winding 312 is wound onto a winding support structure 313. Support structure 313 supports the winding 312 in a circular configuration located around a center point 315 of the support structure 313, wherein the winding 312 is located at a distance surrounding the center point 315 at a radius 314, or within a first distance and a second distance (e.g., a thickness of the winding 312 relative to center point 315) substantially contained within a small variation around the radius 314. The radius 314 of coil 311 has a same radial dimension as the radial dimension for radius 304 of coil 301. Coil 301 including winding 302 and coil 311 including winding 312 have center points 305, 315 that lie in separate planes that are parallel to each other, and with a central axis 317 passing through both center point 305 and center point 315 that is perpendicular to each of these separate planes. A distance 318 separates these parallel planes and coils 301 and 311 along any given point of the windings 302, 312. Distance 318 may be set so that distance 318 has a dimensional value that is equal to the dimensional value of each of radius 304 of coil 302 and also equal to the dimensional value of radius 314 of coil 311.

In FIG. 8A, a first electrical conductor 321 is coupled to a first end of the electrical conductor forming winding 302 of coil 301, and may be coupled to a source of electrical energy, such as source 320 as shown in FIG. 8A at the opposite end of conductor 321. A second end of winding 302 is coupled to a first end of a second electrical conductor 322. The second end of electrical conductor 322 is coupled to a first end of the electrical conductor forming winding 312. A second end of winding 312 is coupled to a first end of a third electrical conductor 323. The second end of electrical conductor 323 is coupled to source 320. As such, the winding 302 is electrically coupled in series with winding 312. When coupled to source 320 as illustrated in system 300, source 320 may provide a current I to conductor 321, which would be conducted through winding 302 of coil 301, through electrical conductor 322 to winding 312 of coil 311, and through conductor 323 back to source 320, completing the electrical circuit allowing a flow of current "I" as described. As such, a same level of current "I" flows through both winding 302 and winding 312 as provided by source 320 at any given time. In various examples, source 320 may include an oscillator, a power amplifier, and a suitable matching network to suitably drive the Helmholtz pair of coils 301, 311, as further illustrated and described with respect to FIGS. 12A and 12B.

As shown in FIG. 8A, when energized by the flow of current "I," each of coils 301 and 311 will generate an electromagnetic field, including a magnetic field, surrounding winding 302 and 312, respectively, as would be understood by one of ordinary skill in the art. Further, when coils 301 and 311 are arranged as shown in FIG. 8A and as described above are provided with a flow of current "I" in the manner described above, coils 301 and 311 form what is referred to as a Helmholtz coil. A pair of coils such as coils 301 and 311 arranged as Helmholtz coils provides a unique property in the that intensity of the magnetic (electromagnetic) field within a cylindrical region between the two coils, generally indicated by arrow 316, is relatively uniform field in magnitude and in direction within the cylindrical region. In other words, a strength of the electromagnetic field provided by the Helmholtz coil within the cylindrical region 316 is consistently of the same strength throughout the volume provided within the cylindrical region 316. This consistent magnetic field is illustratively represented by the arrows 319 in FIG. 8A. As used throughout this disclosure, a "uniform field" refers to a magnetic field having no more than approximately a seven percent variation in the magnitude of the field within the cylindrical region as described above, and having a uniform direction.

As such, when using the time varying magnetic field generated by coils 301 and 311 to provide energy to an implanted medical device for the purpose of charging a power source located within the implanted medical device, the location of the device relative to position within the cylindrical region 316 does not have a substantial effect or result in significant variation with respect to the strength of the magnetic field imposed on the device. For example, illustrative implanted medical devices 330, 331, and 332 are located at different positions with the cylindrical region 316 between coils 301 and 311. These different positions could be illustrative of implanted medical devices located at different implantation sites and/or at different implantation depths of a patient. However, as long as any of the implanted medical devices 330, 331, and 332 remain located within the cylindrical region 316 generated between coils 301 and 311, the strength of any magnetic field generated by coils 301, 311 imposed on these devices will be substantially the same throughout cylindrical region 316, and thus would impose substantially a same strength magnetic fields on each of the devices 330, 331, 332 despite the variation in the locations of these devices within the cylindrical region 316. By providing the uniform magnetic field 319 within the cylindrical region 316, coils 301, 311 may be used to provide, at least in part, a magnetic field that may be used to provide inductive type charging of implanted medical device, such as devices 330, 331 and 332, without specific regard to the relative position of the device being charged with respect to height or relative proximity to coils 301 and 311 of the device as long as the device remains within the cylindrical region 316, since as described above the strength of the magnetic field is substantially consistent throughout the space represented by the cylindrical region 316. The remaining variable with respect to the coupling of the magnetic field provided by coils 301 and 311 to a planar (or coiled) antenna with the implanted medical device is the relative orientation of the planar (or coiled) antenna of the device to be inductively charged relative to center axis 317. For example, if a suitable coil planar antenna lies parallel to the planes where coils 301 and 311 lie, the coupling of the magnetic energy will be maximum. However, if the planar axis of the antenna of the implanted medical device lies in a plane that is perpendicular to the planes where coils 301 and 311 lie, the coupling of the magnetic energy will be very poor or substantially null. Analogously, a coiled receive antenna will facilitate maximum coupled power transfer when the receive coil intercepts the maximum flux of magnetic field intensity, i.e. when the receive coil is parallel to the single Helmholtz pair. Note this constraint can be relieved by steering the direction of the magnetic field intensity using for example orthogonal Helmholtz pairs of coils.

This remaining orientation problem may be solved by providing a second Helmholtz coil having a central axis that is orthogonal to central axis 317 of coils 301 and 311, and having a cylindrical region associated with the second Helmholtz coils that overlaps the cylindrical region 316 of coils 301 and 311. By adjusting the strengths of the magnetic fields of each of a pair of Helmholtz coils providing a magnetic field in the overlapping area or overlapping region of magnetic fields, and by adjusting at least one of the pair of Helmholtz coils by rotating the at least one Helmholtz coil around the central axis of the second Helmholtz coil while keeping the central axes orthogonal to each other, an effective level of coupling between the resultant magnetic fields and the planar antenna of the medical device to be charged may be achieved. These "overlapping" regions and the resultant magnetic fields obey the superposition principle, that is, the orthogonal magnetic fields add as vectors, summing to a resultant magnetic field with a single intensity and direction based on the vector sum. These magnetic fields provided within the overlapping regions of magnetic fields within an area common to both the first cylindrical region and the second cylindrical region may be referred to as a "resultant magnetic field" throughout the remainder of the disclosure. Because of the consistency of the magnetic fields that may be generated and controlled by arranging the first and second coils, in some examples Helmholtz coils as described in this disclosure, and by controlling the current provided to each of the first and second coils, in some examples Helmholtz coil, as further described this disclosure, efficient charging of power sources within deeply implanted and/or small implanted medical devices may be accomplished using levels of magnetic fields strengths that are deemed to be safe for the patient.

In various examples, each coil used to form a Helmholtz coil in the recharging systems of the examples provided herein may have radius in a range of 10 to 30 inches (25.4 to 76.2 centimeters), and a spacing between the coil equal to the radius, thus in a range of 10 to 30 inches 25.4 to 76.2 centimeters). In various examples, the radius of the Helmholtz coils is approximately 15.4 inches (i.e., 39.0 centimeters). In various examples, each of coils 301, 311 provide a DC resistance in a range of 100 to 5,000 mΩ, or a self-resonant frequency of 500 to 3,000 kHz. In various examples, the electrical energy provided by source 320 to energize coils 301, 311 comprises a time modulated signal that can be a sine/cosine, square wave, sawtooth or another waveform. In various examples, an oscillator providing the time-modulated signal is coupled to a power amplifier, the output of the power amplifier is routed through a matching network to the Helmholtz pair. The matching network maximizes the power transfer to the transmit coil by minimizing voltage/current reflection. The power delivered to the load (i.e. Helmholtz pair) may be between 100 and 400 W. The corresponding peak current in some examples is between 5 and 15 amperes. The peak voltage across the coil can be as high as 40 kV. The voltage wave in some examples is largely out of phase with the current wave. In various examples, the electrical energy provided to the coils 301, 311 is determined in conjunction with the electrical parameter associated with the coils to provide a uniform magnetic field intensity in region 316 in a range of 50 to 1,000 A/m, and not to exceed a preterminal values, for example not to exceed a value of 1,500 A/m for the safety of the patient.

Figure 8B:
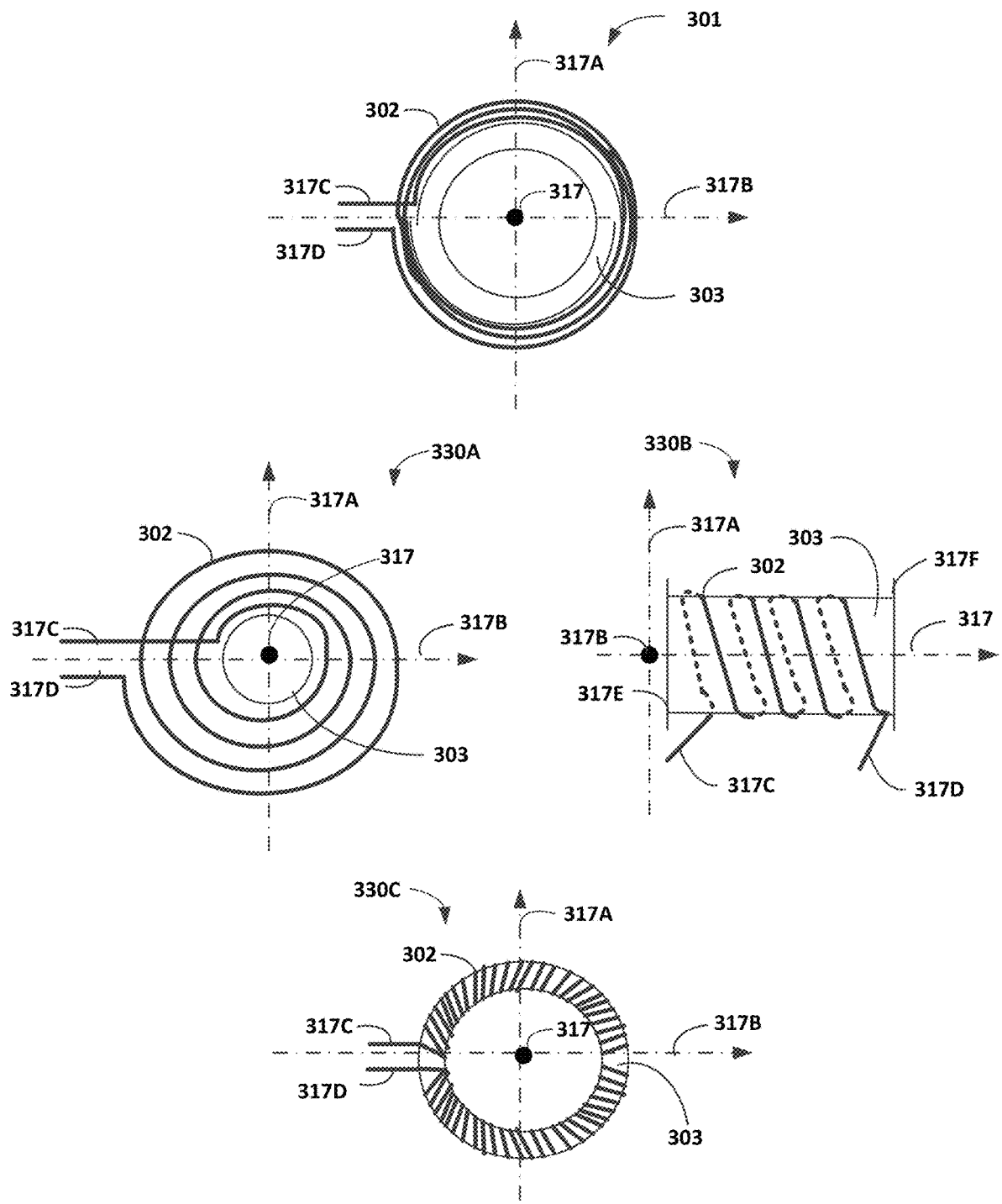
FIG. 8B illustrates various examples of winding techniques for the electrical coils according to various examples described in this disclosure.

FIG. 8B illustrates various examples of winding techniques that may be used to construct one or more of the electrical coils for use in the recharging systems described in this disclosure. Coil 301 is illustrated in FIG. 8B for illustrative purposes, having the central axis 317 of coil 301 turned so that central axis 317 as viewed in FIG. 8B is orientated directly into the plane of the drawing sheet, perpendicular to both an X axis 317A and a Y axis 317B that are substantially coplanar with the winding 302 of coil 31, and perpendicular to each other. Details 330A, 330B, and 330C will now be described using these axes of coil 301 for orientation purposes relative to the views illustrated in these details. Detail 330A is an illustrative example of the electrical conductor 302 being "flat-planar wound" around the perimeter of support structure 303 to form coil 301. As shown in detail 330A, each layer of the winding of conductor 302 is wound so that all windings are coplanar relative to one another, and starting at the first input lead 317C having an initial winding closest to central axis 317. The additional winding of conductor 302 are formed around and surrounding the initial winding closest to first input lead 317C, and form a spiral shape having an increasing larger distance from the central axis 317 as each winding is added to coil 302, extending to second input lead 317D.

Detail 330B is an alternative example illustrating electrical conductor 302 being spiral wound to form a solenoid type winding around support structure 303. As shown in detail 330B, first input lead 317C of conductor 302 is wound near one end 317E of the support structure 303, and consecutive windings are formed along support structure 303 in a direction along central axis 317 toward a second end 317F of support structure 303 so that each of the windings of conductor 302 formed between first input lead 317C and second input lead 317D are substantially a same distance away from central axis 317. In some examples, a combination of the winding techniques of detail 330A and 330B may be used. For example, a first layer of windings of conductor 302 may be formed as a solenoid type winding as shown in detail 330B, and then another layer of windings formed above the first layer of winding 302, in a manner similar to that shown in detail 330A, forming layers of windings, but wherein each layer includes a plurality of windings of conductor 302 wound in a solenoid type winding. In various examples, the total number of these layers of solenoid type windings formed as one set of windings surrounding another set of windings is not limited to any particular number of layers of windings, and may include a plurality of layers forming coil 301.

Detail 330C illustrates an example of coil 301 formed using a spiral or helical winding of conductor 302. As illustrated in detail 330C, conductor 302 is wound around winding support structure 303 in a set of loops, each loop including a portion of the conductor 302 that is located on the outside of winding support structure 303 at a point farthest away from central axis 317, and a portion of conductor 302 that is located outside winding support structure 303 at a point closest to central axis 317 to form a toroid-shaped winding. Conductor 302 as wound using the configuration as illustrated in detail 330C includes the series of winding formed between the first input lead 317C and the second input lead 317D. In various examples, multiple layers of these spiral winding maybe formed, each layer wound around an existing layer, to form multiple layers of spiral windings.

In various examples, the electrical conductor 302 used to wind coil 301 is Litz wire, for example a single or multiple stranded wire, wherein the conductor 302 is insulated along the outer surface for example using a coating, such as enamel, to reduce the skin effect of the electrical conductor. Skin effect is the characteristic of electrical current flowing through an electrical conductor that causes the flow of current in the electrical conductor to travel though the outer portion, e.g., the "skin" of the conductor, and not through the inner portion of the electrical conductor. The skin effect is more pronounces at higher frequencies. The use of Litz wire helps reduce the skin effect in the electrical conductor 302 at higher frequencies. In addition, the inter-turn capacitance of the respective windings/turns is reduced by increasing inter-turn distances, thus increasing the self-resonant frequency of the assembly and enabling higher modulation frequency to be applied to the coil.

Any of the windings illustrated in details 330A, 330B, and 330C, and other winding techniques as would be understood by one of ordinary skill in the art, are contemplated for use in forming coils 301, 311 and may be used in forming any other examples of coils described throughout this disclosure.

Figure 8C:
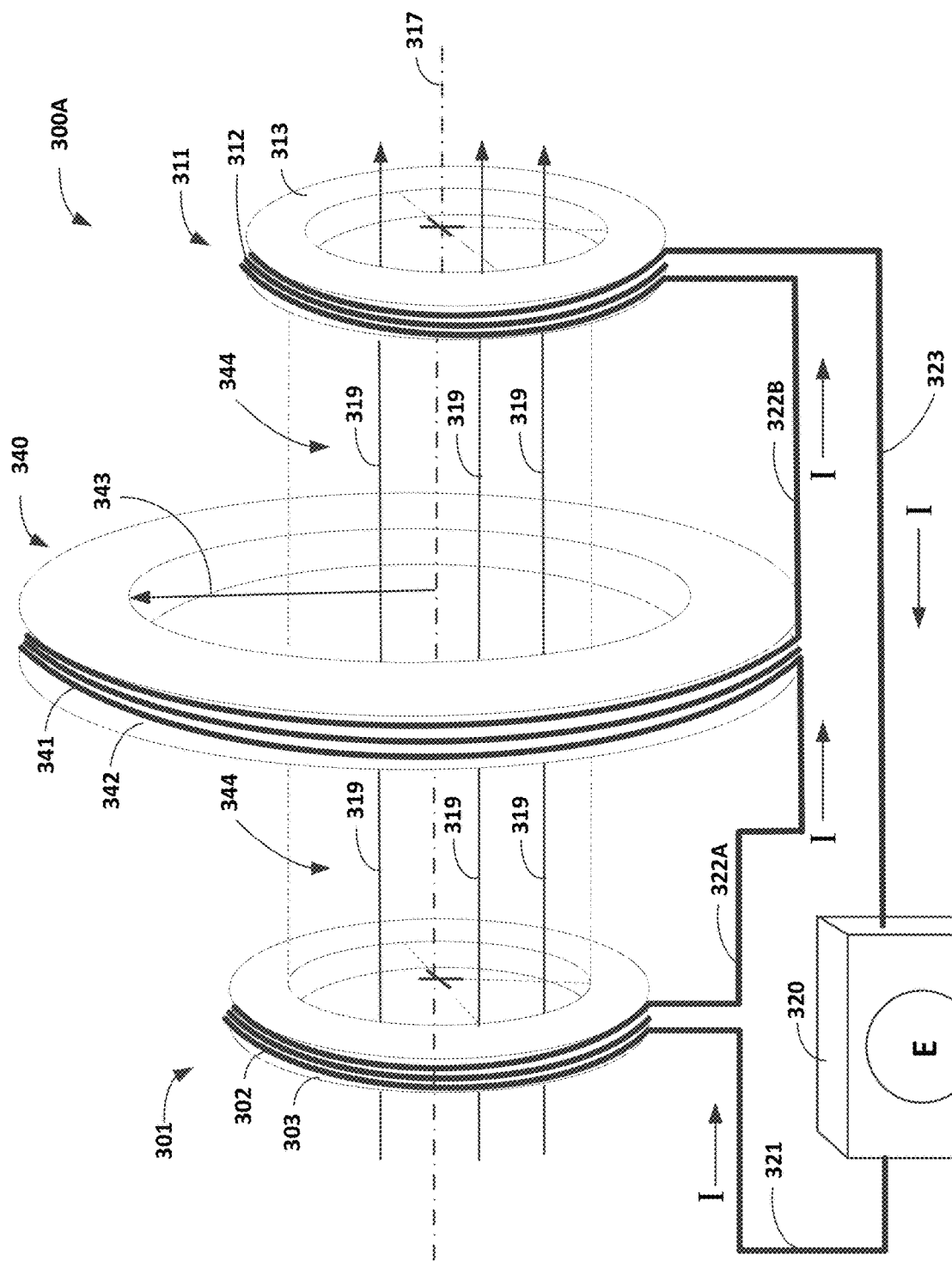
FIG. 8C illustrates a system comprising an example pair of electrical coils and a third electrical coil in accordance with various examples described in this disclosure.

FIG. 8C illustrates a system 300A comprising an example pair of coils 301 and 311, and a third coil 340 in accordance with example implementations and techniques described in this disclosure. As shown in FIG. 8C, the third coil 340 includes an electrical conductor 341 wound onto a support structure 342, and positioned between coil 301 and coil 311. Third coil 340 includes a radius 343 that may comprise a radius dimension have a center point along central axis 317, and that is larger in value than the radius value for coils 301 and 311. In various examples, the arrangement illustrated in FIG. 8C may be a Maxwell coil, and is configured to provide a uniform magnetic field in the cylindrical region generally indicated by region 344 lying between coil 301 and 311 and passing through coil 340. In various examples, the uniformity of the magnetic field provided within region 344 when coils 301, 311, and 340 are energized provides a magnetic field strength with no more than approximately seven percent variation in the magnitude of the magnetic field throughout the region indicated by region 344. In various examples described though this disclosure, any of the "pairs" of electrical coils may include the three coils arranged in a manner the same as or in a manner similar to that illustrated by system 300A in FIG. 8C. Coil 340 may include an electrical conductor wound and/or comprising the electrical conductor as described for any of the example coils described in this disclosure.

In FIG. 8C, a first electrical conductor 321 is coupled to a first end of the electrical conductor forming winding 302 of coil 301, and may be coupled to a source of electrical energy, such as source 320 as shown in FIG. 8A at the opposite end of conductor 321. As shown in FIG. 8C, a second end of winding 302 is coupled to a first end of a second electrical conductor 322A. The second end of electrical conductor 322A is coupled to a first end of the electrical conductor forming winding 341 of coil 340. A second end of winding 341 is coupled to a first end of a third electrical conductor 322B. A second end of the third electrical conductor 322B is coupled to a first end of the electrical conductor forming winding 312 of coil 311. A second end of the electrical conductor forming winding 312 of coil 311 is coupled to a forth electrical conductor 323. A second end of the fourth electrical conductor 323 may be coupled to electrical source 320.

As such, the winding 302 is electrically coupled in series with winding 341 and further in series with winding 312. When coupled to source 320 as illustrated in system 300A, source 320 may provide a current I to conductor 321, which would be conducted through winding 302 of coil 301, through electrical conductor 322A to winding 341 of coil 340, through electrical conductor 322B to winding 312 of coil 311, and through conductor 323 back to source 320, completing the electrical circuit allowing a flow of current "I" as described. As such, a same level of current "I" flows through winding 302 of coil 301, through winding 341 of third coil 340, and through winding 312 of second coil 312, as provided by source 320, at any given time. As would be understood by one of skill in the art, the direction of current flow "I" may vary from one direction to the opposite direction through the electrical path described above with respect to system 300A. In various examples, source 320 may include an oscillator, a power amplifier, and a suitable matching network to suitably drive the coils 301, 311, and 340 for example as illustrated and described with respect to FIGS. 12A and 12B.

Figure 9:
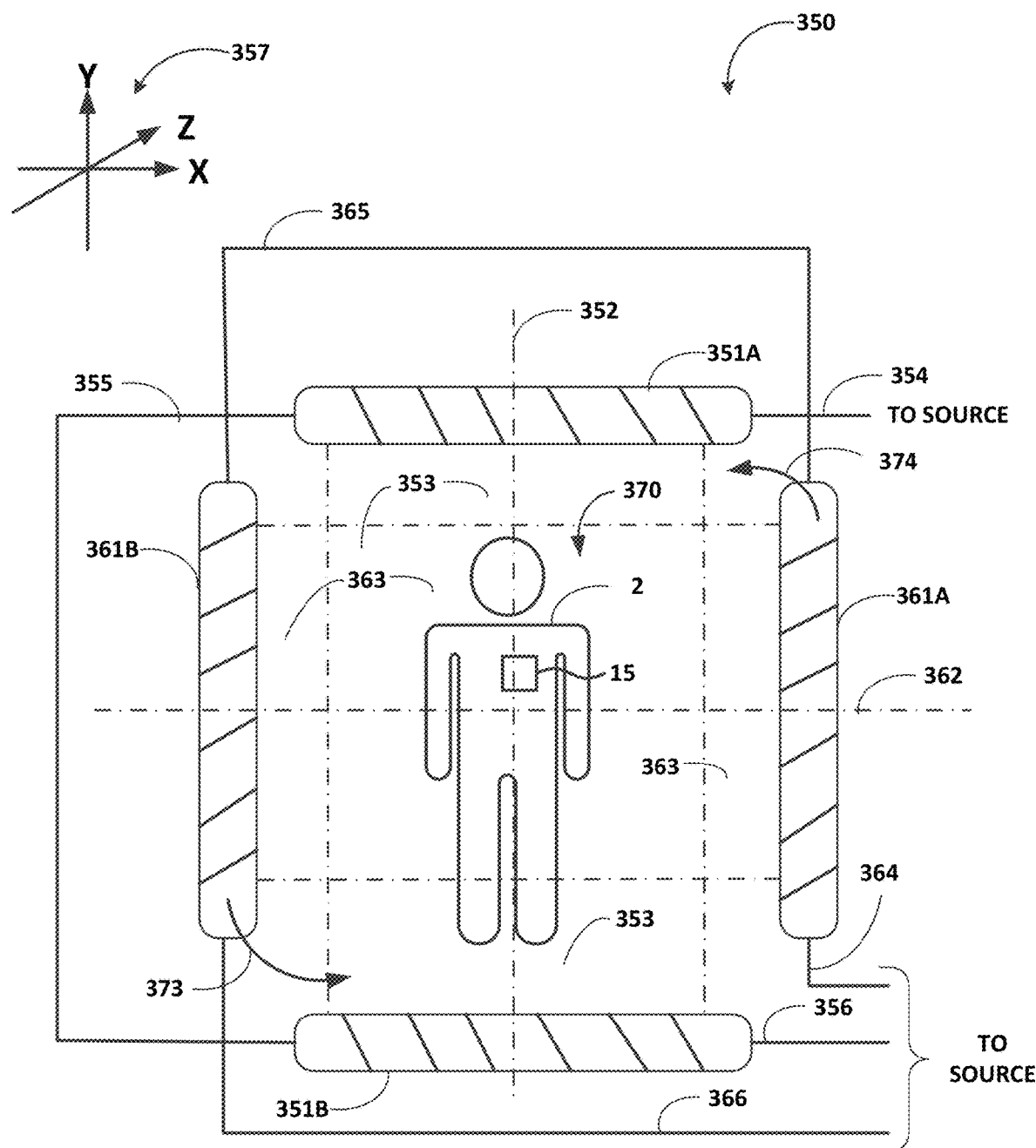
FIG. 9 is a conceptual drawing illustrating an example inductive recharging system in conjunction with a patient in accordance with various examples described in this disclosure.

FIG. 9 is a conceptual drawing illustrating an example inductive recharging system 350 in conjunction with a patient 2 according to various examples described in this disclosure. As shown, system 350 includes a first pair of coils 351A/351B, in some examples arranged to provide a first Helmholtz coil, and a second pair of coils 361A/361B, in some examples arranged to provide a second Helmholtz coil, although examples of coils 351A/351B and 361A/361B are not necessarily limited to being configured as Helmholtz coils. FIG. 9 includes an illustrative patient 2 having at least one implanted medical device 15 positioned between each of coils 351A/351B and 361A/361B.

The arrangement and scale of the first pair of coils 351A/351B and the second pair of coils 361A/361B, and illustrative patient 2, and implanted medical device 15 are not intended to represent proper dimensions and/or relative scale of these devices or the illustrative patient 2 and the implanted medical device 15, but is intended to be illustrative of various principles associated with the examples of the inductive recharging systems described throughout this disclosure. In various examples, the dimensions associated with the arrangement of the coils falls within the ranges of dimension provided above with respect to FIG. 8A and/or FIG. 8C. Further, the description of system 350 as illustrated in FIG. 9 is made based on an illustrative example having patient 2 lying down in a face-up position (e.g., patient 2 would be lying down and facing to be looking outward from the drawing, with a right arm closest to coil 361B). However, examples of recharging system 350 are not limited to systems where the patient 2 is required to lie down, and for example patient 2 may also be in a sitting position, wherein the positions of the coils would remain the same with respect to the orientation and positioning relative to patient 2.

As illustrated in FIG. 9, coils 351A/351B each include a winding of an electrical conductor (illustrated by the diagonal lines crossing each coil) having a central axis 352 in the Y direction as indicated by coordinate system 357, separated from each other so as lie in separated parallel planes lying in the X-Z axes of coordinate system 357, and having the common central axis 352 perpendicular to these parallel planes. In a similar manner, coils 361A/361B each includes a winding of an electrical conductor (illustrated by the diagonal lines crossing each coil) having a common central axis 362 in the X direction as indicated by coordinate system 357, separated from each other so as lie in separated parallel planes lying in the Y-Z axes of coordinate system 357, and having the central axis 362 perpendicular to these parallel planes. The planes in which coils 351A/351B lie are perpendicular to each of the planes in which coils 361A/361B lie, and central axis 352 of coils 351A/351B is perpendicular and orthogonal to the central axis 362 of coils 361A/361B. Each of the pairs of coils 351A/351B and coils 361A/361B are electrically coupled to a source of electrical energy, e.g., a recharging system, such as source 320 as illustrated and described with respect to FIG. 8A, or for example recharging circuitry 402 as illustrated and described with respect to FIG. 12A or FIG. 12B. As shown in FIG. 9, an electrical conductor 354 couples a first end of coil 351A to the source of electrical energy. A second end of coil 351A is coupled to electrical conductor 355, wherein electrical conductor 355 is also coupled to a first end of coil 351B. A second end of coil 351B is coupled to the source of the electrical energy. As such, coils 351A/351B are electrically coupled in a series arrangement to the source. In a similar manner, an electrical conductor 364 couples a first end of coil 361A to the source of electrical energy. A second end of coil 361A is coupled to electrical conductor 365, wherein electrical conductor 365 is also coupled to a first end of coil 361B. A second end of coil 361B is coupled to the source of the electrical energy. As such, coils 361A/361B are electrically coupled in a series arrangement to the source.

The source of electrical energy is configured to provide a flow of current to each of the serial arrangements of the pairs of coils 351A/351B and 361A/361B to energize the coils, and cause the coils to generate a magnetic field around each coil. Because the pairs of coils 351A/351B and 361A/361B are arranged as shown in FIG. 9, and in particular if arranged as Helmholtz coil pairs, respectively, each pair of coils generates a cylindrical region between the coils having a uniform magnetic field between the respective pairs of coils within the cylindrical region for that particular pair of coils. For example, the pair of coils 351A/351B, when energized, provides a cylindrical region in the space between the coils, generally indicated by areas 353, having a uniform magnetic field, generally aligned with central axis 352, and having an intensity based at least in part on the amount of electrical energy provided to the pair of coils 351A/351B by the source of electrical energy electrical coupled to coils 351A/351B. In a similar manner, the pair of coils 361A/361B, when energized, provide a cylindrical region in the space between the coils, generally indicated by areas 363, having a uniform magnetic field, generally aligned with central axis 362, and having an intensity based at least in part on the amount of electrical energy provided to the pair of coils 361A/361B by the source of electrical energy electrical coupled to coils 361A/361B. Because central axis 352 is perpendicular and orthogonal to central axis 362, the uniform field of magnetic flux generated by coils 351A/351B will be perpendicular and orthogonal to the field of the magnetic flux generated by coils 361A/361B.

The arrangement of the pairs of coils, when energized, forms a resultant magnetic region between all four coils, generally indicated by overlapping region 370. As shown in FIG. 9, coil 351A is over the head of patient 2, and coil 351B is below the patient, or may be at some position surrounding some portion of the patient, for example the legs of patient 2, but remains below the area of implantation of IMD 15. The central axis 352 between the pair of coils 351A/351B runs longitudinally along the patient in an axis formed between the head and feet of patient 2. Coil 361A is located to the left of patient 2, and coil 361B is located to the right of patient 2. The central axis 362 between the pair of coils 361A/361B runs across the patient 2 in a right to left or left to right orientation. The overlapping regions 370 generally has a three-dimensional shape in the X, Y, and Z axis of coordinate system 357 defined by the intersection of the cylindrical region 353 provided by coils 351A/351B and the cylindrical region 363 provided by coils 361A/361B. Because the central axes 352, 362 are coplanar and perpendicular to each other, and intersect at the mid-point along the axes between the respectively pairs of coils, the areas of the cylindrical regions that overlap include portions of the cubic volume between the pairs of coils.

As such, the relative position of IMD 15 within the overlapping region 370 should have substantially no effect on the relative intensity of the magnetic fields being imposed on IMD 15 when IMD 15 is located anywhere within the overlapping region 370. Further, the resultant magnetic field intensity within the overlapping regions is relatively uniform in magnitude, and the direction of the H field can be steered in a direction suitable to align with the secondary/receive coil of IMD 15, thus maximizing the power delivered to the IMD. For example, if the patient 2 is higher or lower relative to a direction along central axis 352, (e.g., closer or farther away from coil 351A), as long as IMD 15 remains within the overlapping region 370, the power delivered to the IMD should be largely independent of position. In addition, if the patient 2 is more left or more right relative to a direction along central axis 362, (e.g., closer or farther away from coil 361A), as long as IMD 15 remains within the overlapping region 370, the level of the intensity of the magnetic field being imposed on IMD 15 resulting from both pairs of coils should be substantially independent of position.

Because of this flexibility with respect the location of IMD 15, knowledge of, for example, the implantation position and, for example, the depth of the implantation with respect to IMD 15 is no longer required in order to provide the proper levels of magnetic field intensities for safely recharging IMD 15 using the inductive charges provided by coils 351A/351B and 361A/361B. Once IMD 15 is positioned anywhere within the overlapping regions 370, the only remaining variable with respect to the level of coupling of energy from the magnetic fields provided in overlapping region 370 is the orientation of a planar or otherwise orientation sensitive antenna provided in IMD 15 relative to central axis 352 and 362 relative to the Z axis of coordinate system 357. For example, the orientation of a planar antenna may be defined by the normal direction of the coil, the normal direction perpendicular to the plane in which the coil of the planar antenna lies. If a planar antenna resides substantially in a plane corresponding to the Y-Z axes of coordinate system 357 (e.g., normal direction is along the X-axis), there will be good inductive coupling between the planar antenna and coils 361A/361B, as the central axis 362 of coils 361A/361B aligns with the normal direction of the coil of the planar antenna. On the other hand, if the coil of the planar antenna resides substantially in a plane corresponding to the X-Y axes (normal direction along the Z-axis), or lies substantially in a plane corresponding to the X-Z axes (normal direction along the Y-axis), inductive coupling between coils 361A/361B as positioned in FIG. 9 will be poor.

One solution to this orientation issue is to articulate at least one of the pairs of coils, for example coils 361A/361B, so that the central axis 362 of the coils may be rotated around central axis 352 at the point where central axis 362 intersects central axis 352, while keeping central axis 362 perpendicular and orthogonal to central axis 352, and the point of intersection of these central axes remaining the same point of intersection. Arrow 374 is illustrative of one example of this rotation, wherein coil 361A is rotated from the left side of the patient 2 toward the back side (e.g., underneath the patient as illustrated in FIG. 9) of patient 2. Arrow 373 further illustrates the rotation of coil 361B from the right side of patient 2 to a position toward the front side of patient 2, performed in conjunction with the rotation of coil 361A. In performing the rotation, both coils 361A and 361B remain in parallel planes relative to each other, and maintain the same respective position and distance from each other relative to central axis 362, while also maintain a same relative distance from central axis 352 and remain in planes that are perpendicular to each of the planes in which coils 351A and 351B respectively lie. A possible ending position of the pair of coils 361A/361B when rotated 90-degrees in the manner described above is illustrated in FIG. 10.

Figure 10:
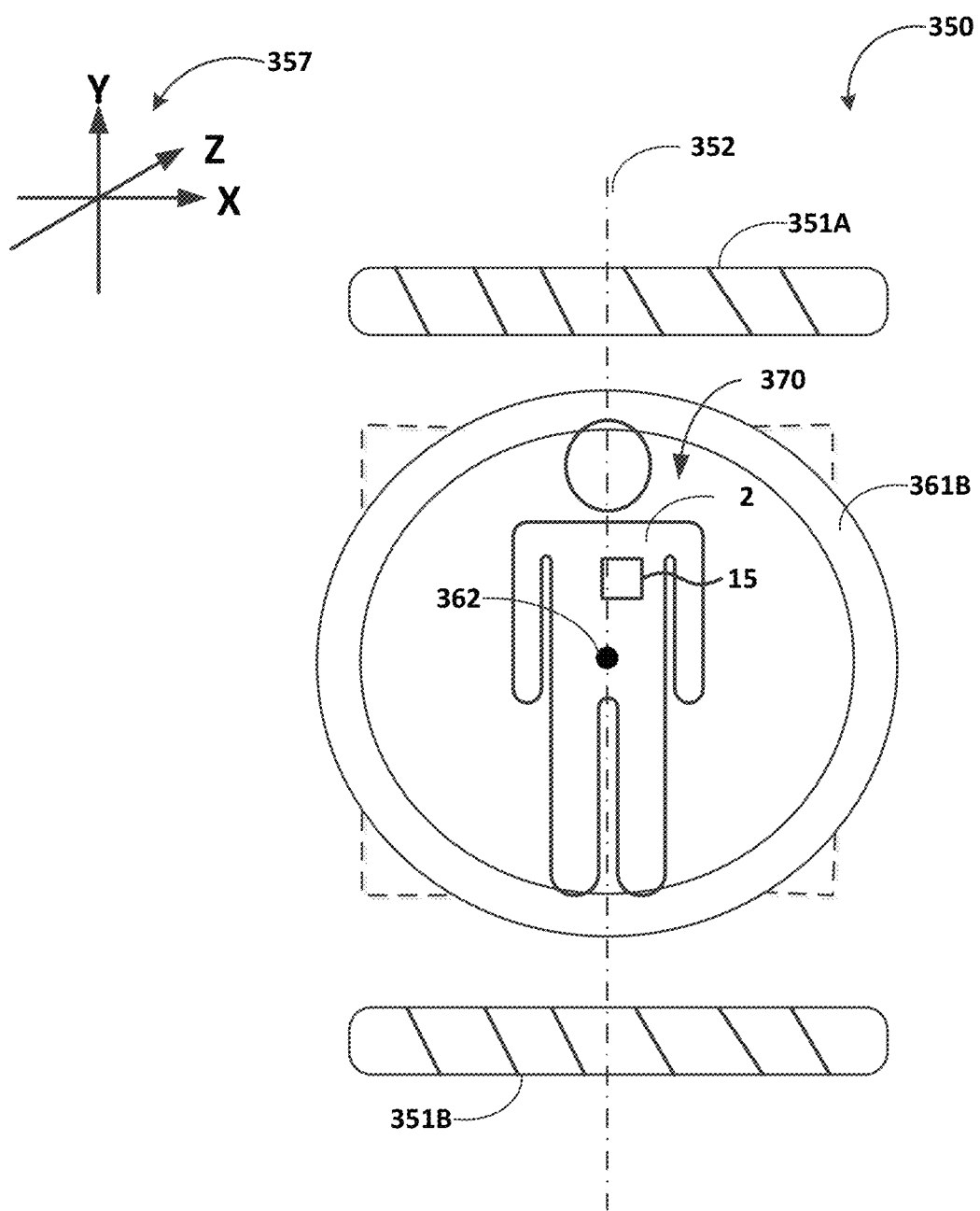
FIG. 10 is a conceptual drawing illustrating an example inductive recharging system in conjunction with a patient having coils repositioned relative to the position shown in FIG. 9.

FIG. 10 is a conceptual drawing illustrating an example inductive recharging system 350 in conjunction with a patient 2 having implanted medical device 15, and having coils repositioned relative to the position shown in FIG. 9, according to various implementations and techniques described in this disclosure. As shown in FIG. 10, coils 351A/351B remain in a same position as illustrated in FIG. 9. As illustrated in FIG. 10, coil 361B has been rotated from a position to the left of patient 2 to now being positioned over the patient, e.g., the patient is looking upward toward coil 361B. In addition, coil 361A has been rotated so as to now be positioned underneath patient 2 and concentric with central axis 362, wherein central axis 362 now has a longitudinal axis direction that aligns with the Z-axis of coordinate system 357. The IMD 15 remains within the overlapping regions 370 generated by the pairs of coils 351A/351B and 361A/361B, but now the alignment of the magnetic field provided in overlapping region 370 may better align with and thus better couple induced electrical energy into the antenna of IMD 15.

As further describe below, the amount, e.g., as expressed as an angle in degrees, of rotation of coils 361A/361B does not need to be 90 degrees, and in some examples, may be less than 90 degrees. In various examples as further described below, the amount of rotation of coils 361A/361B may be determined based on a feedback signal provided from IMD 15 that is indicative of the level of coupling that is being achieved at a receiving antenna within IMD 15. In other examples, a measurement of an effect on the level of energy being provided to the coils 361A/361B is calibrated against the measured strength of the magnetic field being generated within overlapping regions, and based on that comparison, an indication of the level of efficiently of the coupling of the inductive energy to the receiving antenna within IMD 15 can be made. The determination of the level of efficiency of the coupling may be used to determine the degree of rotation and the final position of the coils 361A/ 361B as part of the rotation process.

Figure 11:
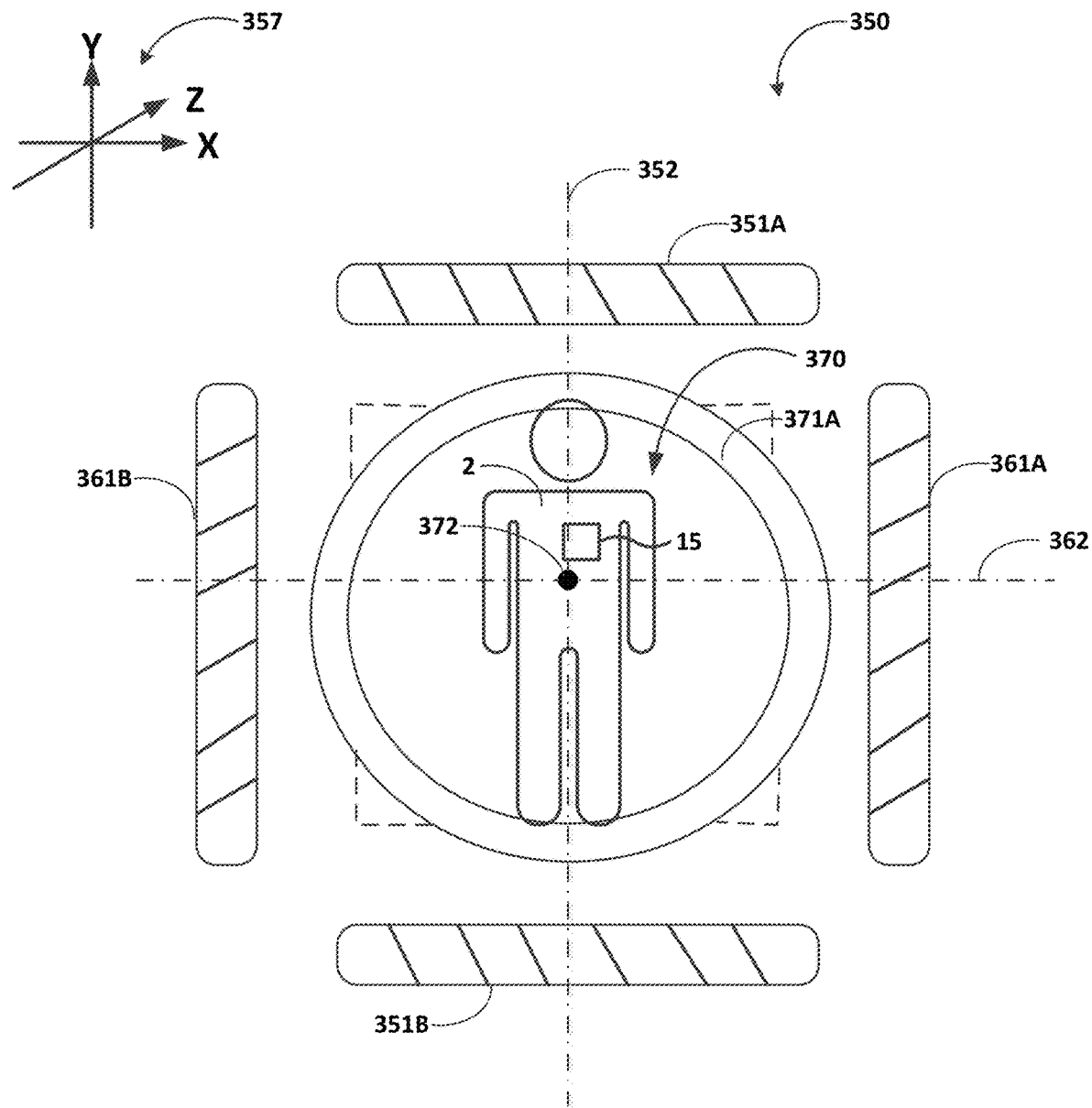
FIG. 11 is a conceptual drawing illustrating an alternative example of inductive recharging system in conjunction with a patient according to various examples described in this disclosure.

FIG. 11 is a conceptual drawing illustrating an alternative example of inductive recharging system 350 in conjunction with a patient according to various examples described in this disclosure. As shown in FIG. 11, coils 351A/351B and coils 361A/361B remain in the same positions as described and illustrated with respect to FIG. 9. In the example of system 350 as illustrated in FIG. 11, instead of rotating coils 361A/361B, a third set of coils, comprising coils 371A and 371B, are added to system 350. In some examples, coils 371A and 371B are arranged to form a Helmholtz coil. Coil 371A may be positioned above patient 2, e.g., patient 2 would be looking up toward coil 371A. Coil 371B may be positioned under patient 2 and behind coil 371A, and thus not visible in FIG. 11. Coils 371A, 371B lie in parallel planes relative to each other, the planes in the X-Y plane of coordinate system 357, and are concentric around central axis 372. Central axis 372 is perpendicular and orthogonal to both central axes 352 and 362, and intersects axes 352 and 362 at the mid-point for all three axes. By providing the third set of coils 371A/371B, in some examples arranged as a Helmholtz coil, and positioned as shown in FIG. 11 relative to coils 351A/351B, coils 361A/361B, and IMD 15, the problem with respect the Z-axis orientation of the receiving antenna of IMD 15 is resolved, and any orientation of the antenna of IMD 15 that falls within the overlapping regions 370 now comprising the resultant magnetic fields generated by all three pairs of coils illustrated in FIG. 11 will receive a composite coupling that represents an efficient inductive coupling of the energy provided by the coils to the receiving antenna of IMD 15. In the configuration of FIG. 11, the maximum efficient coupling between the energy generated as the resultant magnetic field and the receiving antenna of IMD 15 may be achieved without the need to articulate, e.g., physically move, one or more of the sets of coils being used in the recharging process of IMD 15.

Figure 12A:
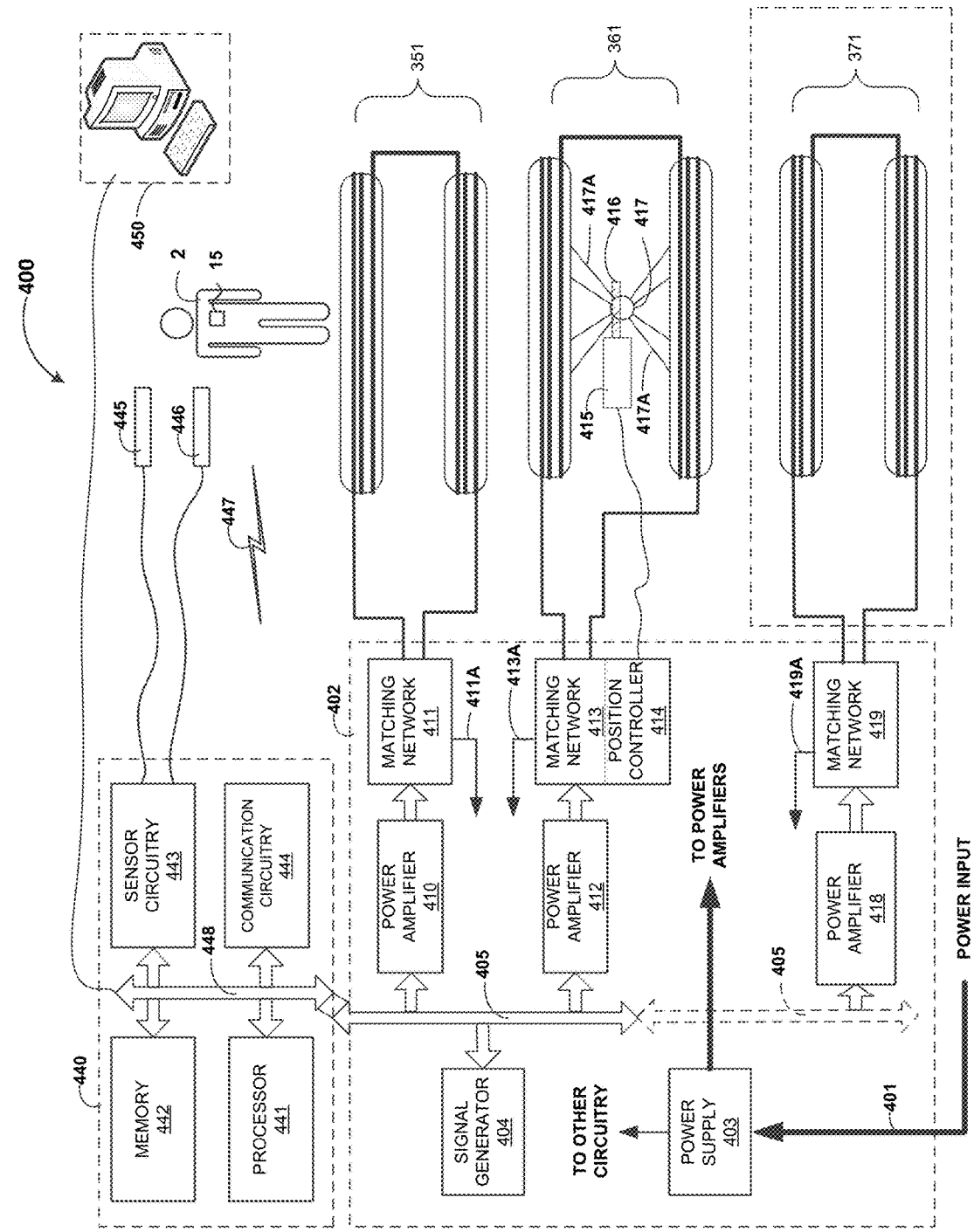
FIG. 12A is a conceptual block diagram illustrating a recharging system for recharging one or more implanted medical devices implanted in a patient according to various examples described in this disclosure.

FIG. 12A is a conceptual block diagram illustrating an example recharging system 400 for recharging one or more implanted medical devices 15 implanted in a patient 2 according to various examples described in this disclosure. As illustrated, system 400 is configured to provide inductive recharging of one or more implanted medical devices, illustratively represented as IMD 15, that are implanted in a patient, illustratively represented as patient 2. System 400 includes recharging circuitry 402 that is coupled to at least two pairs of coils 351, 361, and may optional be configured to be coupled to a third pair of coils 371. The arrangements of coils 351, 361, and 371 relative to patient 2 are not necessarily intended to be illustrative of the actual arrangement, for examples with respect to position and scale of these pairs of coils and patient 2 during a period of time when recharging of IMD 15 is occurring, and is intended to be illustrative of various features of system 400. The actual arrangements of coils 351, 361, and 371 relative to each other and relative to patient 2 and IMD 15 may be as illustrated and described with respect to coils 251A/251B, 261A/261B, and 271A/271B as illustrated and described with respect to FIGS. 7A-7D, with respect to coils 301 and 311 as illustrated and described with respect to FIGS. 8A-8B, with respect to coils 301, 311, and 340 as illustrated and described with respect to FIG. 8C, with respect to coils 351A/351B and 361A/361B as illustrated and described with respect to FIG. 9 and/or FIG. 10, and/or with respect to coils 351A/351B, 361A/361B, and 371A/371B as illustrated and described with respect to FIG. 11.

As illustrated in FIG. 12A, system 400 includes control circuitry 440 coupled to recharging circuitry 402, and includes a processor 441, a memory 442 coupled to processor 441, for example by bus/connections 448 (herein after "bus 448"). Memory 442 may store program instructions that, when retrieve and executed by processor 441, provides programming steps that allow processor 441 to control recharging circuitry 402 to perform the recharging processes associated with inductively recharging a power source or power sources located within an IMD 15 implanted in patient 2. In addition, memory 442 may also store values, for example charging values, charging times, patient history associated specifically with patient 2, communication protocols, and any other information that may be required or that may be helpful to allow processor 441 to control the inductive recharging process being used to recharge the power source or sources included in IMD 15 when implanted within patient 2.

Control circuitry 440 may include communication circuitry 444. Communication circuitry 444 may be used to receive and process signals from the IMD 15 implanted in patient 2 for use by processor 441 in controlling the inductive recharging processes including, but not limited to a battery management system that monitors and optimizes the recharge process. Communication circuitry 444 may also provide wireless communications with devices located externally to system 400, for example external device 14, or for examples external computing devices 230A-N, and/or external sever 224 as described and illustrated with respect to FIG. 7A. In FIG. 12A, communication circuitry 444 as may also be used to download information, such as programming information, to control circuitry 440 that may then be stored in memory 442, and accessed by processor 441. In addition, memory 442 may be used to store information related to the recharging process performed by system 400, such as the levels of energy provided during a recharging process to coils 351, 361, 371, any fault conditions that have occurred during the recharging process, and any other information deemed necessary or helpful that may be related to the recharging processes performed by system 400. This information as stored in memory 442 may be provided to computer device 450, and/or uploaded and transmitted through communication circuitry 444 to some other external device, as described above. Control circuitry 440 as illustrated in FIG. 12A may also include sensor circuitry 443 configured to be coupled one more different sensors 445, 446, and to receive signals from the sensors that may be further processed by sensor circuitry 443 and/or by processor 441, to provide and/or derive information that may be further used to control and regulate the inductive recharging processes being performed by system 400.

In various examples, one or more of the circuits illustrated as comprising control circuitry 440 may instead be provided by computing device 450. In various examples, computing device 450 includes a display and one or more input devices, such as a keyboard and/or a computer mouse, that allow a user, such as a physician or a clinician, to interact with the system 400. This interaction may include interaction to control the recharging processes to be performed or being performed by system 400.

As shown in FIG. 12A, recharging circuitry 402 includes a power supply 403, a signal generator 404 (which may be comprised of an oscillator and signal generation circuitry), a plurality of power amplifiers 410 and 412, and a corresponding plurality of matching network circuitry 411, 413. The circuits of recharging circuitry 402 may be coupled by a bus/connection 405. Recharging circuitry 402 may optionally include a power amplifier 418 and a corresponding matching network circuitry 419 for an additional third pair of coils. Recharging circuitry 402 includes a first power amplifier 410 coupled to signal generator 404 to receive a signal from the signal generator 404, and also coupled to matching network circuitry 411, and configured to provide an output signal to the matching network circuitry 411 based on the signal received from the signal generator 404. Matching network circuitry 411 may be configured to provide impedance matching between power amplifier 410 and a pair or set of coils, and to provide outputs that may be coupled to a pair or a set of coils, illustratively represented as coils 351. Recharging circuitry 402 includes a second power amplifier 412 coupled to signal generator 404 to receive a signal provided by signal generator 404, and is also coupled to matching network circuitry 413, and configured to provide an output signal to the matching network circuitry 413 based on the signal received from the signal generator 404. Matching network circuitry 413 is configured to provide impedance matching between power amplifier 412 and a pair or a set of coils, and to provide outputs that may be coupled to a pair or a set of coils, illustratively represented as coils 361. As indicated above, recharging circuitry 402 may optionally include a third power amplifier 418 coupled to signal generator 404. The third power amplifier 418 may be coupled to signal generator 404 to receive a signal provided by signal generator 404, and is also coupled to matching network circuitry 419, and may be configured to provide an output signal to the matching network circuitry 419 based on the signal received from the signal generator 404. Matching network circuitry 419 may be configured to provide impedance matching between power amplifier 418 and a pair or a set of coils, and to provide outputs that may be coupled to a pair or a set of coils, illustratively represented as coils 371.

In each of these examples, power amplifiers 410, 412, and 418 (if power amplifier 418 is provided and used), receive a signal including a waveform generated by signal generator 404, and provide power amplification of the received signal that is then applied through matching network circuitry 411, 413, and 419 (if power amplifier 418 is provided and utilized), respectively, to energize coils 351, 361, and 371 (if coils 371 are provided and utilized), respectively. Matching network circuitry 411, 413, and 419 (if matching network 419 is provided and used) provides impedance matching between the output stage of the respective power amplifier that the matching network circuitry coupled to and the coils that are being energized by that power amplifier. In various examples, a typical range of impedance provided as an output from one or more of power amplifiers 410, 412, 418 may be in a range of 1 to 100 ohms, in some examples 50 ohms, wherein the real part of the input impedance of the coils 351, 361, and 371 would be in a range of 0.1 to 20 ohms, in some examples 0.5 ohms. The imaginary part of a complex impedance of the coils may be in a range of 60 to several hundred ohms, depending on the frequency of the signal or signal applied to the coils. In order to provide maximum power transfer between the power amplifier outputs and the respective coils these outputs are coupled to, the matching network circuitry 411, 413, and 419 are configured to match the impedance of the output of the power amplifier to the coils each power amplifier is coupled to through the respective matching network circuitry. In some examples, matching network circuitry 411, 413, and 419 (if matching network circuitry 419 is provided) comprise an impedance matching transformer configured to match an output impedance of a power amplifier to an input impedance of a pair or a set of coils. In some examples, matching network circuitry 411, 413, and 419 (if matching network circuitry 419 is provided) comprises a transformer and/or a capacitor rated for peak voltage of the assembly and of a capacitance value that the inductive nature of the coil is accommodated. In one implementation, an adjustable vacuum ceramic capacitor is placed in series with a 50Ω to 1Ω transformer. Other configurations and devices may be used to perform the impedance matching function of matching network circuitry 411, 413, and 419 (if matching network circuitry 419 is provided) and are contemplated for using in providing the matching network circuitry 411, 413, and 419 as described in this disclosure.

In various examples of system 400, since it is more difficult to dynamically tune the quality factor of the receive coil within an implanted medical device such as IMD 15, or rather, change the frequency at which the quality factor is a maximum, it may significantly improve the maximum power delivered to IMD 15 by fixing the frequency of the system based on the characteristics of the receive coil and using a tunable vacuum capacitor located between the power amplifier (and after a following transformer) and a coil pair, such as a Helmholtz coil pair or a Maxwell coil arrangement, in order to match the output of the power amplifiers to the impedance presented by the coils without changing the oscillation frequency, as is practiced in other rechargeable wireless power transfer systems such as the Restore Ultra device from Medtronic plc, of Dublin, Ireland. A frequency based maximization configuration may result in a non-optimal power transfer if the secondary/receive coil of IMD 15 are tuned to a frequency different than that found to maximize power transfer to the primary/transmit coils providing the inductive energy provide by system 400. Therefore, examples of the systems and methods described herein comprise tuning the impedance of the system at a fixed frequency, as opposed to varying the frequency of the system, in order to maximize the power delivered to a receive coil in the implanted device being recharged by the system.

As shown in FIG. 12A, power supply 403 is coupled to a power input 401, and is configured to receive electrical power from input 401. Power input 401 may be any source of electrical power, such as commercially available electrical power supply by an electrical utility, for example electrical power having 110-120 volts RMS single-phase power at frequency of 50-60 Hz, as is commonly available in the United States. In other examples, input 401 may provide power in other arrangements, such as but not limited to 480V three-phase in an ungrounded delta configuration at 50-60 Hz, or 208 three-phase "Y" configuration at 50-60 Hz. Other voltages, frequencies, configurations, and numbers of phases are contemplated for use as input power to system 400, as would be understood by one of ordinary skill in the art. Power supply 403 is configured to receive electrical power at input 401, and may perform various operations on the received electrical power, including conditioning, filtering, and conversion of the input power voltage to one or more different voltages, including both different voltages provided as alternating current (AC) voltage supplies and direct current (DC) power supplies as outputs from power supply 403. The outputs are generally represented by the "TO OTHER CIRCUITRY" output arrow illustratively provided as an output from power supply 403, and may include any electrical power outputs required to power the circuitry for operation of the devices included in and powered from system 400. In some examples, power supply 403 is also configured to provide one or more separate outputs, illustratively represented by the "TO POWER AMPLIFIERS" output arrow from power supply 403. These outputs from power supply 403 may be directly coupled to power amplifiers 410, 412, and 418 provided as part of recharging circuitry 402, and wherein the "TO POWER AMPLIFIERS" output is configured to provide the electrical energy used to energize the coils 351, 361, and 371 (if coils 371 are provided), respectively, under the control of the power amplifiers 410, 412, and 418 (if power amplifier 418 is provided), respectively.

In FIG. 12A, signal generator 404 is coupled to bus 405, and signal generator 404 may be configured to generate one or more output signals that are used to control the waveforms of the electrical power used to energize coils 351 and 361, and 371 (if coils 371 are provided). For example, signal generator 404 may generate a signal having sinusoidal voltage waveform and a particular frequency. This signal is provided to the power amplifiers and matching network circuitry of recharging circuitry 402. In some examples, the sinusoidal waveform is converted to the square waveform, the frequency of the square wave having a same frequency of the sinusoidal waveform generated by signal generator 404, or in other examples signal generator 404 may change the frequency of the square wave signal. In some examples, the duty cycle of the square wave may be the same as provided with the sinusoidal waveform (e.g., a 50% duty cycle), and in other examples, signal generator 404 may alter the duty cycle to a duty cycle other than a 50% duty cycle. In some examples, signal generator 404 amplifies the signal for example to alter the voltage level of the signal. In some examples, signal generator 404 is configured to process the signal to retain the processed signal as a sinusoidal waveform, but for examples acts as a buffer or driver to amplify and/or drive the output signal from the signal generator 404 to the power amplifiers 410, 412, and 418 (if power amplifier 418 is provided) and for example to prevent the power amplifiers from loading down or otherwise distorting the signal being provided from the signal generator 404. In some examples, one or more of the power amplifiers comprise a Class D amplifier. In some examples, one or more of the power amplifiers comprise a Class E amplifier. In some examples, the signal generator 404 may provide recharge frequency tuning (closed loop or open loop), to optimize the wireless power transfer between coils 351, 361, and 371 (if coils 371 are provided) and the receiving antenna of IMD 15. This tuning may or may not be integrated and coordinated with the battery management system and telemetry/communication systems.

Once processed by signal generator 404, the signal generator 404 is coupled to power amplifier 410 that is configured to control the output of electrical energy provided by matching network circuitry 411 to coils 351 using the signal processed by signal generator 404, which may be provided by a coupling the power amplifier 410 to the "TO POWER AMPLIFIER" output of power supply 403. The output from power amplifier 410 is then provided as an output to matching network circuitry 411 to energize coil 351. Matching network circuitry 411 may also include a feedback 411A loop that provides a feedback signal, such as a varying voltage level, that is indicative of the level of energy, for example a current flow, being provided to coil 351 by matching network circuitry 411. This feedback signal may be processed by one or more devices included in system 400, for example processor 441 or computing device 450, or other battery management system, to provide information that may be used to control and regulate the output of electrical energy being provided to energize coil 351. This information may also be used, or used in the alternative, to apportion power to the appropriate coil pairs, including Helmholtz coils pairs or a Maxwell coil, to maximize power delivered to the receive circuit of the implanted device being recharged.

In a similar manner, signal generator 404 also provides a signal to power amplifier 412, which receives power from the "TO POWER AMPLIFIERS" output from power supply 403, and to provide an output to matching network circuitry 413 to electrically energize coil 361. Power amplifier 412 and matching network circuitry 413 may be figured to operate and to provide any of the features and functions described above with respect to power amplifier 410 and matching network circuitry 411, respectively, in providing the electrical energy used to energize coils 361. In addition, matching network circuitry 413 includes a feedback signal 413A, that may be used in same or similar matter as described above with respect to feedback signal 411A, but for use in controlling and regulation of power amplifier 412 and the matching network circuitry 413 with respect to providing the electrical energy used to energize coils 316. This information may also be used, or used in the alternative, to apportion power to the appropriate coil pairs, including Helmholtz coils pairs or a Maxwell coil, to maximize power delivered to the receive circuit of the implanted device being recharged.

In various examples, the same signal is provided by signal generator 404 to both power amplifier 410 and power amplifier 412. The power amplifiers 410, 412 may then process the signal and control matching network circuitry 411 and 413, respectively, so that a same level of electrical energy is provided to both sets of coils 351 and 361 at any given time when coils 351 and 361 are energized. In other examples, a different signal is provided by signal generator 404 to power amplifier 410 and to power amplifier 412, which may result in a different level of electrical energy being provided to energize coils 351 as is being provided to coils 361 at any given time. In some examples, a same signal is provided by signal generator 404 to both signal power amplifiers 410 and 412, but power amplifiers 410 and 412 process this same signal differently to provide different outputs to matching network circuitry 411 and 413 respectively, resulting in a different level of energy being provided to coils 351 as compared to coils 361 at any given time when the coils are energized.

In addition, in some examples of system 400, a position controller circuit 414 is coupled to matching network circuitry 413. The position controller circuit 414 is coupled to a motor 415, and is configured to drive the motor 415. Motor 415 includes a drive shaft 416 that is mechanically coupled to a hub 417 coupled to a set of supports 417A that mechanically couple the hub 417 to coils 361. Supports 417A and hub 417 are configured to, when rotated by a rotational force provided by motor 415 and shaft 416, rotate the position of coils 361 in a manner that maintains coils 361 parallel to each other, in planes perpendicular to the planes where coils 351 are positioned, and keeping the central axis of coils 361 perpendicular to and at a same point of intersection with a central axis of coils 351, for example as illustrated and described above with respect to coils 351A/351B and 361A/361B and FIGS. 9 and 10. As described above, rotation of the coils 361 may be performed to align the magnetic field provided by coils 361 to better couple with the orientation of a receiving antenna provided in IMD 15 of patient 2.

In some examples, motor 415, under the control of position controller circuit 414, is configured to rotate drive shaft 416 to rotate hub 417 and supports 417A to in order to rotate the position of coils 361 in the manner described above. In some examples, coils 316 are energized and the rotation process is performed while feedback is provided to recharging circuitry 402 that is indicative of the level of coupling (e.g., coupling efficiency) that is being achieved by the rotation of coils 316. Position controller circuit 414 may be configured to receive this feedback information, and to rotate coil 316 to a position providing the most efficient coupling of the magnetic field being provided by coils 351 and 316 to the antenna of IMD 15 based on the feedback being provided. For example, IMD 15 may be configured to provide a wireless signal (e.g., illustratively wireless signal 447) that is indicative of the level of power being received by an antenna within IMD 15 as a result of the magnetic fields being provide by the energization of coils 351 and 361. As coils 316 are rotated by position controller circuit 414 through motor 415, shaft 416, hub 417 and support 417A, the indication of the level of energy being coupled to the antenna may be provided as the wireless signal 447, received by communication circuitry 444. Communication circuitry 444 may be configured to further process the received wireless signal 447 indicative of the level of energy being inductively coupled to an antenna of IMD 15, and provide the signal or information derived from the wireless signal 447 to position controller circuit 414 in order to control the rotation of coils 361 as described above.

In other examples, an external sensor, such as illustratively represented by sensors 445, may be placed in a location that allows the external sensor to sense the strength of the magnetic fields generated by coils in the overlapping region provided by coils 351 and/or 361, and to provide this sensed field strength as feedback to system 400 for use by position controller circuit 414. A Hall effect sensor is an example of a type of sensor that may be use to sense parameters that are indicative of a strength and relative direction of a magnetic field, and may be provided as one or more sensor of sensors 445 as included in system 400. In various examples, the output from sensors 445 is received by sensor circuitry 443, as part of a control circuitry 440 provided with system 400. The sensor circuitry 443 may process the signal received from sensors 445, and provide the signal and/or information derived from processing the signal to the position controller circuit 414 through bus 448 and bus 405 for use by the position controller circuit 414 in positioning coils 316 as described above.

In examples of recharging circuitry 402 that includes power amplifier 418, matching network circuitry 419, and coils 371, the positioning of coils 371 relative to coil 351 and 361 may be such the coils 371 lie in parallel planes that are perpendicular to both the planes coils 351 and coils 361 and have a central axis of coils 371 that is both perpendicular to and orthogonal to the central axes of coils 351 and coils 361. This arrangement may be the same arrangement as illustrated and described with respect to FIG. 11. As described above, when a third set of coils 371 is provided a part of system 400, the need to rotate a second set of coils 361 may no longer exist, and the third set of coils, e.g., coils 371, compensates for any orientation issues of antenna within IMD 15 that are not adequately addressed with respect to inductive coupling efficiencies between the antenna of IMD 15 and coils 351 and 361. In some examples where the third set of coils 371 is provided, the position controller circuit 414, motor 415, drive shaft 416, and a rotatable version of a hub 417 may not be provided as part of system 400.

In examples of system 400 where the power amplifier 418, matching network circuitry 419 and the third set of coils 371 are provided, these devices may be configured to provide any or all of the features provided by and to perform any or all of the functions described with respect to the corresponding devices described above with respect to the energization of coils 351 and 361. For example, matching network circuitry 419 includes a feedback signal 419A that may be configured to provide a feedback signal indicative of the level of electrical energy being provided to energize coils 317. This feedback signal may be provided to power amplifier 418 or to other circuits and/or devices in system 400, to further control and regulate power amplifier 418 and network matching circuitry 419 in a similar manner as described above with respect to the feedback signals 411A and 413A and coils 351 and 361 respectively.

In various examples, other sensors 446 may be included in system 400. For example, one or more temperatures sensors may be included with sensors 446. In some examples, each of coils 351, 361, and 371 includes a temperature sensor located so as to sense a temperature of one or both of the pair of coils included as coils 351, 361, and 371. The temperature signal or signals provided by sensors 446 may be received by sensor circuitry 443 and processed for example to determine that a coil is operating properly, or for example is overheating. This information may be provided to or used to control one or more of power amplifiers 410, 412, and 418, to for example cause the power amplifiers to shut off or otherwise regulate, for example reduce the level of the electric energy being provided to one or more of the coils determined to be overheating. In some examples, a temperature sensor 446 is located in a position adjacent to patient 2, wherein the sensor may be external to patient 2 or may be an implanted sensor a sensor (e.g., sensor 19 that is implanted within patient 2). The temperature signal provided by sensors 446 related to a sensed patient temperature may be provide to control circuitry 440 and/or to recharging circuitry 402 as a safety precaution, wherein if the temperature sensed by the sensor of sensors 446 is deemed to be too high, or exceeds a predetermined maximum temperature value for patient 2, control circuitry 440 may perform control of power amplifiers 410, 412, and 418 (if provided) to shut off or otherwise regulate, for example reduce the level of electrical energy being provided to coils 351, 361, and 371 (if provided). An alarm signal may also be provided as an output from system 400 in response to detection of this patient over-temperature condition. This alarm signal may be output to computing device 450, or to some other external device via a transmission generated and transmitted to the external devices by communication circuitry 444.

In operation, a patient 2 with at least one IMD 15 that requires recharging of the power source located within the at least one IMD 15 is positioned so that the IMD 15 is located within the area of the resultant magnetic fields that will be generated by coils 351, 361 and 371 (if coils 371 are provided) when the coils are energized. Based on control provided by processor 441 and/or by instructions received from computer device 450, signal generator circuit 404 generates one or more signals that are provided to the power amplifiers 410, 412 and 418 (if power amplifier 418 is provided and is being used). The power amplifiers, based at least in part on the received signal, and in some examples based on instructions received from processor 441, provide power outputs to energize coils 351, 361, and 371 (if coils 371 are being utilized). When energized, the coils being utilized generate a resultant magnetic field region that imposes the resultant magnetic fields onto the antenna of IMD(s) 15, and begins to provide inductive charging to the power source located in IMD 15. In examples that normally do not include the third set of coils 371, signals either provide by IMD 15 to communication circuitry 444 and/or signals provided as feedback signals 411A, and 413A, are processed, for example by processor 441 and/or by position controller circuit 414, and used to reposition coils 316, as described above, if deemed necessary, in order to provide better coupling efficiency between the magnetic field provided by coils 316 and the antenna of the IMD 15 being recharged. In examples including coils 371, coils 371 are energized in a same or similar manner as described above with respect to coils 351 and 361. In such examples, the set of three coils 351, 361, and 371 provide the proper orientation of the magnetic fields imposed onto the antenna of IMD 15, and repositioning of coils 361 may not be required.

During the process of inductively recharging the power source located in IMD 15, various sensors 445, 446, may be monitored, and the information received from or derived from the sensors may be used to further control the recharging process. For example, temperature sensors located at the coils may provide signals indicative of the temperatures of coils 351, 361, 371 (if coils 371 are being utilized), and may be monitored during the recharging process to determine if one or more of the coils may be overheating. In some examples, a temperature of the patient 2 or of IMD 15 may be monitored during the recharging process. These sensed temperatures of patient 2A and/or of IMD 15 may be used to control the recharging process for example by lowering (reducing) the level of energy being provided to the coils if the temperature of the patient or IMD 15 is rising, and for example shutting off the energy being provided to the coils if the temperature of the patient or of IMD 15 exceeds a temperature considered to be safe for the patient. Further, the strength of the magnetic field being generated and imposed on IMD 15 may be monitored during the recharging process, and the sensed strength of the magnetic fields may be processed and used to further regulate the process, for example to raise or lower the level of electrical energy being provided to the coils. Monitoring of the strength of the magnetic field imposes on the patient may be required to assure that the level of the strength of the magnetic field does not exceed a predetermined level, or a predetermined level for more than a predetermined time period. The monitoring may include a reduction, including lower the energy level or shutting off the electrical energy provided to the coils for safety reasons if the strength of the magnetic field exceeds some predetermined value or values, either instantaneous and/or over some predetermined time period.

In various examples, processor 441 regulates various functions related to the recharging process. Processor 441 may include a timer function for controlling and limiting the duration of time the patient 2A may be exposed to the magnetic fields being generated coils 351, 361, and 371 (if provided) during the recharging process. Timing functions may be provided by one or more timers included in processor 441, and may timeout based on a timer value(s) stored in memory 442. Processor 441 may also regulate a profile of the levels of electrical energy provided to the coils over the duration of the recharging process, so that the levels of electrical energy provided to each of the coils 351, 361, and 371 (if provided) may be set and/or varied over the duration of the recharging process based on a profile that may be stored in memory 442 and retrieved and executed by processor 441. In some examples, IMD 15 may provide a signal (e.g., wireless signal 447) to communication circuitry 444 that indicates the level of recharge that has been provided to the power source within IMD 15. Processor 441 may further regulate and/or terminate the recharging process of IMD 15 based on this information. For example, a wireless signal 447 provided by IMD 15 may indicate that the power source located within IMD 15 is fully recharged, and further exposure to the magnetic fields by both patient 2 and IMD 15 will provide no further charging of the power source. In such instances, processor 441 may terminate the recharging process in order to minimized the amount of exposure of patient 2 to the magnetic fields generated by system 400, regardless of whether or not a timer has indicated that the time for recharging the power source of IMD 15 has expired.

Figure 12B:
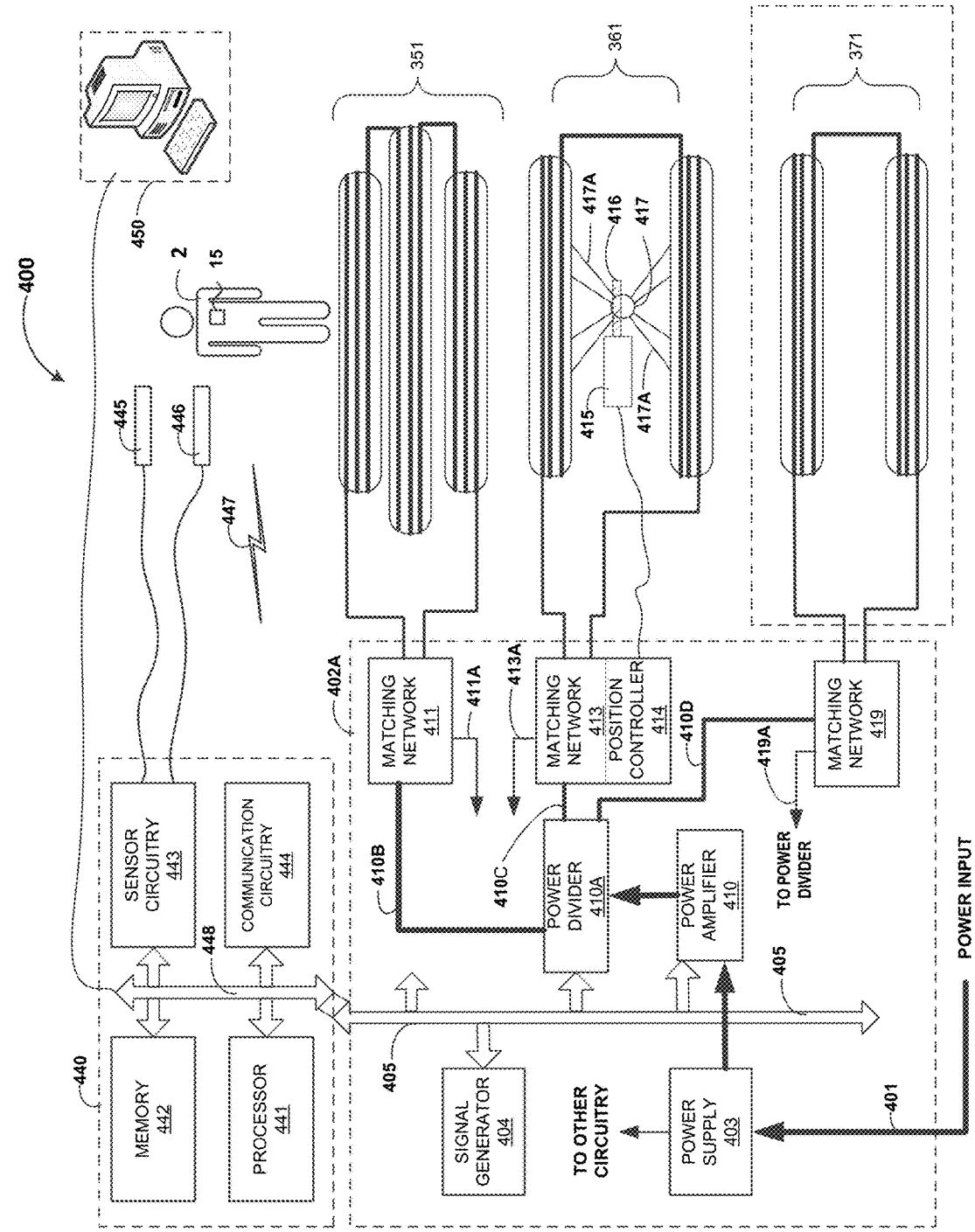
FIG. 12B is a conceptual block diagram illustrating another recharging system for recharging one or more implanted medical devices implanted in a patient according to various examples described in this disclosure.

FIG. 12B illustrates another example of a charging system 400 including recharging circuitry 402A. Recharging system 400 as illustrated in FIG. 12B may include any and all of the devices, and perform some or all of the functions described above with respect to the recharging system 400 of FIG. 12A, but with the variations described below with respect to recharging circuitry 402A. As shown in FIG. 12B, recharging circuitry 402A comprises a single power amplifier 410 coupled to a power divider circuit 410A. Power divider circuit 410A includes a first output 410B coupled to matching network circuitry 411, and a second output 410C coupled to matching network circuitry 413. Power divider circuit 410A may include a third output 410D that is coupled to matching network circuitry 419 in examples where matching network circuitry 419 and coils 371 are provided. Power amplifier 410 is configured to receive a signal generated by signal generator 404, to provide power amplification to the received signal, and to provide the amplified signal to power divider circuit 410A. Power divider circuit 410A is configured to divide the power amplified signal received from power amplifier 410, and to provide the divided power amplified signal as an output signals at outputs 410B, 410C, and to output 410D (if matching network 419 is provided and is being utilized).

In various examples, power divider circuit 410A divides power equally to each of outputs 410B, 410C, and to 410D (if output 410D is provided and is being utilized). In other examples, power divider circuit 410A may divide the power amplified signal received from power amplifier 410 unequally between the matching networks. For example, in some examples coils 351 may comprise a three-coil set being driven by matching network 411, and coils 361 may including a pair of coils being driven by matching network 413. In such examples, more or less power may be provided to the set of coils 351 relative to the amount of power being provided to the pair of coils 361 due to the different number of coils comprising coils 351 and 361. In various examples, feedback is provided by feedback lines 411A, 413A, and 419A as described above. These feedback signals may be provided to power divider circuit 410A, and used by power divider circuit 410A to adjust the level of power provided to one or more of coils 351, 361, and for example coil 371 in examples where the third set of coils is being used, based at least in part on the feedback signals provided by feedback lines 411A, 413A, and 419A (if feedback is being provided by line 419A). In various examples where each of coils 351, 361, and 371 are being utilized, power divider 410A is configured to divide power among the three axes of coils 351, 361, and 371 such that the resultant magnetic field direction is controlled to maximize the power delivered to the IMD 15. In various examples where only two sets of coils 351 and 361 are utilized, power divider 410A is configured to divide power between the two axes of coils 351 and 361, and recharging circuitry 402A is configured to position coils 361 using position controller 414 as described above such that the resultant magnetic field direction is steered so that it maximizes the power delivered to the IMD 15.

Figure 13:
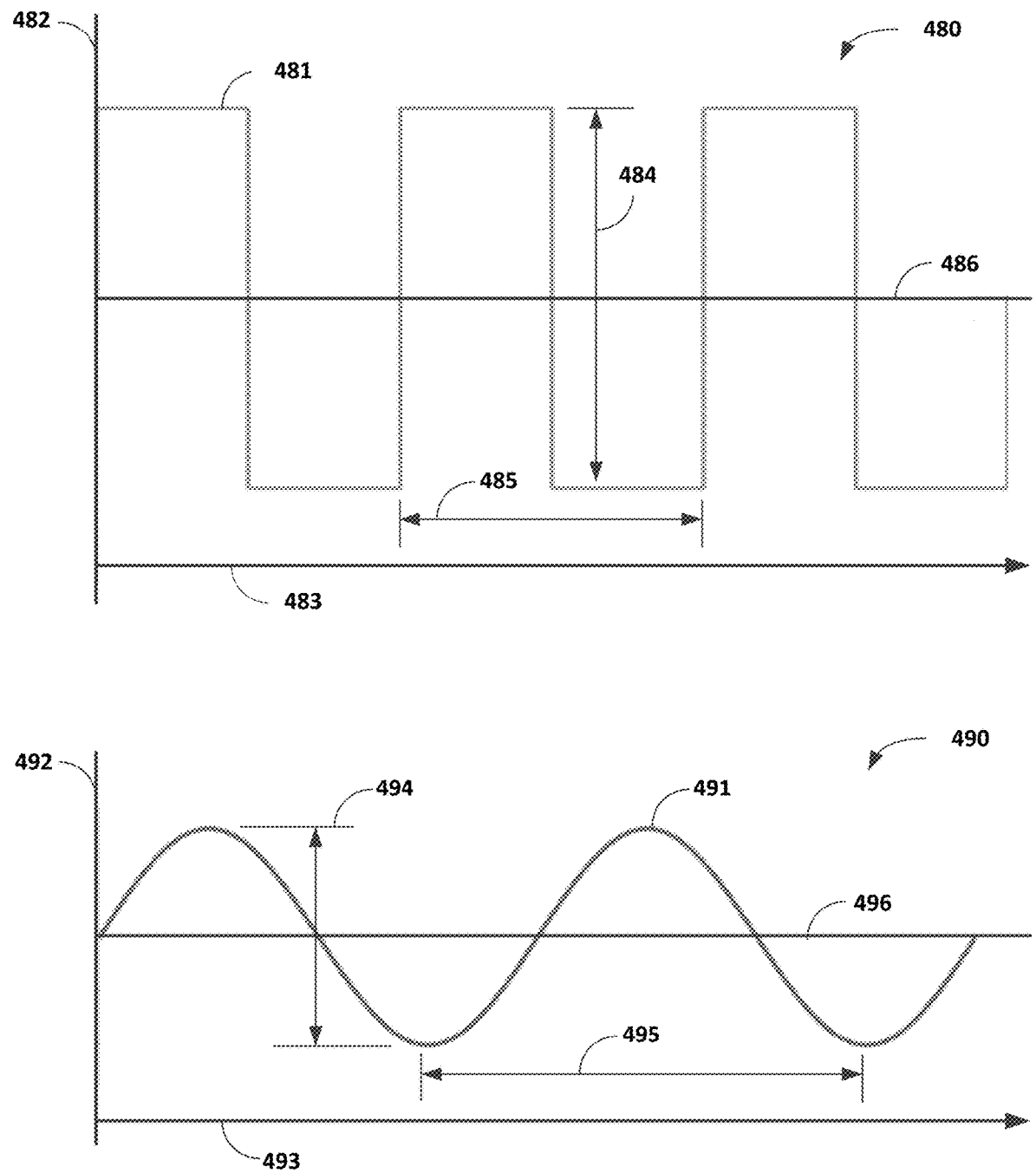
FIG. 13 illustrates graphs of representative waveforms that may be generated by a signal generator and applied to the recharging coils of a recharging circuitry according to various examples described in this disclosure.

FIG. 13 illustrates examples graphs 480, 490 of representative waveforms that may be generated by signal generator 404 and applied to the coils coupled to recharging circuitry according to various examples described in this disclosure. Graph 480 illustrates an example waveform 481 of a square wave having an amplitude value plotted against the vertical axis 482 over time, time represented by horizontal axis 483. Waveform 480 comprises a peak-to-peak amplitude 484, and a cycle period 485. In various examples, the peak-to-peak amplitude 484 may comprise a voltage range of 10 mV to 100 volts, in some examples, 5 volts. The peak-to-peak amplitude in some examples is dependent on the power amplifier selected that the signal 481 is being provided to in order to generate the output used to energize a set of recharging coils. In some examples, the power amplifier being driven by the waveform 480 is a fixed amplification power amplifier, capable of providing a 400 Watt output signal based on a variable input signal having a peak-to-peak amplitude 10-200 mV. In some examples, a reference voltage level 486 may comprise a zero-volt reference voltage, wherein a portion of waveform 481 is provided at voltage level that is a higher voltage than the reference voltage 486, and a portion of waveform 481 is provided at a voltage level that is less than the reference voltage level 486. In various examples, the duty cycle of waveform 481 over period 485 provides a fifty-percent duty cycle. In various examples, the duty cycle of waveform 481 over the period 485 provides a duty cycle other than a fifty-percent duty cycle. In various examples the time period 495 of waveform 491 is in a range of 100 microseconds to 100 nanoseconds, representative of a frequency range of 10 kHz to 10 MHz for waveform 490.

Graph 490 illustrates an example waveform 491 of a sinusoidal waveform generated from the signal generator 404, and having a varying amplitude value plotted against the vertical axis 492 over time, time represented by horizontal axis 493. Waveform 491 comprises a peak-to-peak amplitude 494, and having a period 495. In various examples, the peak-to-peak amplitude 494 may comprise a voltage range of 10 mV to 100 volts, in some examples, 5 volts peak-to-peak depending on the desired peak magnetic field intensity and the capacity of the power amplifier employed. In some examples, the power amplifier is a fixed 400 Watt power amplifier, in other example the power amplifier comprises a variable output between 2 Watt and 1 kW. In some examples, a reference voltage level 496 may comprise a zero-volt reference voltage, wherein a portion of waveform 491 provides a voltage level above the reference voltage level 496, and another portion of each cycle of waveform 491 comprises voltage value that is below the reference voltage level 496. In various examples, the duty cycle of waveform 481 over period 485 provides a fifty-percent duty cycle. In various examples the time period 495 of waveform 491 is in a range of 100 microseconds to 100 nanoseconds, representative of a frequency range of 10 kHz to 10 MHz for waveform 490.

Figure 14:
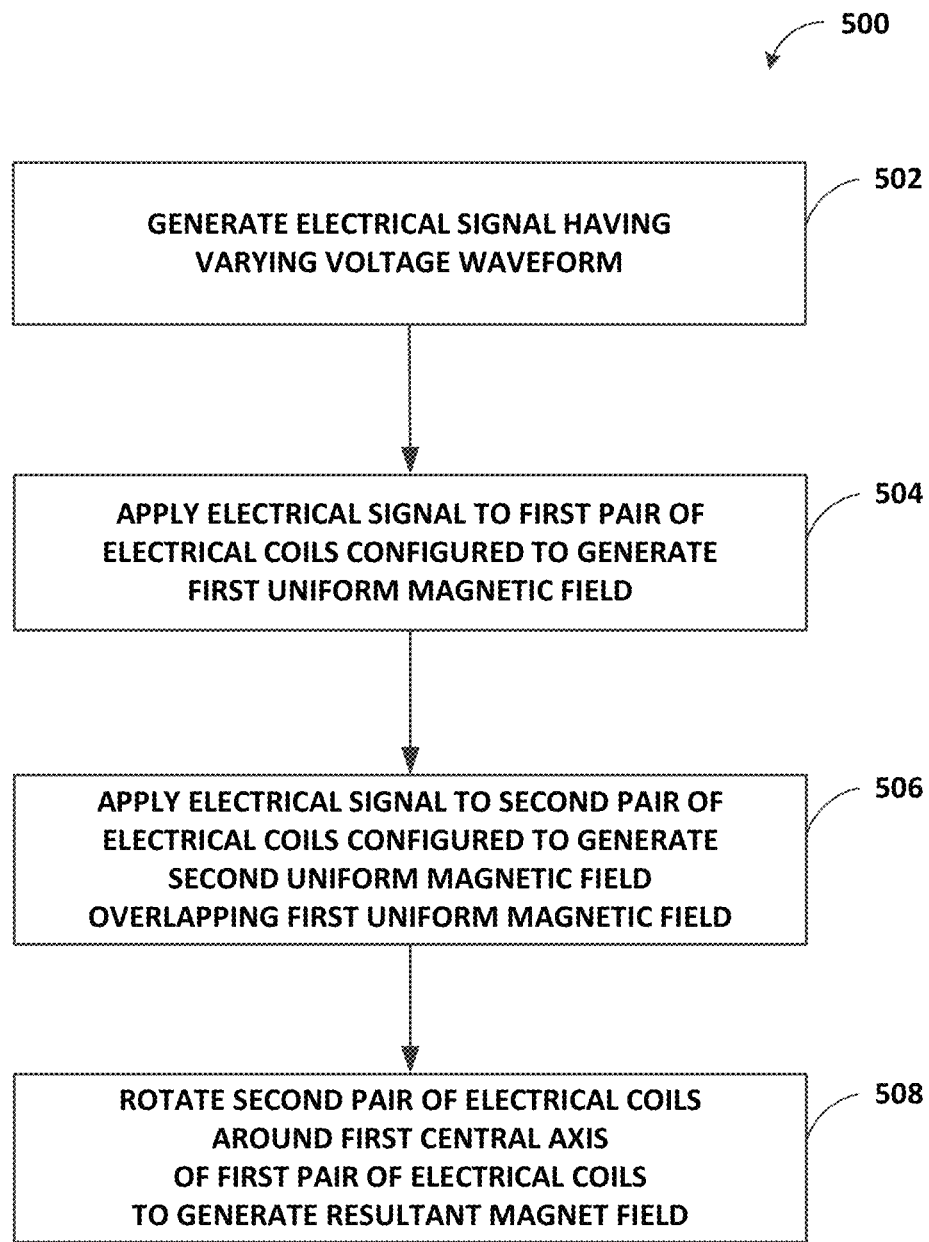
FIG. 14 is a flowchart illustrating a method according to various examples described in this disclosure.

FIG. 14 illustrates a flowchart illustrating a method 500 in according to various examples described in this disclosure. Although method 500 is described with respect to the devices and systems illustrated with respect to system 400 of FIGS. 12A and 12B, method 500 is not limited to being performed by system 400, and may be performed, in whole or in part, by any of the example devices and/or systems described in this disclosure, and the equivalents thereof. Method 500 includes a method for recharging a power source located in an implanted medical device 15 implanted in a patient 2.

Method 500 includes the generation, by signal generator 404, of an electrical signal having a varying voltage waveform (block 502). In some examples, the varying voltage waveform is a sinusoidal voltage waveform. In some examples, the varying voltage comprises a square wave. Method 500 further includes using a power amplifier 410, to apply the electrical signal to a first pair of electrical coils 351, in some examples configured to form a Helmholtz coil, the first pair of coils have a first central axis and are configured to generate a first uniform magnetic field in a first cylindrical region located between the first pair of coils when the first pair of coils are electrically energized (block 504). Method 500 further includes using a power amplifier 412 to apply the electrical signal to a second pair of electrical coils 361, the second pair of electrical coils 361 may be configured to form a Helmholtz coil having a second central axis, the second pair of coils 361 configured to generate a second uniform magnetic field in a second cylindrical region located between the second pair of coils when the second pair of coils is electrically energized (block 506).

In examples of method 500, the first uniform magnetic field and the second uniform magnetic field form a resultant magnetic field within an area common to both the first cylindrical region and the second cylindrical region, the resultant magnetic field operable to provide a charging energy to at least one receiving antenna of the implanted medical device located within the resultant magnetic field when the first pair of coils and the second pair of coils are electrically energized. In examples of method 500, the first pair of coils are separated from each other by a first distance and the second pair of coils are separated from each other by a second distance such that at least a portion the patient including the implanted medical device may be disposed in the resultant magnetic field of the area common to both the first cylindrical region and the second cylindrical region between the first pair of coils and the second pair of coils. Examples of method 500 further comprising using position controller 414 and motor 415 to rotate the second pair of coils around the first central axis so that when rotated, the second central axis remains perpendicular to the first central axis (block 508).

Examples of method 500 may further comprise using communication circuitry 444 to receive a feedback signal indicating a level of coupling between the resultant magnetic field and a receiving antenna of the implantable medical device 15 located within an area common to both the first cylindrical region and the second cylindrical region, and using a processor 441 coupled to communication circuitry 444 to determine a final position for the second pair of coils as the second pair of coils is being rotated around the first central axis based on the feedback signal. Method 500 may further include using position controller 414 and motor 415 to position the second pair of coils at the final position based on the feedback signal.

Examples of method 500 may further comprise using a third power amplifier 418 to apply an electrical signal to a third pair of electrical coils 371, the third pair of electrical coils in some examples configured to form a Helmholtz coil having a third central axis, the third pair of coils 371 configured to generate a third uniform magnetic field in a third cylindrical region located between the third pair of coils when the third pair of coils is electrically energized. Examples of method 500 include the first uniform magnetic field, the second uniform magnetic field, and the third uniform magnetic field forming a three-way overlapping region within an area common to both the first cylindrical region and the second cylindrical region and the third cylindrical region, the resultant magnetic field operable to provide a charging energy to at least one receiving antenna of the implanted medical device located within an area common to both the first cylindrical region and the second cylindrical region and the third cylindrical region when the first pair of coils and the second pair of coils and the third pair of coils are electrically energized. In examples of method 500 using three sets of coils, the rotation of the second pair of coils 361 to generated the resultant magnetic field may be unnecessary, and the coils remain at a fixed position relative to each other and to IMD 15 during the recharging process.

In various examples, instead of using two or three power amplifiers, method 500 comprises using a single power amplifier 410 configured to provide output power to a power divider 410A, the power divider 410A configured to divide the output power provided by amplifier 410 to energize each of coils 351, 361, and coils 371 (if coils 371 are being utilized). In various examples, one set, two, or all sets of coils 351, 361, and 371 (if coils 371 are provided) may be configured as Helmholtz coils. In various examples, one or more of coils 351, 361, and 371 (if coils 371 are being utilized) may be configured as a Maxwell coil.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. A system for recharging a power source of a medical device, the system comprising:
a first set of electrical coils comprising a first electrical coil, a second electrical coil, and a third electrical coil disposed along a first central axis, wherein the third electrical coil is positioned between the first electrical coil and the second electrical coil, and wherein the first set of electrical coils is configured to generate a first uniform magnetic field in a first cylindrical region located between the first electrical coil and the second electrical coil while the first set of three coils is electrically energized; and
a second set of electrical coils comprising a fourth electrical coil and a fifth electrical coil disposed along a second central axis perpendicular to the first central axis, wherein the second set of electrical coils is configured to generate a second uniform magnetic field in a second cylindrical region located between the fourth electrical coil and the fifth electrical coil while the second set of electrical coils is electrically energized, wherein a distance between the fourth electrical coil and the fifth electrical coil is greater than a diameter of the third electrical coil,
wherein the first uniform magnetic field and the second uniform magnetic field form a resultant magnetic field within an area common to both the first cylindrical region and the second cylindrical region, and
wherein the resultant magnetic field is operable to provide a charging energy to the medical device while the medical device is located within the resultant magnetic field and while the first set of electrical coils and the second set of electrical coils are electrically energized.

2. The system of claim 1, wherein the first electrical coil, the second electrical coil, and the third electrical coil of the first set of electrical coils are arranged as a Maxwell coil.

3. The system of claim 1, wherein the second set of electrical coils comprises a sixth electrical coil positioned between the fourth electrical coil and the fifth electrical coil.

4. The system of claim 3, wherein the fourth electrical coil, the fifth electrical coil, and the sixth electrical coil of the second set of electrical coils are arranged as a Maxwell coil.

5. The system of claim 1,
wherein a radius of the first electrical coil is substantially similar to a radius of the second electrical coil, and
wherein a radius of the third electrical coil is greater than either the radius of the first electrical coil or the radius of the second electrical coil.

6. The system of claim 1, wherein the medical device comprises an implantable medical device.

7. The system of claim 1, further comprising recharging circuitry configured to electrically energize the first set of electrical coils and the second set of electrical coils.

8. The system of claim 1, wherein each of the first set of electrical coils are separated from one another by a first distance and each of the second set of electrical coils are separated from one another by a second distance such that at least a portion of the medical device may be disposed in the resultant magnetic field within the area common to both the first cylindrical region and the second cylindrical region.

9. The system of claim 1, wherein the second set of coils is configured to be rotated around the first central axis so that when rotated, the second central axis remains perpendicular to the first central axis.

10. The system of claim 9, further comprising processing circuitry configured to:
receive a feedback signal indicating a level of coupling between the resultant magnetic field and the medical device; and
determine a final position of the second set of coils when rotated around the first central axis based on the feedback signal.

11. The system of claim 9, further comprising processing circuitry configured to:
receive a feedback signal indicating a variation in a strength of the resultant magnetic field within the area common to both the first cylindrical region and the second cylindrical region as the second set of coils is rotated around the first central axis; and
determine a final position of the second set of coils when rotated around the first central axis based on the feedback signal.

12. A method for recharging a power source of a medical device, the method comprising:
generating, by a signal generator, an electrical signal having a varying waveform;
applying, by a first driver circuit, the electrical signal to a first set of electrical coils comprising a first electrical coil, a second electrical coil, and a third electrical coil disposed along a first central axis, wherein the third electrical coil is positioned between the first electrical coil and the second electrical coil, and wherein the first set of electrical coils is configured to generate a first uniform magnetic field in a first cylindrical region located between the first electrical coil and the second electrical coil while the first set of three coils is electrically energized; and
applying, by a second driver circuit, the electrical signal to a second set of electrical coils comprising at least a fourth electrical coil and a fifth electrical coil disposed along a second central axis perpendicular to the first central axis, wherein the second set of electrical coils is configured to generate a second uniform magnetic field in a second cylindrical region located between the fourth electrical coil and the fifth electrical coil while the second set of electrical coils is electrically energized, wherein a distance between the fourth electrical coil and the fifth electrical coil is greater than a diameter of the third electrical coil,
wherein the first uniform magnetic field and the second uniform magnetic field form a resultant magnetic field within an area common to both the first cylindrical region and the second cylindrical region, and
wherein the resultant magnetic field is operable to provide a charging energy to the medical device while the medical device is located within the resultant magnetic field and while the first set of electrical coils and the second set of electrical coils are electrically energized.

13. The method of claim 12, wherein the first electrical coil, the second electrical coil, and the third electrical coil of the first set of electrical coils are arranged as a Maxwell coil.

14. The method of claim 12, wherein the second set of electrical coils comprises a sixth electrical coil positioned between the fourth electrical coil and the fifth electrical coil.

15. The method of claim 12,
wherein a radius of the first electrical coil is substantially similar to a radius of the second electrical coil, and
wherein a radius of the third electrical coil is greater than either the radius of the first electrical coil or the radius of the second electrical coil.

16. The method of claim 12, wherein each of the first set of electrical coils are separated from one another by a first distance and each of the second set of electrical coils are separated from one another by a second distance such that at least a portion of the medical device may be disposed in the resultant magnetic field within the area common to both the first cylindrical region and the second cylindrical region.

17. The method of claim 12, further comprising rotating the second set of coils around the first central axis so that when rotated, the second central axis remains perpendicular to the first central axis.

18. The method of claim 17, further comprising:
receiving, by processing circuitry, a feedback signal indicating a variation in a strength of the resultant magnetic field within the area common to both the first cylindrical region and the second cylindrical region as the second set of coils is rotated around the first central axis; and
determining, by the processing circuitry, a final position of the second set of coils when rotated around the first central axis based on the feedback signal,
wherein rotating the second set of coils around the first central axis comprises rotating the second set of coils around the first central axis to the final position.

19. The method of claim 18, wherein the medical device is implanted within a patient.

20. A system comprising:
an implantable medical device comprising a power source;
a first set of electrical coils comprising a first electrical coil, a second electrical coil, and a third electrical coil disposed along a first central axis, wherein the third electrical coil is positioned between the first electrical coil and the second electrical coil, and wherein the first set of electrical coils is configured to generate a first uniform magnetic field in a first cylindrical region located between the first electrical coil and the second electrical coil while the first set of three coils is electrically energized; and
a second set of electrical coils comprising at least a fourth electrical coil, a fifth electrical coil, and a sixth electrical coil disposed along a second central axis perpendicular to the first central axis, wherein the sixth electrical coil is positioned between the fourth electrical coil and the fifth electrical coil, and wherein the second set of electrical coils is configured to generate a second uniform magnetic field in a second cylindrical region located between the fourth electrical coil and the fifth electrical coil while the second set of electrical coils is electrically energized, wherein a distance between the fourth electrical coil and the fifth electrical coil is greater than a diameter of the third electrical coil, wherein the first uniform magnetic field and the second uniform magnetic field form a resultant magnetic field within an area common to both the first cylindrical region and the second cylindrical region, and wherein the resultant magnetic field is operable to provide a charging energy to the implantable medical device while the implantable medical device is located within the resultant magnetic field and while the first set of electrical coils and the second set of electrical coils are electrically energized.

* * * * *